(12) United States Patent
Sharma et al.

(10) Patent No.: US 7,709,484 B1
(45) Date of Patent: May 4, 2010

(54) SUBSTITUTED MELANOCORTIN RECEPTOR-SPECIFIC PIPERAZINE COMPOUNDS

(75) Inventors: Shubh D. Sharma, Cranbury, NJ (US); Yi-Qun Shi, East Brunswick, NJ (US); Zhijun Wu, Plainsboro, NJ (US); Bolun Hu, East Windsor, NJ (US); Ramesh Rajpurohit, Hillsboro, NJ (US)

(73) Assignee: Palatin Technologies, Inc., Cranbury, NJ (US)

( * ) Notice: Subject to any disclaimer, the term of this patent is extended or adjusted under 35 U.S.C. 154(b) by 959 days.

(21) Appl. No.: 11/110,060

(22) Filed: Apr. 19, 2005

Related U.S. Application Data

(60) Provisional application No. 60/563,738, filed on Apr. 19, 2004.

(51) Int. Cl.
*A61K 31/497* (2006.01)
*C07D 241/04* (2006.01)
*C07D 403/04* (2006.01)
*C07D 405/04* (2006.01)
*C07D 295/04* (2006.01)

(52) U.S. Cl. .......................... 514/252.12; 514/252.13; 514/254.01; 544/358; 544/359; 544/372; 544/386

(58) Field of Classification Search ............... 544/358, 544/359, 372, 386; 514/252.12, 252.13, 514/254.01
See application file for complete search history.

(56) References Cited

U.S. PATENT DOCUMENTS

| | | | |
|---|---|---|---|
| 4,148,923 A | 4/1979 | Giudicelli et al. |
| 4,239,763 A | 12/1980 | Milavec et al. |
| 4,626,549 A | 12/1986 | Molloy et al. |
| 4,680,289 A | 7/1987 | Applezweig |
| 4,711,957 A | 12/1987 | Lai |
| 4,766,125 A | 8/1988 | Van Daele |
| 4,937,267 A | 6/1990 | Holloway et al. |
| 4,938,763 A | 7/1990 | Dunn et al. |
| 4,943,578 A | 7/1990 | Naylor et al. |
| 4,968,684 A | 11/1990 | Van Daele et al. |
| 4,997,836 A | 3/1991 | Sugihara et al. |
| 5,120,713 A | 6/1992 | Mugica |
| 5,292,726 A | 3/1994 | Ashton et al. |
| 5,331,573 A | 7/1994 | Balaji et al. |
| 5,334,830 A | 8/1994 | Fukuyama et al. |
| 5,348,955 A | 9/1994 | Greenlee et al. |
| 5,464,788 A | 11/1995 | Bock et al. |
| 5,494,919 A | 2/1996 | Morriello et al. |
| 5,550,131 A | 8/1996 | Sugihara et al. |
| 5,574,031 A | 11/1996 | Abramo et al. |
| 5,579,250 A | 11/1996 | Balaji et al. |
| 5,599,809 A | 2/1997 | Hickey et al. |
| 5,639,778 A | 6/1997 | Andersson et al. |
| 5,672,602 A | 9/1997 | Burkholder et al. |
| 5,721,250 A | 2/1998 | Morriello et al. |
| 5,721,251 A | 2/1998 | Chen et al. |
| 5,736,539 A | 4/1998 | Graham et al. |
| 5,753,445 A | 5/1998 | Fillit et al. |
| 5,753,653 A | 5/1998 | Bender et al. |
| 5,763,445 A | 6/1998 | Kruse et al. |
| 5,798,359 A | 8/1998 | Shue et al. |
| 5,804,578 A | 9/1998 | Chakravarty et al. |
| 5,856,326 A | 1/1999 | Anthony et al. |
| 5,872,262 A | 2/1999 | Dolle, III et al. |

(Continued)

FOREIGN PATENT DOCUMENTS

WO  WO 96/38471  12/1996

(Continued)

OTHER PUBLICATIONS

*Synthetic Peptides: A User's Guide*, GA Grant, editor, W.H. Freeman & Co., New York, 1992, the teachings of which are incorporated herein by reference, including the text and table set forth at pp. 11-24.

(Continued)

*Primary Examiner*—James O Wilson
*Assistant Examiner*—Ebenezer Sackey
(74) *Attorney, Agent, or Firm*—Stephen A. Slusher

(57) ABSTRACT

A substituted piperazine compound having the structure I:

I or the structure IX:

IX or an enantiomeric, stereoisomeric or diastereomeric form of the foregoing, and pharmaceutically acceptable salts thereof, where J, L, Q, W, A, $R_6$, $R_7$, z and y are as defined in the specification, and the carbon atoms marked with an asterisk can have any stereochemical configuration, which compounds bind to one or more melanocortin receptors and may be employed in pharmaceutical preparations for treatment of one or more melanocortin receptor-associated conditions or disorders, and methods for the use of the compounds of the invention.

19 Claims, No Drawings

U.S. PATENT DOCUMENTS

| | | |
|---|---|---|
| 5,877,182 A | 3/1999 | Nargund et al. |
| 5,880,125 A | 3/1999 | Nargund |
| 5,880,128 A | 3/1999 | Doll et al. |
| 5,891,418 A | 4/1999 | Sharma |
| 5,892,038 A | 4/1999 | Dolle, III et al. |
| 5,936,089 A | 8/1999 | Carpino et al. |
| 5,965,565 A | 10/1999 | Chen et al. |
| 5,968,938 A | 10/1999 | Williams et al. |
| 6,020,334 A | 2/2000 | Fukushi et al. |
| 6,027,711 A | 2/2000 | Sharma |
| 6,033,656 A | 3/2000 | Mikami et al. |
| 6,127,381 A | 10/2000 | Basu et al. |
| 6,127,424 A | 10/2000 | Martin et al. |
| 6,140,354 A | 10/2000 | Dax et al. |
| 6,162,805 A | 12/2000 | Hefti |
| 6,191,117 B1 | 2/2001 | Kozachuk |
| 6,207,665 B1 | 3/2001 | Bauman et al. |
| 6,207,699 B1 | 3/2001 | Rothman |
| 6,214,831 B1 | 4/2001 | Yokoo et al. |
| 6,245,764 B1 | 6/2001 | Kahn et al. |
| 6,284,735 B1 | 9/2001 | Girten et al. |
| 6,294,539 B1 | 9/2001 | Lou et al. |
| 6,303,611 B1 | 10/2001 | Zhang et al. |
| 6,316,470 B1 | 11/2001 | Kover et al. |
| 6,331,285 B1 | 12/2001 | Sharma |
| 6,340,868 B1 | 1/2002 | Lys et al. |
| 6,350,760 B1 | 2/2002 | Bakshi et al. |
| 6,372,747 B1 | 4/2002 | Taveras et al. |
| 6,376,509 B1 | 4/2002 | Bakshi et al. |
| 6,410,548 B2 | 6/2002 | Nargund et al. |
| 6,432,438 B1 | 8/2002 | Shukla |
| 6,432,959 B1 | 8/2002 | Cooper et al. |
| 6,451,783 B1 | 9/2002 | Hadcock et al. |
| 6,458,789 B1 | 10/2002 | Forood et al. |
| 6,458,790 B2 | 10/2002 | Palucki et al. |
| 6,469,006 B1 | 10/2002 | Blair et al. |
| 6,472,398 B1 | 10/2002 | Palucki et al. |
| 6,486,165 B2 | 11/2002 | Zhang et al. |
| 6,515,122 B1 | 2/2003 | Lang et al. |
| 6,531,476 B1 | 3/2003 | Heymans et al. |
| 6,534,503 B1 | 3/2003 | Dines et al. |
| 6,534,509 B1 | 3/2003 | Bauman et al. |
| 6,555,537 B2 | 4/2003 | Bauman et al. |
| 6,569,861 B2 | 5/2003 | Bakthavatchalam et al. |
| 6,579,968 B1 | 6/2003 | Blood et al. |
| 6,612,805 B2 | 9/2003 | Rietsch |
| 6,648,848 B1 | 11/2003 | Keldmann et al. |
| 6,673,767 B1 | 1/2004 | Brodbeck et al. |
| 6,699,873 B1 | 3/2004 | Maguire et al. |
| 6,715,485 B1 | 4/2004 | Djupesland |
| 6,734,175 B2 | 5/2004 | Hadcock et al. |
| 6,811,543 B2 | 11/2004 | Keldmann et al. |
| 6,949,552 B2 | 9/2005 | Nakazato et al. |
| 7,326,707 B2 | 2/2008 | Sharma et al. |
| 7,354,923 B2 | 4/2008 | Sharma et al. |
| 7,456,184 B2 | 11/2008 | Sharma et al. |
| 2001/0018075 A1 | 8/2001 | Shigeyuki et al. |
| 2001/0047001 A1 | 11/2001 | Varkhedkar et al. |
| 2002/0004512 A1 | 1/2002 | Bakshi et al. |
| 2002/0010182 A1 | 1/2002 | Masaaki et al. |
| 2002/0019523 A1 | 2/2002 | Palucki et al. |
| 2002/0022620 A1 | 2/2002 | Kahn et al. |
| 2002/0032238 A1 | 3/2002 | Priepke et al. |
| 2002/0037837 A1 | 3/2002 | Takada et al. |
| 2002/0042399 A1 | 4/2002 | Kruse et al. |
| 2002/0052383 A1 | 5/2002 | Bakthavatchalam et al. |
| 2002/0065277 A1 | 5/2002 | Hadcock et al. |
| 2002/0065416 A1 | 5/2002 | Stasiak et al. |
| 2002/0072604 A1 | 6/2002 | Carpino et al. |
| 2002/0082263 A1 | 6/2002 | Lou et al. |
| 2002/0107253 A1 | 8/2002 | Koh et al. |
| 2002/0107255 A1 | 8/2002 | Blumberg et al. |
| 2002/0128247 A1 | 9/2002 | Dow et al. |
| 2002/0128270 A1 | 9/2002 | Neya et al. |
| 2002/0137664 A1 | 9/2002 | Bakshi et al. |
| 2002/0143141 A1 | 10/2002 | Chen et al. |
| 2002/0173512 A1 | 11/2002 | Moltzen et al. |
| 2002/0177598 A1 | 11/2002 | Bauman et al. |
| 2002/0183316 A1 | 12/2002 | Pan et al. |
| 2003/0004162 A1 | 1/2003 | Treadway |
| 2003/0013721 A1 | 1/2003 | Meghani et al. |
| 2003/0040520 A1 | 2/2003 | Guzi et al. |
| 2003/0055008 A1 | 3/2003 | Marcotte |
| 2003/0055009 A1 | 3/2003 | Steiner et al. |
| 2003/0055247 A1 | 3/2003 | Cosford et al. |
| 2003/0055265 A1 | 3/2003 | Binggeli et al. |
| 2003/0060473 A1 | 3/2003 | Neya et al. |
| 2003/0064921 A1 | 4/2003 | Millhauser et al. |
| 2003/0069169 A1 | 4/2003 | Macor et al. |
| 2003/0083228 A1 | 5/2003 | Carpino et al. |
| 2003/0083335 A1 | 5/2003 | Hayward |
| 2003/0092732 A1 | 5/2003 | Yu et al. |
| 2003/0096827 A1 | 5/2003 | Yu et al. |
| 2003/0105106 A1 | 6/2003 | Chiang et al. |
| 2003/0109556 A1 | 6/2003 | Mazur et al. |
| 2003/0125334 A1 | 7/2003 | Chiang et al. |
| 2003/0139425 A1 | 7/2003 | Bauman et al. |
| 2003/0144277 A1 | 7/2003 | DeLucca |
| 2003/0149019 A1 | 8/2003 | Bremberg et al. |
| 2003/0158205 A1 | 8/2003 | Bauman et al. |
| 2003/0158209 A1 | 8/2003 | Dyck et al. |
| 2003/0162819 A1 | 8/2003 | Eisinger et al. |
| 2003/0166637 A1 | 9/2003 | Lehmann-Lintz et al. |
| 2003/0176425 A1 | 9/2003 | Eisinger et al. |
| 2003/0181441 A1 | 9/2003 | McClure et al. |
| 2003/0191136 A1 | 10/2003 | Bakthavatchalam et al. |
| 2003/0195212 A1 | 10/2003 | Lundstedt et al. |
| 2004/0006067 A1 | 1/2004 | Fotsch et al. |
| 2004/0024211 A1 | 2/2004 | Boyce et al. |
| 2004/0034034 A1 | 2/2004 | Blumberg et al. |
| 2004/0053933 A1 | 3/2004 | Pontillo et al. |
| 2004/0147567 A1 | 7/2004 | Nakazato et al. |
| 2004/0152534 A1 | 8/2004 | Chapman et al. |
| 2004/0157264 A1 | 8/2004 | Sharma et al. |
| 2004/0171520 A1 | 9/2004 | Sharma et al. |
| 2004/0204398 A1 | 10/2004 | Bakshi et al. |
| 2004/0224957 A1 | 11/2004 | Sharma et al. |
| 2004/0254198 A1 | 12/2004 | Reynolds et al. |
| 2005/0124636 A1 | 6/2005 | Sharma et al. |
| 2005/0130988 A1 | 6/2005 | Sharma et al. |
| 2005/0176728 A1* | 8/2005 | Sharma et al. ......... 514/253.01 |
| 2006/0009456 A1 | 1/2006 | Hutchinson et al. |
| 2006/0084657 A1 | 4/2006 | Nakazato et al. |
| 2006/0287330 A1 | 12/2006 | Sharma et al. |
| 2006/0287331 A1 | 12/2006 | Sharma et al. |
| 2006/0287332 A1 | 12/2006 | Sharma et al. |
| 2008/0070921 A1 | 3/2008 | Burris et al. |
| 2008/0234289 A1 | 9/2008 | Sharma et al. |
| 2009/0076029 A1 | 3/2009 | Sharma et al. |
| 2009/0081197 A1 | 3/2009 | Burris et al. |

FOREIGN PATENT DOCUMENTS

| | | |
|---|---|---|
| WO | WO 97/46553 | 12/1997 |
| WO | WO 98/10653 | 3/1998 |
| WO | WO 98/17625 | 4/1998 |
| WO | WO 99/55679 | 11/1999 |
| WO | WO 99/58501 | 11/1999 |
| WO | WO 99/64002 | 12/1999 |
| WO | WO 00/01726 | 1/2000 |
| WO | WO 00/05373 | 2/2000 |
| WO | WO 00/17348 | 3/2000 |
| WO | WO 00/35952 | 6/2000 |
| WO | WO 00/36136 | 6/2000 |

| | | |
|---|---|---|
| WO | WO 00/40247 | 7/2000 |
| WO | WO 00/53148 | 9/2000 |
| WO | WO 00/68185 | 11/2000 |
| WO | WO 00/74679 | 12/2000 |
| WO | WO 01/05401 | 1/2001 |
| WO | WO 01/10842 | 2/2001 |
| WO | WO 01/12176 | 2/2001 |
| WO | WO 01/13112 | 2/2001 |
| WO | WO 01/18210 | 3/2001 |
| WO | WO 01/21634 | 3/2001 |
| WO | WO 01/21647 | 3/2001 |
| WO | WO 01/30808 | 3/2001 |
| WO | WO 01/23392 | 4/2001 |
| WO | WO 01/30343 | 5/2001 |
| WO | WO 01/35970 | 5/2001 |
| WO | WO 01/52880 | 7/2001 |
| WO | WO 01/55106 | 8/2001 |
| WO | WO 01/55107 | 8/2001 |
| WO | WO 01/55109 | 8/2001 |
| WO | WO 01/70708 | 9/2001 |
| WO | WO 01/91752 | 12/2001 |
| WO | WO 02/00259 | 1/2002 |
| WO | WO 02/00654 | 1/2002 |
| WO | WO 02/12178 | 2/2002 |
| WO | WO 02/15909 | 2/2002 |
| WO | WO 02/18437 | 3/2002 |
| WO | WO 02/47670 | 6/2002 |
| WO | WO 02/059095 | 8/2002 |
| WO | WO 02/059107 | 8/2002 |
| WO | WO 02/059108 | 8/2002 |
| WO | WO 02/059117 | 8/2002 |
| WO | WO 02/062766 | 8/2002 |
| WO | WO 02/064091 | 8/2002 |
| WO | WO 02/064734 | 8/2002 |
| WO | WO 02/067869 | 9/2002 |
| WO | WO 02/068387 | 9/2002 |
| WO | WO 02/068388 | 9/2002 |
| WO | WO 02/069905 | 9/2002 |
| WO | WO 02/070511 | 9/2002 |
| WO | WO 02/079146 | 10/2002 |
| WO | WO 02/079203 | 10/2002 |
| WO | WO 02/079753 | 10/2002 |
| WO | WO 02/081443 | 10/2002 |
| WO | WO 02/085925 | 10/2002 |
| WO | WO 02/092566 | 11/2002 |
| WO | WO 03/006620 | 1/2003 |
| WO | WO 03/007949 | 1/2003 |
| WO | WO 03/009847 | 2/2003 |
| WO | WO 03/009850 | 2/2003 |
| WO | WO 03/013509 | 2/2003 |
| WO | WO 03/013571 | 2/2003 |
| WO | WO 03/020724 | 3/2003 |
| WO | WO 03/027239 | 4/2003 |
| WO | WO 03/031410 | 4/2003 |
| WO | WO 03/045920 | 6/2003 |
| WO | WO 03/053927 | 7/2003 |
| WO | WO 03/055477 | 7/2003 |
| WO | WO 03/061660 | 7/2003 |
| WO | WO 03/066587 | 8/2003 |
| WO | WO 03/066597 | 8/2003 |
| WO | WO 03/072056 | 9/2003 |
| WO | WO 03/092690 | 11/2003 |
| WO | WO 03/093234 | 11/2003 |
| WO | WO 03/094918 | 11/2003 |
| WO | WO 2004/037796 | 5/2004 |
| WO | WO 2005/102340 | 11/2005 |
| WO | WO 2006/014552 | 2/2006 |
| WO | WO 2007/021990 | 2/2007 |
| WO | WO 2007/021991 | 2/2007 |

OTHER PUBLICATIONS

Hruby VJ, Al-obeidi F and Kazmierski W: *Biochem J* 268:249-262, 1990.

Toniolo C: *Int J Peptide Protein Res* 35:287-300, 1990.

U.S. Appl. No. 12/130,299, filed May 30, 2008, Burris et al.

U.S. Appl. No. 12/130,316, filed May 30, 2008, Sharma et al.

Abou-Gharbia et al. "Synthesis and SAR of Adatanserin: Novel Adamantyl Aryl- and Heteroarylpiperazines with Dual Serotonin 5-HT$_{1A}$ and 5-HT$_2$ Activity as Potential Anxiolytic and Antidepressant Agents" J. Med. Chem. 42(25):5077-5094 (1999).

Adan et al. "Identification of antagonists for melanocortin MC3, MC4 and MC5 receptors" Eur. J. Pharmacol. 269(3): 331-337 (1994).

Adan et al. "Inverse agonism gains weight" Trends in Pharmacological Sciences 24(6):315-321 (2003).

Alterman et al. "Design and synthesis of new potent C2-symmetric HIV-1 protease inhibitors. Use of L-mannaric acid as a peptidomimetic scaffold" J. Med. Chem. 41:3782-3792 (1998).

Baldwin et al. "Synthesis of a bicyclic γ-lactam dipeptide analogue" Tetrahedron Letters 34(10):1665-1668 (1993).

Chang et al. "Morphiceptin (NH4-tyr-pro-phe-pro-COHN2): a potent and specific agonist for morphine (mu) receptors" Science 212(4490):75-77 (1981).

Cho et al. "Discovery of novel, potent and orally active nonpeptide antagonist of the human luteinizing hormone-releasing hormone (LHRH) receptor" J. Med. Chem. 41:4190-4195 (1998).

Chorev et al. "Toward nonpeptidal substance P mimetic analogues: Design, synthesis, and biological activity" Biopolymers 31(6):725-733 (1991).

Cornille et al. "Anodic amide oxidations: Conformationally restricted peptide building blocks from the direct oxidation of dipeptides" Tetrahedron Letters 35(38):6989-6992 (1994).

DiMaio et al. "Synthesis of chiral piperazin-2-ones as model peptidomimetics" J. Chem. Soc., Perkin Trans I, 1687-1689 (1989).

Dorr et al. "Evaluation of melanotan-II, a superpotent cyclic melanotropic peptide in a pilot phase-I clinical study" Life Science 58(20): 1777-1784 (1996).

Gante "Peptidomimetics—Tailored enzyme-inhibitors" Angewandte Chemie International Edition in English 33(17): 1699-1720 (1994).

Giannis et al. "Peptidomimetics in drug design" Advances in Drug Research 29:1-78 (1997).

Hadley et al. "Discovery and development of novel melanogenic drugs. Melanotan-I and -II" Ronald T. Borchardt, et al. editors; Integration of Pharmaceutical Discovery and Development: Case Histories, Plenum Press, New York, 575-595 (1998).

Haskell-Luevano et al. "Discovery of Prototype Peptidomimetic Agonists at the Human Melanocortin Receptors MC1R and MC4R" J. Med. Chem. 40:2133-2139 (1997).

Hruby et al. "Molecular organization of receptors—Efficacy, agonists, and antagonists" Annals of the New York Academy of Sciences 757:7-22 (1995).

Jones et al. "Clinically validated peptides as templates for de novo peptidomimetic drug design at G-protein coupled receptors" Current Opinion in Pharmacology 3:530-543 (2003).

Kask et al. "Discovery of a novel superpotent and selective melanocortin-4 receptor antagonist (HS024): Evaluation in vitro and in vivo" Endocrinology 139(12):5006-5014 (1998).

Kim et al. "Synthesis of (3R)-carboxy pyrrolidine (a β-proline analogue) and its oligomer" Bioorganic & Medicinal Chemistry Letters 10(21):2417-2419 (2000).

Klein et al. "O-benzyl hydroxyproline as a bioisostere for Phe-Pro: Novel dipeptide thrombin inhibitors" Bioorganic & Medicinal Chemistry Letters 6(18):2225-2230 (1996).

Lerner et al. "Synthetic melanocortin receptor. Agonist and antagonists" Cutaneous Neuroimmunomodulation: The Proopiomelanocortin System, Annals of the New York Academy of Sciences 885:153-160 (1995).

Medical Encyclopaedia: Female sexual dysfunction [online]. Retrieved on Oct. 10, 2007 from http://www.nlm.nih.gov/medlineplus/ency/article/003151.htm.

Mitsunobu "The use of diethyl azodicarboxylate and triphenylphosphine in synthesis and transfromation of natural products" Synthesis 1:1-28 (1981).

Moore et al. "A rapid screening system to determine drug affinities for the instestinal dipeptide transporter 2: Affinities of ACE inhibitors" International Journal of Pharmaceutics 210: 29-44 (2000).

Moore et al. "Designing Peptide Mimetics" Trends Pharmacol. Sci. 15:124-129 (1994).

Rarey et al. "Similarity searching in large combinatorial chemistry spaces" J. Computer-Aided Mol. Des. 15(6):497-520 (2001).

Rubsam et al. "Synthesis of chiral piperazinones as versatile scaffolds for peptidomimetics" Tetrahedron 56(43):8481-8487 (2000).

Sasaki et al. "Discovery of a thieno[2,3-d]pyrimidine-2,4-dione bearing a p-methoxyureidophenyl moiety at the 6-position: A highly potent and orally bioavailable non-peptide antagonist for the human luteinizing hormone-releasing hormone receptor" J. Med. Chem. 46:113-124 (2003).

Schioth et al. "Pharmacological comparison of rat and human melanocortin 3 and 4 receptors in vitro" Regulatory Peptides 106:7-12 (2002).

Shvachkin et al. "Synthesis of analogs of the thyrotropin-releasing hormone" Journal of General Chemistry of the USSR in English Translation 43(3):686-687 (1973).

Stavropoulos et al. "Synthesis of cis-4-hydroxy-L-proline and its incorporation into biologically important peptides" Review of Clinical Pharmacology and Pharmacokinetics 103-106 (1995).

Sudoh et al. "Transport characteristics of peptidomimetics. Effect of the pyrrolinone bioisostere of transport across caco-2 cell monolayers" Pharmaceutical Research 15(5):719-725 (1998).

Takenaka et al. "Synthesis of met- and leu-enkephalin analogues containing chiral N,N-ethylene-bridged phenylalanyl-methionine and -leucine" J Chem. Soc., Perkin Trans I, 8:933-937 (1993).

Torres et al. "Neoglycopeptide synthesis and purification in multigram scale: preparation of O-(2,3,4,6-tetra-O-acetyl-beta-D-galactopyranosyl)-N alpha-fluoren-9-yl-methoxycarbonyl-hydroxyproline and its use in the pilot-scale synthesis of the potent analgesic glycopeptide O1.5-beta-D-galactopyranosyl [DMet2, Hyp5]enkephalinamide." Journal of Peptide Science 3(2):99-109 (1997).

Torres et al. "Synthesis and conformational analysis of a series of galactosyl enkephalin analogues showing high analgesic activity" The EMBO Journal 8(10):2925-2932 (1989).

Yamamoto "Synthesis and adhesive studies of marine polypeptides" J. Chem. Soc., Perkin Trans I, 3:613-618 (1987).

Zhorov et al. "Similarity of Ca2+-bound conformations of morphine and Met-enkephalin: A computational study" FEBS Letters 354(2):131-134 (1994).

Cachexia [online], retrieved on Nov. 19, 2009 from the internet (URL: http://en.wikipedia.org/wiki/Cachexia).

Inui "Cancer anorexia-cachexia syndrome: Current issues in research and management" CA A Cancer Journal for Clinicians 52:72-91 (2002).

Fan et al. "Role of melanocortinergic neurons in feeding and the agouti obesity syndrome" Nature 385(6612):165-168 (1997).

Holder et al. "Melanocortin ligands: 30 years of structure-activity relationship (SAR) studies" Medicinal Research Reviews 24(3): 325-356 (2004).

Hruby et al. "Synthesis of oligopeptide and peptidomimetic libraries" Current Opinion in Chemical Biology 1(1): 114-119 (1997).

* cited by examiner

SUBSTITUTED MELANOCORTIN RECEPTOR-SPECIFIC PIPERAZINE COMPOUNDS

CROSS-REFERENCE TO RELATED APPLICATION

This application claims the benefit of the filing of U.S. Provisional Patent Application 60/563,738, entitled "Substituted Melanocortin-Receptor-Specific piperazine Compounds", filed on Apr. 19, 2004, and the specification thereof is incorporated herein by reference.

BACKGROUND OF THE INVENTION

1. Field of the Invention (Technical Field)

The present invention relates to substituted piperazine compounds characterized in that the piperazine compounds have a single unsubstituted ring nitrogen, which compounds bind to one or more melanocortin receptors and are agonists, antagonists, mixed agonist-antagonists, or inverse agonists with respect to one or more melanocortin receptors, and use thereof for the treatment of metabolic, immune, infection-related and melanocortin receptor mediated disorders.

2. Background Art

A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R), expressed primarily in cells in the hypothalamus, midbrain and brainstem, and melanocortin-5 receptors (MC5-R), expressed in a wide distribution of tissues.

In general, compounds specific for MC1-R are believed to be useful for treatment of melanoma. Compounds specific for MC3-R or MC4-R are believed to be useful in regulation of energy homeostasis, including use as agents for attenuating food intake and body weight gain, for use in treatment of anorexia, as a weight gain aid, for treatment of obesity, and treatment of other food intake and metabolism-related purposes. Compounds specific for MC3-R and MC4-R, among other melanocortin receptors, can further be used as agents for treatment of sexual dysfunction, including male erectile dysfunction. Other melanocortin receptor-specific compounds, such as MCR-1 agonists, can be used as tanning agents to increase melanin production in the skin, acting as chemo-preventive agents against harmful effects of UV solar radiation. Compounds specific for MCR-1 and MCR-3 may further be useful in regulation of inflammatory processes.

There is a significant need for compounds with high specificity for discrete melanocortin receptors, as well as for compounds that are either agonists or antagonists for specific melanocortin receptors. High affinity compounds for melanocortin receptors can be used to exploit varied physiological responses associated with the melanocortin receptors, either as agonists or antagonists. In addition, melanocortin receptors have an effect on the activity of various cytokines, and high affinity compounds for melanocortin receptors can be used to regulate cytokine activity.

There are piperazine and piperidine compounds known, such as those disclosed in WO 02/070511 (Bristol-Myers Squibb Company), WO 02/059095 (Eli Lilly and Company), and WO 00/74679 (Merck & Co., Inc.), asserted to be specific for melanocortin or related receptors. However, in general such compounds have at most two functional substituted groups, wherein each structure is further diversified to make these melanocortin agents. Moreover, these compounds have relatively poor affinity and specificity, and are not suitable for use as a drug compound. Further, none of the piperazine compounds have a single unsubstituted ring nitrogen. There is a significant need for compounds with high specificity for discrete receptors, such as melanocortin and other receptors, as well as compounds that are agonists or antagonists for such receptors. High affinity compounds for such receptors can be used to exploit varied physiological responses associated with the receptors, either as agonists or antagonists. There is thus a need for compounds that are more selective, including higher affinity and specificity that are optimized around a ring structure with at least two to four simple biologically active substituted groups. This invention addresses that need.

WO 02/085925, "Melanocortin Receptor Ligands" (The Proctor & Gamble Company), discloses ketopiperazine structures and methods of synthesis thereof, but does not disclose methods to synthesize piperazine structures, the methods of this invention to synthesize piperazine structures, or methods to synthesize optically pure structures, and further does not disclose piperazine compounds with a substituent group that is a single D-Phe residue, or a derivative or homolog thereof, optionally with an amine capping group. All the compounds disclosed therein differ from the present invention in a number of ways, including that all compounds disclosed have a substituent with a nitrogen-containing heteroatom cationic center.

With respect to certain objects, methods, synthetic schemes, utilities, applications, definitions, protocols and other disclosures, this application is related to U.S. patent application Ser. No. 10/762,079, entitled "piperazine Melanocortin-Specific Compounds", filed on Jan. 21, 2004; U.S. patent application Ser. No. 10/837,519, entitled "Melanocortin Receptor-Specific Compounds", filed on Apr. 30, 2004; International Application No. PCT/US02/25574, International Publication No. WO 03/013571, entitled "Peptidomimetics of Biologically Active Metallopeptides", filed on Aug. 12, 2002; and the specifications of each of the foregoing are incorporated herein by reference as if set forth in full.

SUMMARY OF THE INVENTION

The invention provides a compound having the structure I:

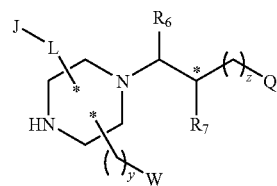

I or an enantomeric, stereoisomeric or diastereomeric form of the foregoing, and pharmaceutically acceptable salts thereof;
wherein
J is a substituted or unsubstituted monocyclic or bicyclic ring structure, wherein in each instance the ring or rings have 5 or 6 ring atoms;
L is a bond or a linker selected from the group consisting of
—$(CH_2)_q$—, —$(CH_2)_q$—O—, —$(CH_2)_q$—O—(C=O)—, —$(CH_2)_q$—NH—, —$(CH_2)_q$—NH—(C=O)—, —$(CH_2)_q$—(C=O)—, —$(CH_2)_q$—(C=O)—NH— and —$(CH_2)_q$—(C=O)—O—;
W is H or a substituted or unsubstituted aryl group;
Q is a ring group comprising at least one aryl group;
$R_6$ is H, =O, =S or $CH_3$;

$R_7$ is H, $NH_2$, $NH-R_8$, or

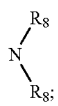

$R_8$ is a $C_1$ to $C_6$ linear or branched chain, an amine capping group, a natural or unnatural amino acid containing an aliphatic or aromatic side chain, or a natural or unnatural amino acid containing an aliphatic or aromatic side chain with a pendant amine capping group, and where there are two $R_8$ groups, each $R_8$ is independently a $C_1$ to $C_6$ linear or branched chain or an amine capping group, or one $R_8$ is a $C_1$ to $C_6$ linear or branched chain or an amine capping group and the remaining $R_8$ is a natural or unnatural amino acid containing an aliphatic or aromatic side chain or a natural or unnatural amino acid containing an aliphatic or aromatic side chain with a pendant amine capping group;

q is from 1 to 6;
y is from 0 to 6;
z is from 0 to 6; and
wherein the carbon atoms marked with an asterisk can have any stereochemical configuration.

In one embodiment of the compound of structure I, $R_6$ is H or =O. In another embodiment of the compound of structure I, Q is phenyl, substituted phenyl, naphthyl or substituted naphthyl.

In one embodiment of structure I, J is phenyl, substituted phenyl, naphthyl or substituted naphthyl; L is —$CH_2$— or —$(CH_2)_2$—; Q is phenyl, substituted phenyl, naphthyl or substituted naphthyl; W is H or phenyl, $R_6$ is H or =O; $R_7$ is $NH_2$, $NH-R_8$, or

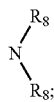

y is 0 if W is H, and otherwise y is 1; and z is 1 or 2.

In yet another embodiment of the compound of structure I, $R_7$ is $NH_2$, $N(CH_3)_2$, $NHCH_3$,

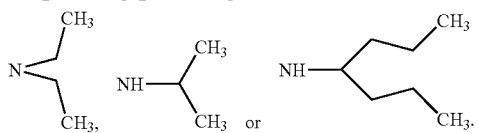

The amine capping group in structure I may be allyl, cyclopropane methyl, hexanoyl, heptanoyl, acetyl, propionoyl, butanoyl, phenyl acetyl, phenyl propinoyl, phenyl butanoyl, cyclohexylacetyl, naphthylacetyl, cinnamoyl, phenyl, benzyl, benzoyl, ring-substituted benzoyl, 4'-toluenesulfonyl, 4'-carboxy heptane, 12-Ado, 7'-amino heptanoyl, 6-Ahx, Amc, 8-Aoc, or polyethylene glycol with a formula molecular weight of between about 100 and about 10,000.

The natural or unnatural amino acid containing an aliphatic or aromatic side chain of structure I may be an L- or D-isomer of Phe, Phe(2-Cl), Phe(4-Cl), Phe(2,4-diCl), Phe(2,4-diF), Phe(3,4-diCl), Phe(4-$NO_2$), Phe(4-Me), Phe(4-Phenyl), HPhe, pF-Phe, Phe(4-Br), Phe(4-$CF_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-$CF_3$), Phe(3,4-di-OMe), Phg, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Lys(Z), Lys(Z-2'Br), Lys(Bz), Thr(Bzl), Tic, Tiq, Cys(Bzl), Tyr(2,6-DiCl-Bzl), Tyr(Bzl), Abu, 2-Abz, 3-Abz, 4-Abz, Achc, Acpc, Aib, Amb, Arg(Tos), Asp(anilino), Asp(3-Cl-anilino), Asp(3,5-diCl-anilino), 11-Aun, AVA, Beta-hHyp(Bzl), Cha, Chg, Cmpi, Disc, Dpr(beta-Ala), GAA, GBzA, B-Gpa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser(O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl), Thr(O-2-Cl-Phenyl), Nle, Leu, Ile, Val or Beta-Ala.

Thus in one embodiment, in the compound of structure I the group J is a substituted or unsubstituted ring group selected from the group consisting of:

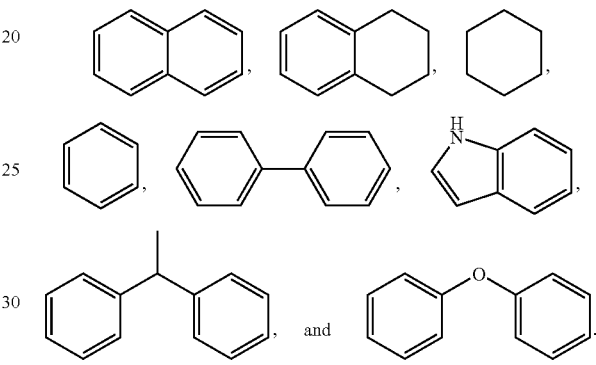

J may be substituted at one or more positions with one or more hydroxyl, halogen, alkyl or aryl groups.

In the compounds of structure I, Q may be:

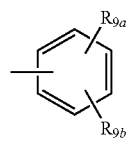

where $R_{9a}$ and $R_{9b}$ are optional ring substituents, and when one or both are present, are the same or different and independently hydroxyl, halogen, alkyl, or aryl groups attached directly or through an ether linkage.

In another embodiment, there is provided the compound of formula II, defined as set forth above:

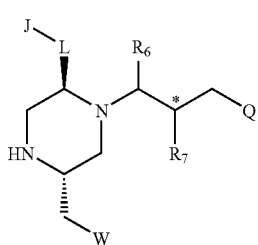

and pharmaceutically acceptable salts thereof.

In yet another embodiment, there is provided the compound of formula III, defined as set forth above:

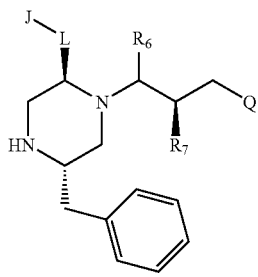

III and pharmaceutically acceptable salts thereof.

In yet another embodiment, there is provided the compound of formula IV, defined as set forth above:

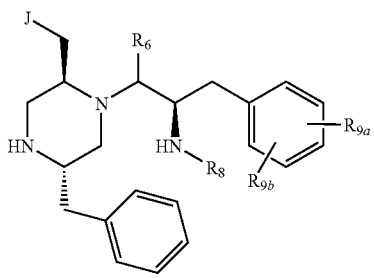

IV and pharmaceutically acceptable salts thereof, where J is phenyl, substituted phenyl, naphthyl or substituted naphthyl and where $R_{9a}$ and $R_{9b}$ are optional ring substituents, and when one or both are present, are the same or different and independently hydroxyl, halogen, alkyl, or aryl groups attached directly or through an ether linkage.

In yet another embodiment, there is provided the compound of formula V, defined as set forth above:

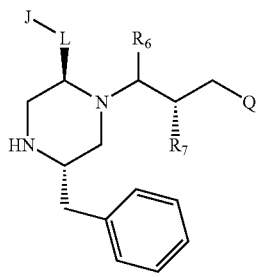

V and pharmaceutically acceptable salts thereof.

In yet another embodiment, there is provided the compound of formula VI, defined as set forth above:

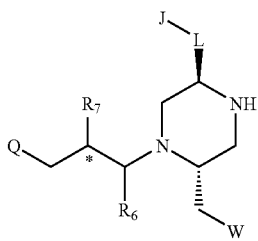

VI and pharmaceutically acceptable salts thereof.

In yet another embodiment, there is provided the compound of formula VII, defined as set forth above:

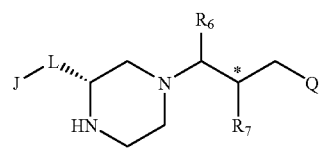

VII and pharmaceutically acceptable salts thereof.

In yet another embodiment, there is provided the compound of formula VIII, defined as set forth above:

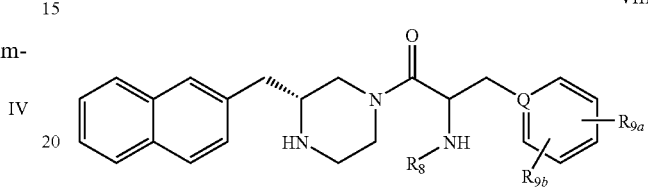

VIII and pharmaceutically acceptable salts thereof, where $R_{9a}$ and $R_{9b}$ are optional ring substituents, and when one or both are present, are the same or different and independently hydroxyl, halogen, alkyl, or aryl groups attached directly or through an ether linkage.

The compounds of any of formulas I to VIII are preferably specific for one or more of the melanocortin-1 receptor, melanocortin-3 receptor, melanocortin-4 receptor and melanocortin-5 receptor.

In an alternative embodiment, the invention provides a compound having the structure IX:

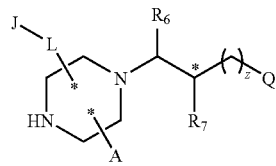

IX or an enantomeric, stereoisomeric or diastereomeric form of the foregoing, and pharmaceutically acceptable salts thereof; wherein J is a substituted or unsubstituted monocyclic or bicyclic ring structure, wherein in each instance the ring or rings have 5 or 6 ring atoms;

L is a bond or a linker selected from the group consisting of —(CH$_2$)$_q$—, —(CH$_2$)$_q$—O—, —(CH$_2$)$_q$—O—(C=O)—, —(CH$_2$)$_q$—NH—, —(CH$_2$)$_q$—NH—(C=O)—, —(CH$_2$)$_q$—(C=O)—, (CH$_2$)$_q$—(C=O)—NH— and —(CH$_2$)$_q$—(C=O)—O—;

A is a $C_1$ to $C_6$ linear or branched chain;

Q is a ring group comprising at least one aryl group;

$R_6$ is H, =O, =S or CH$_3$;

$R_7$ is H, NH$_2$, NH—$R_8$, or

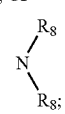

$R_8$ is a $C_1$ to $C_6$ linear or branched chain, an amine capping group, a natural or unnatural amino acid containing an aliphatic or aromatic side chain, or a natural or unnatural amino acid containing an aliphatic or aromatic side chain with a pendant amine capping group, and where there are two $R_8$ groups, each $R_8$ is independently a $C_1$ to $C_6$ linear or branched chain or an amine capping group, or one $R_8$ is a $C_1$ to $C_6$ linear or branched chain or an amine capping group and the remaining $R_8$ is a natural or unnatural amino acid containing an aliphatic or aromatic side chain or a natural or unnatural amino acid containing an aliphatic or aromatic side chain with a pendant amine capping group;

q is from 1 to 6;

y is from 0 to 6;

z is from 0 to 6; and wherein the carbon atoms marked with an asterisk can have any stereochemical configuration.

The compound of formula IX is preferably specific for one or more of the melanocortin-1 receptor, melanocortin-3 receptor, melanocortin-4 receptor and melanocortin-5 receptor.

The invention further provides a pharmaceutical composition for treatment of a melanocortin receptor-associated disorder, including a compound of any of formulas I to IX and a pharmaceutically acceptable carrier. A method for treatment of a melanocortin receptor-associated disorder is further provided, the method including the step of administration of a therapeutically effective amount of a pharmaceutical composition including a compound of any of formulas I to IX.

In another embodiment the present invention provides a compound that is an agonist of a melanocortin receptor, including MC1-R, MC3-R, MC4-R, or MC5-R. The compound can also be an antagonist of a melanocortin receptor, including MC1-R, MC3-R, MC4-R, or MC5-R.

The compound can also be an inverse agonist of a melanocortin receptor, including MC1-R, MC3-R, MC4-R, or MC5-R. The compound can also further be an antagonist of an inverse agonist of a melanocortin receptor, including MC1-R, MC3-R, MC4-R, or MC5-R.

The invention further includes a method for altering a disorder or condition associated with the activity of a melanocortin receptor, comprising administering to a patient a therapeutically effective amount a compound of this invention. In one embodiment the disorder or condition is an eating disorder such as cachexia. In another embodiment the disorder or condition is obesity and associated impairment of energy homeostasis. In yet another embodiment the disorder or condition is sexual dysfunction such as erectile dysfunction or female sexual dysfunction.

The invention further includes a method for altering a disorder or condition associated with the activity of a melanocortin receptor, comprising administering to a patient a therapeutically effective amount of a compound of this invention. In one embodiment the disorder or condition is an eating disorder such as cachexia. In another embodiment the disorder or condition is obesity and associated impairment of energy homeostasis. In yet another embodiment the disorder or condition is sexual dysfunction such as erectile dysfunction or female sexual dysfunction.

A primary object of the present invention is to provide a conformationally constrained isomer of a substituted piperazine, wherein the pendant group substituents are amino acid moieties, amino acid side chain moieties or derivatives thereof, such that the resulting ring compound mimics biologically a relevant reverse turn peptide structure.

Another primary object of the present invention is to provide a substituted piperazine wherein at least one unsubstituted ring nitrogen provides a cationic center available for receptor binding.

Another object of the present invention is to provide optically pure substituted piperazine compounds.

Another object of the present invention is to provide piperazine core compounds wherein pendant groups are provided, which pendant groups are or include amino acid side chain moieties.

Another object of the present invention is to provide a substituted piperazine compound wherein such compound is specific for one or more melanocortin receptors.

Another object of the present invention is to provide a method for synthesis of di-substituted and tri-substituted piperazine compounds of the invention.

Other objects, advantages and novel features, and the further scope of applicability of the present invention will be set forth in part in the detailed description to follow, and in part will become apparent to those skilled in the art upon examination of the following, or may be learned by practice of the invention.

DETAILED DESCRIPTION OF THE INVENTION

In this invention it is disclosed that piperazine rings may be employed with two or three descriptors, wherein each descriptor is a separate pendant group or substituent unique to a given ring atom. This invention thus discloses the use of substituted piperazine templates for drug design. The invention further also relates to enantiomerically pure substituted piperazine compounds, preferably made by the synthetic schemes disclosed herein or variants thereof. The piperazine compounds of the invention are characterized in that they have a single unsubstituted ring nitrogen. In a preferred embodiment, the piperazine compounds are further characterized in that the pendant groups or substituents do not include a heteroatom cationic center, such as a guanidine group. Prior art melanocortin receptor-specific piperazine or ketopiperazine compounds most generally include a substituent with a heteroatom cationic center group, such as the side chain of Arg or a side chain or mimetic or derivative thereof of an amino acid with a cationic center, or alternatively include a hydrogen bond donor or acceptor.

In one broad aspect, the invention describes and discloses the use of substituted piperazine compounds as biologically active agents. In a related aspect, the invention describes and discloses the use of substituted piperazine compounds as mimetics of desired pharmacophores.

In yet another embodiment, the invention describes substituted piperazine compounds specific for G-protein coupled receptor systems, such systems including, but not limited to, melanotropin or melanocortin receptors (MC1-R, MC3-R, MC4-R and MC5-R).

In yet another embodiment, the invention provides novel schemes and methods of synthesis of substituted piperazine compounds.

DEFINITIONS

Before proceeding further with the description of the invention, certain terms are defined as set forth herein.

The "amino acid" and "amino acids" used in this invention, and the terms as used in the specification and claims, include the known naturally occurring protein amino acids, which are referred to by both their common three letter abbreviation and single letter abbreviation. See generally *Synthetic Peptides: A*

*User's Guide*, G A Grant, editor, W.H. Freeman & Co., New York, 1992, the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like, collectively referred to herein as "unnatural amino acids." Modified and unusual amino acids are described generally in *Synthetic Peptides: A User's Guide*, cited above; Hruby V J, Al-obeidi F and Kazmierski W: *Biochem J* 268:249-262, 1990; and Toniolo C: *Int J Peptide Protein Res* 35:287-300, 1990; the teachings of all of which are incorporated herein by reference.

The term "amino acid side chain moiety" used in this invention includes any side chain of any amino acid, as the term "amino acid" is defined herein, including any derivative of an amino acid side chain moiety, as the term "derivative" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, and saturated or unsaturated alkyl, aryl or aralkyl moieties.

The following abbreviations for amino acids, amino acid side chain moieties and derivatives thereof have the meanings given, it being understood that any amino acid may be in either the L- or D-configuration:

Abu—gamma-amino butyric acid

2-Abz—2-amino benzoic acid

3-Abz—3-amino benzoic acid

4-Abz—4-amino benzoic acid

Achc—1-amino-cyclohexane-1-carboxylic acid

Acpc—1-amino-cyclopropane-1-carboxylic acid

12-Ado—12-amino dodecanoic acid

Aib—alpha-aminoisobutyric acid

Aic—2-aminoindane-2-carboxylic acid

6-Ahx—6-amino hexanoic acid

Amb—4-(aminomethyl)-benzoic acid

Amc—4-(aminomethyl)-cyclohexane carboxylic acid

7'-amino-heptanoyl—$NH_2$—$(CH_2)_6CO$—

8-Aoc—8-amino octanoic acid

Arg(Tos)—$N^G$-para-tosyl-arginine

Asp(anilino)—beta-anilino-aspartic acid

Asp(3-Cl-anilino)—beta-(3-chloro-anilino)-aspartic acid

Asp(3,5-diCl-anilino)—beta-(3,5-dichloro anilino)-aspartic acid

Atc—2-aminotetralin-2-carboxylic acid

11-Aun—11-amino undecanoic acid

AVA—5-amino valeric acid

Beta-h Hyp(Bzl)—Beta-(O-benzyl)-homohydroxyproline

Beta-hSer(Bzl)—Beta-(O-benzyl)-homoserine

Bip—biphenylalanine

Cha—cyclohexylalanine

Chg—cyclohexylglycine

Cmpi—4-caboxymethyl-piperazine

Dip—3,3-diphenylalanine

Disc—1,3-dihydro-2H-isoindolecarboxylic acid

Dpr(beta-Ala)—$N_{beta}$-(3-aminopropionyl)-alpha, beta-diaminopropionic acid

GAA—epsilon-guanidino acetic acid

GBzA—4-guanidino benzoic acid

B-Gpa—3-guanidino propionic acid

GVA(Cl)—beta-chloro-epsilon-guanidino valeric acid

Heptanoyl—$CH_3$—$(CH_2)_5CO$— hPhe—homophenylalanine hSer—homoserine

Hyp—hydroxy proline hHyp—homo hydroxy proline

Hyp(Bzl)—O-benzyl-hydroxyproline

Hyp(2-naphthly)—O-2' naphthyl-hydroxyproline

Hyp(Phenyl)—phenyl-hydroxyproline

Idc—indoline-2-carboxylic acid

Igl—indanylglycine

Inp—isonipecotic acid

Lys(Z)—N-epsilon-benzyloxycarbonyl-lysine

Nal 1—3-(1-naphthyl)alanine

Nal 2—3-(2-naphthyl)alanine (N-Bzl)Nal 2—N-benzyl-3-(2-naphthyl)alanine

2-Naphthylacetyl—2-naphthyl-$CH_2CO$—

(Nlys)Gly—N-(4-aminobutyl)-glycine (N-PhEt)Nal 2—N(2-phenylethyl)-3-(2-naphthyl)alanine OcHx—cyclohexyl ester Phg—phenylglycine pF-Phe—para-fluoro-phenylalanine Phe(4-Br)—4-bromo-phenylalanine Phe(4-$CF_3$)—4-trifluoromethyl-phenylalanine Phe(4-Cl)—4-chloro-phenylalanine Phe(3-Cl)—3-chloro-phenylalanine Phe(2-Cl)—2-chloro-phenylalanine Phe(2,4-diCl)—2,4,-dichloro-phenylalanine Phe(2,4-diF)—2,4-difluoro-phenylalanine Phe(3,4-diCl)—3,4,-dichloro-phenylalanine Phe(5-Cl)—5-chloro-phenylalanine Phe(3,4-diF)—3,4,-difluoro-phenylalanine Phe(4-I)—4-iodo-phenylalanine Phe(3,4-di-OMe)—3,4,-dimethoxy-phenylalanine Phe(4-Me)—4-methyl-phenylalanine Phe(4-OMe)—4-methoxy-phenylalanine Phe(4-NC)—4-cyano-phenylalanine Phe(4-NO$_2$)—4-nitro-phenylalanine Pip—pipecolic acid 3-Pya—3-pyridylalanine Pyr—pyroglutamic acid Qal(2')—beta-(2-quinolyl)-alanine Sal—3-styrylalanine Sar—sarcosine Ser(Bzl)—O-benzyl-serine Ser(2-Naphthyl)—O-2-Naphthyl-serine Ser(Phenyl)—O-2-Phenyl-serine Ser(4-Cl-Phenyl)—O-4-Cl-Phenyl-serine Ser(2-Cl-Phenyl)—O-2-Cl-Phenyl-serine Ser(p-Cl-Bzl)—O-4-Cl-Benzyl-serine Thr(Bzl)-O-Benzyl-threonine Tic—1,2,3,4-tetrahydroisoquinoline-3-carboxylic acid Tiq—1,2,3,4-tetrahydroisoquinoline-1-carboxylic acid Tle—tert-butylalanine Tpi—1,2,3,4-tetrahydronorharman-3-carboxylic acid Tyr(Bzl)—O-benzyl-tyrosine Tyr(2,6-DiCl-Bzl)—O-(2,6 dichloro)benzyl-tyrosine In the listing of compounds according to the present invention, conventional amino acid residues have their conventional meaning as given in Chapter 2400 of the *Manual of Patent Examining Procedure*, 7$^{th}$ Ed. Thus, "Nle" is norleucine; "Asp" is aspartic acid; "His" is histidine; "D-Phe" is D-phenylalanine; "Arg" is arginine; "Trp" is tryptophan; "Lys" is lysine; "Gly" is glycine; "Pro" is proline; "Tyr" is tyrosine, "Ser" is serine and so on.

The following amino acids, or side chains thereof, may be employed, in either the L- or D-configuration as appropriate, in certain embodiments of this invention:

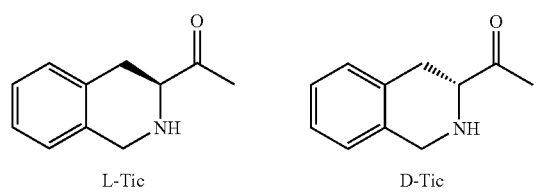

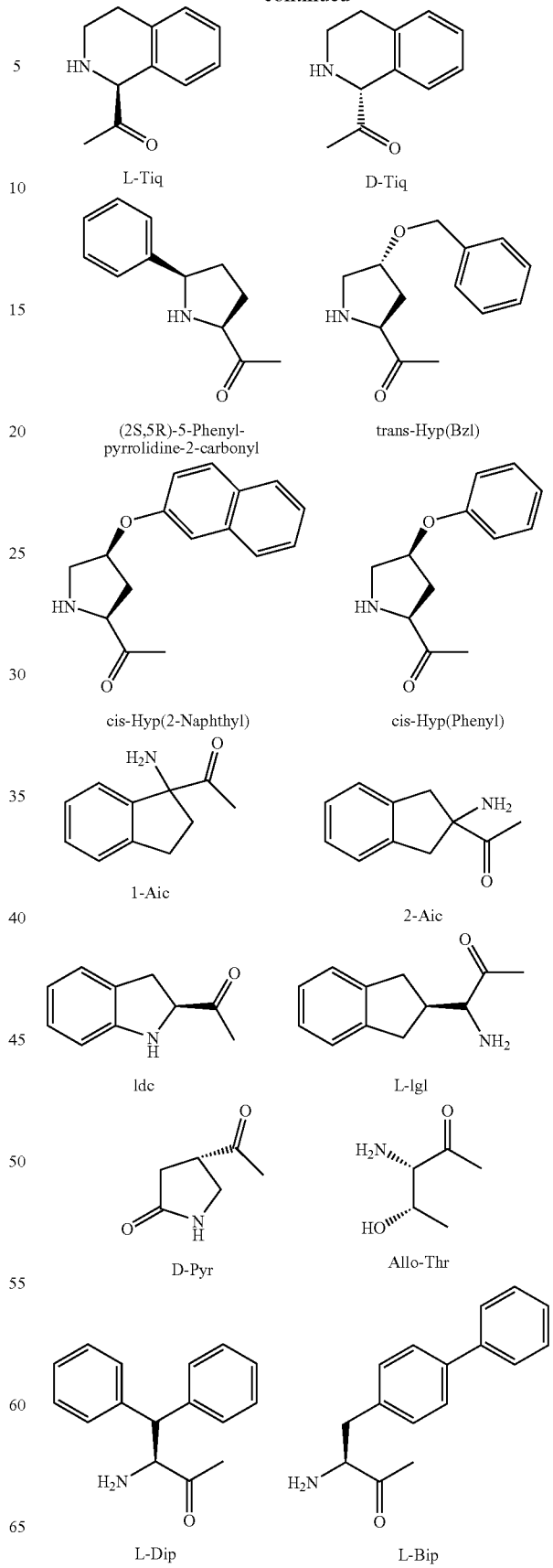

-continued

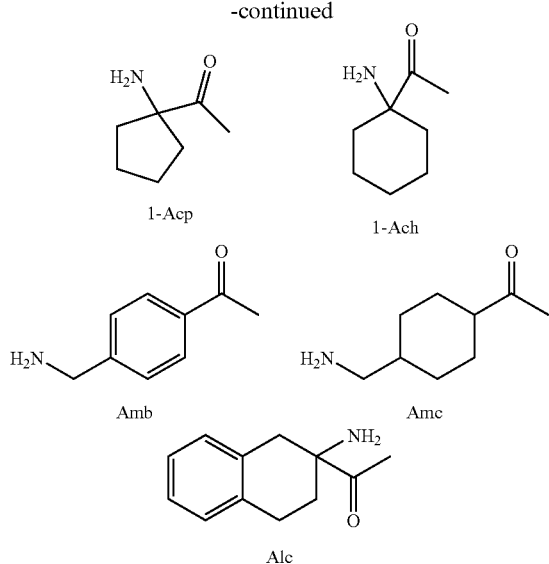

1-Acp

1-Ach

Amb

Amc

Alc

In the specification and the claims, the term "homolog" includes, without limitation, (a) a D-amino acid residue or side chain substituted for an L-amino acid residue side chain, (b) a post-translationally modified residue or side chain substituted for the residue or side chain, (c) a non-protein or other modified amino acid residue or side chain based on another such residue or side chain, such as phenylglycine, homophenylalanine, ring-substituted halogenated, alkylated or arylated phenylalanines for a phenylalanine residue, diamino proionic acid, diamino butyric acid, ornithine, lysine and homoarginine for an arginine residue, and the like, and (d) any amino acid residue or side chain, coded or otherwise, or a construct or structure that mimics an amino acid residue or side chain, and which has at least a similarly charged side chain (neutral, positive or negative), preferably a similar hydrophobicity or hydrophilicity, and preferably a similar side chain in terms of being a saturated aliphatic side chain, a functionalized aliphatic side chain, an aromatic side chain or a heteroaromatic side chain.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxy-carbonyl. Examples of an aryl group include phenyl, biphenyl, naphthyl, 1-naphthyl, and 2-naphthyl, derivatives thereof, and the like.

The term "aralkyl" includes a radical —$R^a R^b$ where $R^a$ is an alkylene (a bivalent alkyl) group and $R^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group $CH_3CO$—.

A group or aliphatic moiety is "acylated" when an alkyl or substituted alkyl group as defined above is bonded through one or more carbonyl [—(C=O)—] groups.

An "omega amino derivative" includes an aliphatic moiety with a terminal amino group. Examples of omega amino derivatives include aminoheptanoyl and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—$CO.NH_2$), such as methylamide, ethylamide, propylamide, and the like.

An "imide" includes compounds containing an imido group (—CO.NH.CO—).

An "amine" includes compounds that contain an amino group (—$NH_2$).

A "nitrile" includes compounds that are carboxylic acid derivatives and contain a (—CN) group bound to an organic group.

An amino acid side chain moiety is "hydrogen bonding" when the side chain includes hydrogen donors or alternatively hydrogen acceptors.

An "amine capping group" includes any terminal group attached through a terminal amine, including but not limited to any omega amino derivative, acyl group or terminal aryl or aralkyl, including groups such as allyl, cyclopropane methyl, hexanoyl, heptanoyl, acetyl, propionoyl, butanoyl, phenyl acetyl, phenyl propinoyl, phenyl butanoyl, cyclohexylacetyl, naphthylacetyl, cinnamoyl, phenyl, benzyl, benzoyl, ring-substituted benzoyl, 4'-toluenesulfonyl, 4'-carboxy heptane, 12-Ado, 7'-amino heptanoyl, 6-Ahx, Amc, 8-Aoc, or polyethylene glycol with a formula molecular weight of between about 100 and about 10,000.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and one or more pharmaceutically acceptable carriers, and optionally one or more pharmaceutically active ingredients and agents.

A variety of chemicals and compounds are employed in this invention, and the following abbreviations have the meanings given:

AcOH acetic acid
Bzl benzyl
Bz benzoyl
Boc tertiary butyloxycarbonyl
Cbz benzyloxycarbonyl
DCM dichloromethane
DEAD diethyl azodicarboxylate
DIC 1,3-diisopropylcarbodiimide
DIAD diisopropyl azodicarboxylate
DMF N,N-dimethylformamide
DMSO dimethyl sulfoxide
EDC N-(3-dimethylaminopropyl)-N'-ethylcarbodiimide hydrochloride
Et- ethyl
EtOAc ethyl acetate
EtNH ethylnolamine
$Et_2NH$ diethylamine
Fmoc 9-fluorenylmethoxycarbonyl
HEPES 4-(2-hydroxyethyl)1-piperazineethanesulfonic acid
HOAt 1-hydroxy-7-azabenzotriazole
HOBt 1-hydroxybenzotriazole
$KHSO_4$ potassium sulphate
IBCF isobutyl chloroformate
LAH lithium aluminum hydride
Me methyl
$NaBH(OAc_3)$ sodium triacetoxy borohydride
NMM N-methyl-morpholine
NMP 1-methyl-2-pyrrolidinone
Pr propyl
Pr-i isopropyl
TBTU 2-(1H-Benzotriazole-1-yl)-1,1,3,3-tetramethyluronium tetrafluoroborate
TEA triethylamine
TFA trifluoroacetic acid
THF tetrahydrofuran
TPP triphenylphosphine ($Ph_3P$)

In one embodiment, a "di-substituted piperazine", as used herein, is a piperazine compound or derivative thereof wherein groups other than solely H, O, S or a halogen, and preferably including an amino acid residue or an amino acid side chain moiety, are attached to two individual ring C members.

In another embodiment, a "di-substituted piperazine", as used herein, is a piperazine compound or derivative thereof wherein a group other than solely H, and preferably including an amino acid residue or an amino acid side chain moiety, is attached to one ring N member, and a group other than solely H, O, S or a halogen, preferably including an amino acid side chain moiety, is attached to one ring C member.

A "tri-substituted piperazine", as used herein, is a piperazine compound or derivative thereof wherein a group other than solely H, and preferably including an amino acid residue or an amino acid side chain moiety, is attached to one ring N member, and the groups other than solely H, O, S or a halogen, preferably including an amino acid side chain moiety, are attached to two individual ring C members.

"Sexual dysfunction" means any condition that inhibits or impairs normal sexual function, including coitus. The term is not limited to physiological conditions, and includes psychogenic conditions or perceived impairment without a formal diagnosis of pathology or disorder. Sexual dysfunction includes erectile dysfunction in a male mammal and female sexual dysfunction in a female mammal.

"Erectile dysfunction" is a disorder involving the failure of a male mammal to achieve functional erection, ejaculation, or both. Erectile dysfunction is accordingly synonymous with impotence, and includes the inability to attain or sustain an erection of sufficient rigidity for coitus. Symptoms of erectile dysfunction include an inability to achieve or maintain an erection, ejaculatory failure, premature ejaculation, or inability to achieve an orgasm. An increase in erectile dysfunction is often associated with age or may be caused by a physical disease or as a side-effect of drug treatment.

"Female sexual dysfunction" is a disorder including sexual arousal disorder. The term "sexual arousal disorder" includes a persistent or recurrent failure to attain or maintain the lubrication-swelling response of sexual excitement until completion of sexual activity. Sexual dysfunction in females can also include inhibited orgasm and dyspareunia, which is painful or difficult coitus. Female sexual dysfunction includes, but is not limited to, a number of categories of diseases, conditions and disorders including hypoactive sexual desire disorder, sexual anhedonia, sexual arousal disorder, dyspareunia and vaginismus. Hypoactive sexual desire disorder includes a disorder in which sexual fantasies and desire for sexual activity are persistently or recurrently diminished or absent, causing marked distress or interpersonal difficulties. Hypoactive sexual desire disorder can be caused by boredom or unhappiness in a long-standing relationship, depression, dependence on alcohol or psychoactive drugs, side effects from prescription drugs, or hormonal deficiencies. Sexual anhedonia includes decreased or absent pleasure in sexual activity. Sexual anhedonia can be caused by depression, drugs, or interpersonal factors. Sexual arousal disorder can be caused by reduced estrogen, illness, or treatment with diuretics, antihistamines, antidepressants, or antihypertensive agents. Dyspareunia and vaginismus are sexual pain disorders characterized by pain resulting from penetration and may be caused, for example, by medications which reduce lubrication, endometriosis, pelvic inflammatory disease, inflammatory bowel disease or urinary tract problems.

By a melanocortin receptor "agonist" is meant an endogenous or drug substance or compound, including a compound of this invention, which can interact with a melanocortin receptor and initiate a pharmacological response characteristic of the melanocortin receptor. By a melanocortin receptor "antagonist" is meant a drug or a compound, including a compound of this invention, that opposes the melanocortin receptor-associated responses normally induced by a melanocortin receptor agonist agent.

By "binding affinity" is meant the ability of a compound or drug to bind to its biological target.

Clinical Applications. The compounds disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

Melanocortin receptor-specific compounds of this invention that are MC1-R specific can be used as chemoprevention agents against sun-induced, such as by UV radiation, neoplastic activity in human skin. MC1-R agonist compounds of this invention may be employed to stimulate epidermal melanocytes to produce melanin as well as to convert pheomelanin to eumelanin. Eumelanin, which is dark brown or black pigmentation, is considered more photo-protective than pheomelanin, which is yellow or red pigmentation. The process of melanogenesis is believed to involve stimulation of MC1-R in epidermal melanocytes, thereby mediating the stimulation of tyrosinase enzymes within these pigment cells, inducing the conversion of tyrosine to dopa and then through dopaquinone to eumelanin. Sun tanning due to direct sun exposure is proposed to result from the same pathway by local production of melanotropic peptide from a POMC gene in the epidermis. Thus stimulation of eumelanin production and conversion of pheomelanin to eumelanin may be a desirable chemoprevention modality in blocking sun- or UV-induced neoplastic activity in skin. A potent, high-affinity and highly selective MC1-R agonist compound of this invention can accordingly be used as a therapeutic chemoprevention agent for combating harmful sun or UV exposure that induces neoplastic activity in skin melanocytes.

In another embodiment, compounds of this invention that are MC4-R agonists can be used as a therapeutic agent to modify energy metabolism and feeding behavior, including treatment of pathologic obesity and related conditions. Compounds of this invention that are MC4-R antagonists can also be used as a therapeutic agent in eating disorders, such as treatment of anorexia and cachexia, which is malnutrition and wasting due to illness. Control centers for eating and satiety reside in the hypothalamus. These responses are determined by diverse hormones and soluble factors that signal through specific receptors in the hypothalamus. MC4-R is known to be expressed in the brain, and inactivation of this receptor by gene targeting has resulted in mice with a maturity-onset obesity syndrome associated with hyperphagia, hyperinsulinemia and hyperglycemia.

In yet another embodiment, compounds of this invention can be used as therapeutic agents for treatment of sexual dysfunction, including treatment of both male erectile dysfunction and female sexual dysfunction.

In yet another embodiment, compounds of this invention may be used as therapeutic agents for treatment of inflammation, including specifically MC1-R, MC3-R and MC5-R agonists.

In yet another embodiment of the invention, compounds of this invention that are MC5-R specific can be used as agents to decrease sebum production, and thus may be efficacious in the treatment of acne and related diseases. The compounds for this application may be conveniently formulated for local administration, as through a gel, lotion, cream or other topical formulation.

The compounds may be formulated by any means known in the art, including but not limited to tablets, capsules, caplets, suspensions, powders, lyophilized forms and aerosols and may be mixed and formulated with buffers, binders, stabilizers, anti-oxidants and other agents known in the art. The compounds may be administered by any systemic or partially systemic means known in the art, including but not limited to intravenous injection, subcutaneous injection, administration through mucous membranes, oral administration, dermal administration, skin patches, aerosols and the like.

The invention further provides a pharmaceutical composition that includes a compound of this invention and a pharmaceutically acceptable carrier. The compound of this invention may thus be formulated or compounded into pharmaceutical compositions that include at least one compound of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, mannitol, sodium chloride or sodium citrate. For injection or other liquid administration formulations, water containing at least one or more buffering constituents is suitable, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, such that the dosage may be formulated so as to effect delivery of a compound of this invention over a period of time.

The compounds of this invention may be in the form of any pharmaceutically acceptable salt. Acid addition salts of the compounds of this invention are prepared in a suitable solvent from the compound and an excess of an acid, such as hydrochloric, hydrobromic, sulfuric, phosphoric, acetic, trifluoroacetic, maleic, succinic or methanesulfonic. The acetate salt form is especially useful. Where the compounds of this invention include an acidic moiety, suitable pharmaceutically acceptable salts may include alkali metal salts, such as sodium or potassium salts, or alkaline earth metal salts, such as calcium or magnesium salts.

The compounds and pharmaceutical compositions of this invention may be administered by injection, which injection may be intravenous, subcutaneous, intramuscular, intraperitoneal or by any other means known in the art. In general, any route of administration by which the compounds of this invention are introduced across an epidermal layer of cells may be employed. Administration means may include administration through mucous membranes, buccal administration, oral administration, dermal administration, inhalation administration, nasal administration and the like. The dosage for treatment is administration, by any of the foregoing means or any other means known in the art, of an amount sufficient to bring about the desired therapeutic effect.

Therapeutically Effective Amount. In general, the actual quantity of compound of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. This may readily be determined by one of ordinary skill in the art through means such as pharmacokinetic studies, plasma half-life studies, dose escalation studies, and the like. Thus a therapeutically effective amount includes an amount of a compound or pharmaceutical composition of this invention that is sufficient to induce the desired therapeutic effect.

In general, the compounds of this invention are highly active, with dose responses as low as 0.01 µg/kg, generally with optimal or peak dose responses between about 0.01 µg/kg and 25 µg/kg, depending on the specific compound and the route of administration. For example, the compound can be administered at 0.01, 0.05, 0.1, 0.5, 1, 5, 10, 50, 100, or 500 µg/kg body weight, depending on specific compound selected, the desired therapeutic response, the route of administration, the formulation and other factors known to those of skill in the art. Conventional dose response studies and other pharmacological means may be employed to determine the optimal dose for a desired effect with a given compound, given formulation and given route of administration.

Combination Therapy and Sexual Dysfunction. It is also possible and contemplated to use the compounds of this invention in combination with other drugs or agents for treatment of sexual dysfunction. These other drugs and agents may include melanocortin receptor-specific agents that induce erectile activity, including specifically MC3-R and MC4-R agonists, phosphodiesterase-5 inhibitors, testosterone, prostaglandin and the like. In a preferred embodiment of the invention, compounds of the invention are used in combination with a therapeutically effective amount of a cyclic-GMP-specific phosphodiesterase inhibitor or an alpha-adrenergic receptor antagonist. Similarly, the compounds of this invention may be used in combination with any known mechanical aids or devices.

The present invention thus provides methods of treating sexual dysfunction, the methods comprising the step of administering to the patient having or at risk of having sexual dysfunction a therapeutically effective amount of a compound of this invention in combination with a therapeutically effective amount of a second sexual dysfunction pharmaceutical agent. The compound of this invention may be administered simultaneously with, prior to or subsequent to administration with a therapeutically effective amount of a second sexual dysfunction pharmaceutical agent. Preferably the compound of this invention is administered within one hour, preferably within less than one-half hour, of administration of a therapeutically effective amount of a second sexual dysfunction pharmaceutical agent. However, for certain forms of combination therapy, such as for example in combination with a therapeutically effective amount of a hormone or hormone-related sexual dysfunction pharmaceutical agent, the hormone or hormone-related sexual dysfunction pharmaceutical agent may be administered on an independent schedule, such that there is no set or specific temporal relationship between administration of the compound of this invention and the hormone or hormone-related sexual dysfunction pharmaceutical agent. Thus, for example, the hormone or hormone-related sexual dysfunction pharmaceutical agent may be administered on a daily or other dose, or by means of patches or other continuous administration schedules, with administration of the compound of this invention when desired or needed by the patient.

The present invention also provides pharmaceutical compositions that comprise 1) a compound of this invention and 2) a second compound useful for the treatment of sexual dysfunction. The present invention further provides pharmaceutical compositions that comprise 1) a compound of this invention and 2) a second compound useful for the treatment of sexual dysfunction.

In an embodiment of the composition above, the additional compounds useful for the treatment of sexual dysfunction are preferably selected from but not limited to the group consisting of a phosphodiesterase inhibitor; a cyclic-GMP-specific phosphodiesterase inhibitor; prostaglandins; apomorphin; oxytocin modulators; a-adrenergic antagonists; dopaminergic ligands; androgens; selective androgen receptor modulators (SARMs); buprorion; vasoactive intestinal peptide (VIP); neutral endopeptidase inhibitors (NEP); neuropeptide Y receptor antagonists (NPY); and bombesin receptor-3 antagonists.

Thus the second sexual dysfunction pharmaceutical agent may be a type V phosphodiesterase inhibitor (PDE-5). For example, the PDE-5 inhibitor may be Viagra®, a brand of sildenafil, Levitra®, or Cialis®.

In another embodiment of the composition above, the compound useful for the treatment of sexual dysfunction is an estrogen agonist/antagonist. In one embodiment, the estrogen agonist/antagonist is lasofoxifene or an optical or geometric isomer thereof; a pharmaceutically acceptable salt, N-oxide, ester, quaternary ammonium salt; or a prodrug thereof. More preferably, the estrogen agonist/antagonist is in the form of a D-tartrate salt.

In yet another embodiment of the composition above, the estrogen agonist/antagonist is selected from the group consisting of tamoxifen, 4-hydroxy tamoxifen, raloxifene, droloxifene, toremifene, centchroman, idoxifene, and the like, as well as and optical or geometric isomers thereof; and pharmaceutically acceptable salts, N-oxides, esters, quaternary ammonium salts, and prodrugs thereof.

In yet another embodiment, a compound of this invention may be used in combination with any known mechanical aids or devices.

The present invention also provides kits for the treatment of sexual dysfunction (including erectile dysfunction), the kits comprising: a first pharmaceutical composition including a compound of this invention; a second pharmaceutical composition comprising a second compound useful for the treatment of sexual dysfunction; and, a container for the first and second compositions.

Female Sexual Dysfunction. The compounds of this invention may be used to treat female sexual dysfunction as well as male sexual dysfunction. In general, the dosing schedules and doses for females are comparable to those for males.

Combination Therapy and Weight Regulation. It is also possible and contemplated to use compounds of this invention in combination with other drugs or agents for treatment of various weight and feeding-related disorders. Where the compound is an agonist or partial agonist, the compound may be employed for decreasing food intake and/or body weight in combination with any other agent or drug heretofore employed as a diet aid, or for decreasing food intake and/or body weight. Where the compound is an antagonist, the compound may be employed for increasing food intake and/or body weight in combination with any other agent or drug heretofore employed for increasing food intake and/or body weight.

Drugs that reduce energy intake include, in part, various pharmacological agents, referred to as anorectic drugs, which are used as adjuncts to behavioral therapy in weight reduction programs. Classes of anorectic drugs include, but are not limited to, noradrenergic and serotonergic agents. Noradrenergic medications may be described as those medications generally preserving the anorectic effects of amphetamines but with weaker stimulant activity. The noradrenergic drugs, except phenylpropanolamine, generally act through a centrally mediated pathway in the hypothalamus that causes anorexia. Phenylpropanolamine, a racemic mixture of norephedrine esters, causes a release of norepinephrine throughout the body and stimulates hypothalamic adrenoreceptors to reduce appetite.

Suitable noradrenergic agents include, but are not limited to, diethylpropion such as TENUATE™ (1-propanone, 2-(diethylamino)-1-phenyl-, hydrochloride) commercially available from Merrell; mazindol (or 5-(p-chlorophenyl)-2,5-dihydro-3H-imidazo[2,1-a]isoindol-5-ol) such as SANOREX™ commercially available from Novartis or MAZANOR™ commercially available from Wyeth Ayerst; phenylpropanolamine (or Benzenemethanol, alpha-(1-aminoethyl)-, hydrochloride); phentermine (or Phenol, 3-[[4,5- duhydro-1H-imidazol-2-yl)ethyl](4-methylphenyl)amino], monohydrochloride) such as ADIPEX-P™ commercially available from Lemmon, FASTIN™ commercially available from Smith-Kline Beecham and Ionamin™ commercially available from Medeva; phendimetrazine (or (2S,3S)-3,4-Dimethyl-2-phenylmorpholine L-(+)-tartrate (1:1)) such as METRA™ commercially available from Forest, PLEGINE™ commercially available from Wyeth-Ayerst; PRELU-2™ commercially available from Boehringer Ingelheim, and STATOBEX™ commercially available from Lemmon; phendamine tartrate such as THEPHORIN™ (2,3,4,9-Tetrahydro-2-methyl-9-phenyl-1H-indenol[2,1-c]pyridine L-(+)-tartrate (1:1)) commercially available from Hoffmann-LaRoche; methamphetamine such as DESOXYN™ Tablets ((S)—N, (alpha)-dimethylbenzeneethanamine hydrochloride) commercially available from Abbott; and phendimetrazine tartrate such as BONTRIL™ Slow-Release Capsules (-3,4-Dimethyl-2-phenylmorpholine Tartrate) commercially available from Amarin.

Suitable non-limiting serotonergic agents include sibutramine such as MERIDIA™ capsules (a racemic mixture of the (+) and (−) enantiomers of cyclobutanemethanamine, 1-(4-chlorophenyl)-N,N-dimethyl-(alpha)-(2-methylpropyl)-, hydrochloride, monohydrate) commercially available from Knoll, fenfluramine such as Pondimin™ (Benzeneethanamine, N-ethyl-alpha-methyl-3-(trifluoromethyl)-, hydrochloride) commercially available from Robbins; dexfenfluramine such as Redux™ (Benzeneethanamine, N-ethyl-alpha-methyl-3-(trifluoromethyl)-, hydrochloride) commercially available from Interneuron. Fenfluramine and dexfenfluramine stimulate release of serotonin and inhibit its reuptake. Sibutramine inhibits the reuptake of serotonin, norepinephrine and dopamine, but does not stimulate secretion of serotonin.

Other serotonergic agents useful with the practice of the present invention include, but are not limited to, certain auoretic gene 5HT1a inhibitors (brain, serotonin) such as carbidopa and benserazide as disclosed by U.S. Pat. No. 6,207,699 which is incorporated herein by reference; and certain neurokinin 1 receptor antagonist and selective serotonin reuptake inhibitors including fluoxetine, fluvoxamine, paroxtine, sertraline and other useful compounds as disclosed by U.S. Pat. No. 6,162,805 which is incorporated herein by reference. Other potential inhibitors that may be employed include 5HT2c inhibitors.

Other useful compounds for reducing energy intake include, but are not limited to, certain aryl-substituted cyclobutylalkylamines as disclosed by U.S. Pat. No. 6,127,424 which is incorporated herein by reference; certain trifluoromethylthiophenylethylamine derivatives as disclosed by U.S. Pat. No. 4,148,923 which is incorporated herein by reference; certain compounds as disclosed by U.S. Pat. No. 6,207,699 which is incorporated herein by reference; certain kainite or AMPA receptor antagonists as disclosed by U.S. Pat. No. 6,191,117 which is incorporated herein by reference; certain neuropeptide receptor subtype 5 as disclosed by U.S. Pat. No. 6,140,354 which is incorporated herein by reference; and certain alpha-blocking agents as disclosed by U.S. Pat. No. 4,239,763 which is incorporated herein by reference.

Moreover, several peptides and hormones regulate feeding behavior. For example, cholecystokinin and serotonin act to decrease appetite and food intake. Leptin, a hormone produced by fat cells, controls food intake and energy expenditure. In obese persons who are losing weight without medications, a decrease in weight is associated with a decrease in circulating levels of leptin, suggesting its role in weight homeostasis. Obese patients with high leptin levels are thought to have peripheral leptin resistance secondary to the down-regulation of leptin receptors. Non-limiting examples of useful compounds affecting feeding behavior include certain leptin-lipolysis stimulated receptors as disclosed by WO 01/21647 which is incorporated herein by reference; certain phosphodiesterase enzyme inhibitors as disclosed by WO 01/35970 which is incorporated herein by reference; certain compounds having nucleotide sequences of the mahogany gene as disclosed by WO 00/05373 which is incorporated herein by reference; and certain sapogenin compounds as disclosed by U.S. Pat. No. 4,680,289 which is incorporated herein by reference.

Other useful compounds include certain gamma peroxisome proliferator activated receptor (PPAR) agonists as disclosed by WO 01/30343 and U.S. Pat. No. 6,033,656 which are incorporated herein by reference, and certain polypeptides such as fibroblast growth factor-10 polypeptides as disclosed by WO 01/18210 which is incorporated herein by reference.

Moreover, monoamine oxidase inhibitors that decrease energy intake or increase energy expenditure are useful with the practice of the present invention. Suitable, but non-limiting examples of monoamine oxidase inhibitors include befloxatone, moclobemide, brofaromine, phenoxathine, esuprone, befol, toloxatone, pirlindol, amiflamine, sercloremine, bazinaprine, lazabemide, milacemide, caroxazone and other certain compounds as disclosed by WO 01/12176 which is incorporated herein by reference.

Certain compounds that increase lipid metabolism are also useful with the practice of the present invention. Such compounds include, but are not limited to, useful evodiamine compounds as disclosed by U.S. Pat. No. 6,214,831 which is incorporated herein by reference.

Nutrient partitioning agents and digestive inhibitors are another strategy in the treatment of obesity by interfering with the breakdown, digestion or absorption of dietary fat in the gastrointestinal tract. Gastric and pancreatic lipases aid in the digestion of dietary triglycerides by forming them into free fatty acids that are then absorbed in the small intestine. Inhibition of these enzymes leads to inhibition of the digestion of dietary triglycerides. Non-limiting examples include a lipase inhibitor, orlistat, such as XENICAL™ capsules ((S)-2-formylamino-4-methyl-pentanoic acid (S)-1-[[(2S,3S)-3-hexyl-4-oxo-2-oxetanyl]methyl]-dodecyl ester) commercially available from Roche Laboratories and certain benzoxazinone compounds as described by WO 00/40247 which is incorporated herein by reference.

Agents that increase energy expenditure are also referred to as thermogenic medications. Non-limiting examples of suitable thermogenic medications include xanthines, such as caffeine and theophylline, selective β-3-adrenergic agonists, for example certain compounds in U.S. Pat. No. 4,626,549 which is incorporated by reference herein, and α-2-adrenergic and growth hormones compounds as described in U.S. Pat. Nos. 4,937,267 and 5,120,713 which are incorporated by reference herein.

Generally, a total dosage of the above-described obesity control agents or medications, when used in combination with a compound of this invention can range from 0.1 to 3,000 mg/day, preferably from about 1 to 1,000 mg/day and more preferably from about 1 to 200 mg/day in single or 2-4 divided doses. The exact dose, however, is determined by the attending clinician and is dependent on such factors as the potency of the compound administered, the age, weight, condition and response of the patient.

Agents or drugs employed for increasing food intake and/or body weight include appetite stimulants such as megastrol acetate, adrenocorticoids such as prednisolone and dexamethasone, cyproheptidine, serotonergic drugs such as fenfluramine, neuropeptide Y, and androgen antagonists such as flutamide, nilutamide, and zanoterone.

Synthetic Methods of the Invention.

One general strategy includes developing a linear intermediate using chiral building blocks such as amino acid derivatives. The linear intermediate can be cyclized using a Mitsunobo reaction strategy or by spontaneous cyclization through reactive groups such as a reaction between an amine and an ester or between an amine and an aldehyde function. In these cyclizations, the driving force for intramolecular reaction versus intermolecular reaction is the thermodynamically favored reaction forming a six-membered ring structure. In many instances, the methodology incorporates conditions that do not involve inversion or racemization of chiral centers. In some instances where a small percentage of racemate is observed, such as in use of an α-amino aldehyde in the substituent containing Q, the desired chiral product is easily purified by methods known in the art, such as flash chromatography on a silica gel column.

The methods disclosed herein thus allow for the synthesis of piperazine molecules with the diverse functionalities disclosed herein. Certain of the schemes further provide a facile approach to obtain compounds that differ at the substituent containing the Q group since this is introduced after the cyclic intermediate has been synthesized.

It is further understood that for substituents or groups pendant to a piperazine ring carbon, that such ring carbon includes both a hydrogen atom and the specified substituent or group, such that the position includes such group in one of $R_{xa}$ or $R_{xb}$, and hydrogen in the remaining of $R_{xa}$ or $R_{xb}$. It may thus be seen that all possible stereochemical configurations are included within the disclosure of this invention.

The substituent

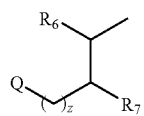

may be an amino acid residue or derivative thereof, including but not limited to a D-amino acid such as Phe, Phe(2-Cl), Phe(4-Cl), Phe(2,4-diCl), Phe(2,4-diF), Phe(3,4-diCl), Phe(4-NO$_2$), Phe(4-Me), Phe(4-Phenyl), HPhe, pF-Phe, Phe(4-Br), Phe(4-CF$_3$), Phe(3,4-diF), Phe(4-I), Phe(2-Cl, 4-Me), Phe(2-Me, 4-Cl), Phe(2-F, 4-Cl), Phe(2,4-diMe), Phe(2-Cl, 4-CF$_3$), Phe(3,4-di-OMe), Phg, Trp, Nal 1, Nal 2, Bip, Dip, Bpa, Ser(Bzl), Ser(2-Naphthyl), Ser(Phenyl), Ser(4-Cl-Phenyl), Ser(2-Cl-Phenyl), Lys(Z), Lys(Z-2'Br), Lys(Bz), Thr (Bzl), Tic, Tiq, Cys(Bzl), Tyr(2,6-DiCl-Bzl) and Tyr(Bzl), in each instance optionally further include a modified terminal amine, including a C$_1$ to C$_6$ linear or branched chain, a C$_1$ to C$_6$ linear or branched chain with an aryl group, an amine capping group, a second amino acid, or a second amino acid with a pendant amine capping group.

In one embodiment, the substituent containing the Q group may be of the general formula given above which is made by use of an aldehyde derivative of a D-amino acid. By use of an α-amino aldehyde the resulting substituent has the general structure:

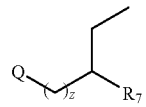

where the $R_6$ group is hydrogen, and thus is not shown. By way of example, where an aldehyde derivative of D-Phe is employed in synthesis, in the resulting compound $R_7$ may be NH$_2$, z may be 1, and Q may be phenyl. However, it can readily be seen that any D-amino acid listed above may be employed as an aldehyde derivative, and may further be seen that $R_7$ may be as generally defined, including any amine capping group, so long as $R_6$ is hydrogen. In synthesis, preferably an N-protected D-amino acid aldehyde is employed, where the N-protecting group is conventionally Boc or Fmoc. Because of the inherent instability of an α-amino aldehyde in solution, these compounds are preferably synthesized immediately prior to use. Two different methods are used for synthesis.

In the first method, to an N-protected amino acid (such as with a Boc- or Fmoc-group) in dichloromethane was added TBTU (1 eq) (here and elsewhere "eq" means equivalent or equivalents, as the context requires) and NMM (1 eq). The mixture was stirred for half an hour and N,O-dimethylhydroxylamine hydrochloride (1 eq) and NMM (1 eq) were added. The reaction was carried out overnight. The solvent was removed and EtOAc was added. The organic phase was washed by aqueous sodium bicarbonate, brine and dried over sodium sulfate. After evaporation of solvent and drying under vacuum the residue was dissolved in THF under nitrogen at −78° C. To this solution was added LAH (1 M in THF, 1.5 eq) slowly. The solution was stirred for an additional half hour. The reaction was diluted by ether and quenched by aqueous potassium hydrogen sulfate. The organic phase was washed with 1 N HCl, water, brine and dried over sodium sulfate. After removal of solvent the aldehyde was used immediately for the next step reaction without purification.

In the second method, to an N-protected amino acid (such as with a Boc- or Fmoc-group) in THF was added borane-THF (1 M, 1.2 eq) slowly at 0° C. The temperature was raised to room temperature and the solution stirred for 2 hours. The reaction was quenched by 1 N HCl and the solvent was evaporated. The crude product was purified on a silica gel column to give a pure N-protected amino alcohol. This alcohol was dissolved in dry dichloromethane and Dess-Martin periodinane (1.1 eq) was added. The solution was stirred for 1 hour and the reaction was diluted by ether. The organic phase was washed by saturated sodium bicarbonate with 10% sodium thiosulfate, then water, then brine and dried over sodium sulfate. After removal of solvent the crude product was used for the next step reaction immediately without further purification.

In the synthetic methods that follow, either of the foregoing methods may be employed to utilize a D-amino acid aldehyde.

Scheme 1: Synthetic Procedure for Preparation of 1,3-Substituted Piperazine Derivatives

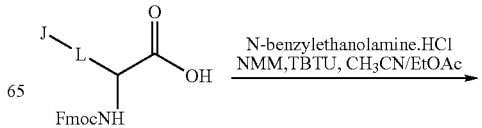

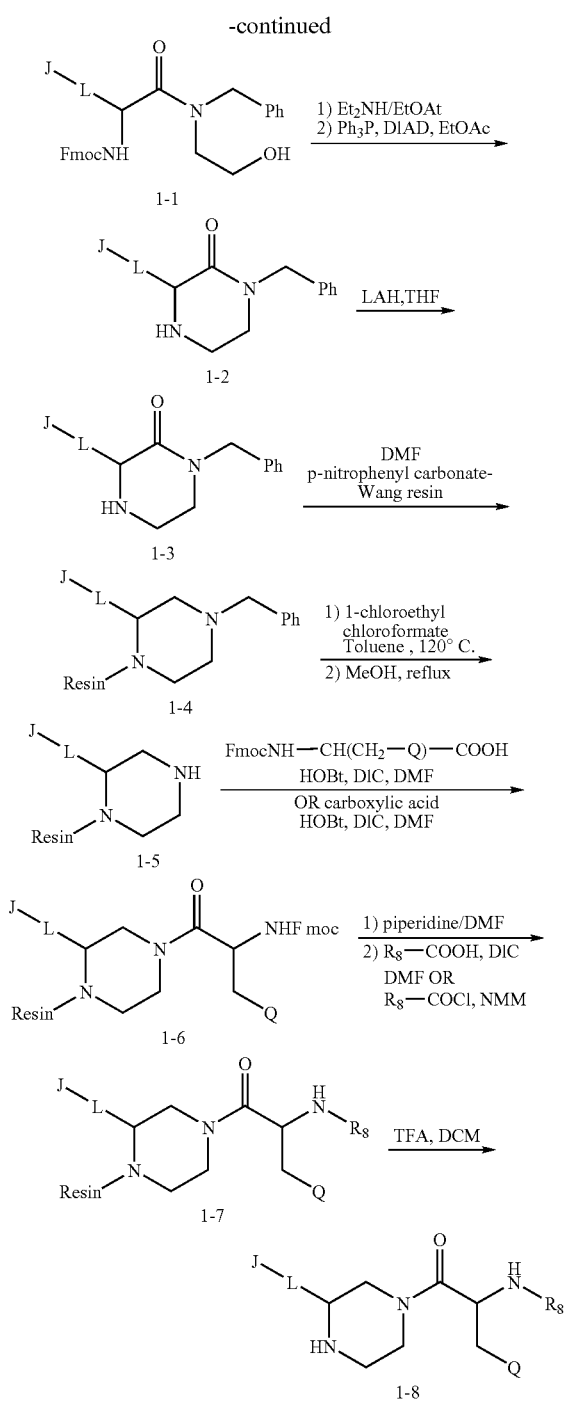

Fmoc-Nal 1-OH, Fmoc-D-Nal 2-OH, Fmoc-Nal 2-OH, Fmoc-D-Phe-OH or Fmoc-Phe-OH. Particularly preferred is Fmoc-D-Nal 2-OH; in this embodiment, TBTU (1.91 g, 5.94 mmol) was added to a solution of Fmoc-D-Nal 2-OH (2.0 g, 4.57 mmol), N-Benzylethanolamine (1.38 g, 9.14 mmol), and NMM (0.65 mL, 5.94 mmol) in acetonitrile/EtOAc (20 mL/10 mL) and stirred at room temperature for 1 hour. The solvent was evaporated under vacuum and the residue was diluted with EtOAc. The residue was washed with 1 N HCl (2 times), $H_2O$ (2 times), brine (1 time), and then dried over $MgSO_4$. The crude product 1-1 was concentrated for the next reaction without further purification.

Compound 1-1 was stirred with 25% $Et_2NH$ in EtOAc at room temperature overnight. After removal of solvent and co-evaporation with EtOAc, the crude product was dissolved in 20 mL of EtOAc. To this solution TPP ($Ph_3P$) (1.5 eq) and DIAD (1.1 eq) were added. The reaction mixture was stirred at room temperature for 1 hour. The solvent was evaporated and the residue was purified by flash column chromatography. The product 1-2 was obtained.

LAH (1.0 M in THF, 3.0 eq) was added dropwise to a solution of compound 1-2 in anhydrous THF under nitrogen at room temperature. The reaction mixture was stirred at room temperature for 1 hour, and quenched with 1 mL of 1 N sodium hydroxide. After filtration, the filtrate was diluted with EtOAc. The organic phase was washed with water, brine and dried over sodium sulfate. After removal of solvent the product 1-3 was used for the next reaction without further purification.

A mixture of 1-3 (1.5 eq) and p-nitrophenyl carbonate-Wang resin in DMF was heated at 50° C. with gentle stirring overnight. After a resin cleavage test showed the formation of the expected product, the resin was washed with MeOH, DMF, DCM and dried under high vacuum overnight to give product 1-4.

The dried resin 1-4 in 6 mL of toluene was treated with alpha-chloroethyl chloroformate (10 eq) at 120° C. for 1 hour. The resin was treated with one or more washes with MeOH, DMF, and DCM. Cleavage test showed no starting material left. This resin was refluxed in MeOH for 1 hour and washed with MeOH, DMF, and DCM to give resin 1-5.

Resin 1-5 was treated with FmocNH—CH($CH_2$—Q)—COOH (3 eq), HOBt (3 eq) and DIC (3 eq) in DMF at room temperature overnight. FmocNH—CH($CH_2$—Q)—COOH is an Fmoc amino acid wherein Q is a ring group including at least one aryl group. In alternative embodiments, FmocNH—CH(($CH_2$)$_z$—Q)—COOH may be employed, where z is an index value of from 0 to about 6. Representative examples of FmocNH—CH($CH_2$—Q)—COOH include Fmoc-D-Phe, any substituted Fmoc-D-Phe, Fmoc-Phe, any substituted Fmoc-Phe, as well as other amino acids described herein. Following treatment at room temperature overnight, the resulting compound was washed with MeOH, DMF, and DCM to give resin 1-6.

Alternatively, resin 1-5 was treated with carboxylic acid (instead of an Fmoc amino acid) in the same manner. In this case, the resulting compound 1-6 proceeds in the synthetic scheme to the reaction step described for 1-7 to directly give compound 1-8.

Resin 1-6 was treated with 4 mL of 20% piperidine in DMF at room temperature for 30 min, followed by washes with MeOH, DMF, and DCM. To this resin was added $R_8$—COOH (2 eq), NMM (2 eq) and DIC (2 eq) in DMF. The reaction was carried out at room temperature for 2 hours. The resin was washed with MeOH, DMF, and DCM to give resin 1-7. Alternatively, $R_8$—COOH was replaced by $R_8$—COCl (2 eq), which was used in the presence of NMM (2 eq) in DMF. The reaction was continued for 2 hours. The resin was washed as described above to give 1-7.

Resin 1-7 was treated with 2 mL of 50% TFA in DCM at room temperature for 1 hour. After filtration, the filtrate was concentrated and the crude product was purified by HPLC to give final product 1-8.

Scheme 2: Synthetic Procedure for Preparation of 1, 2, 5-Substitured Piperazine Derivatives

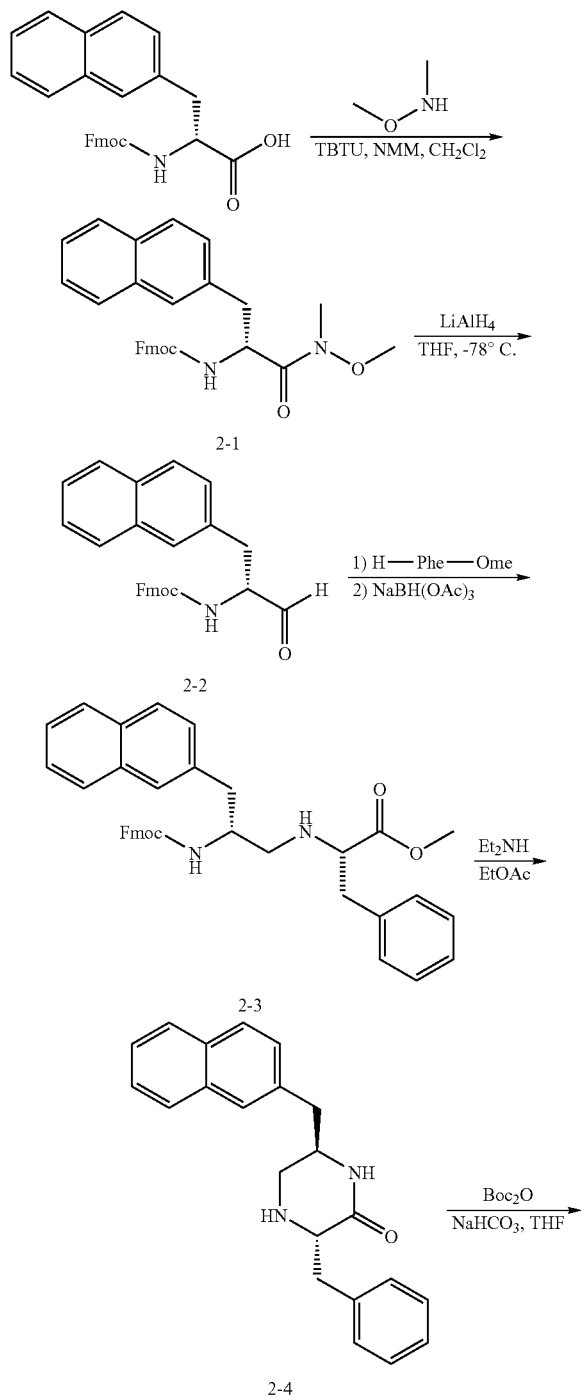

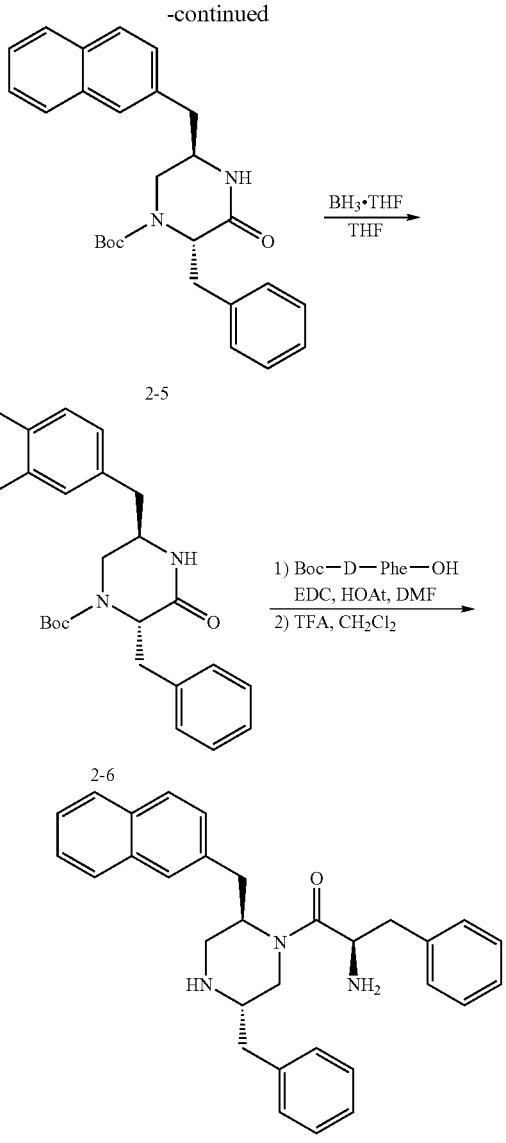

Fmoc-D-Nal 2-OH (4.5 g, 10 mmol), TBTU (3.2 g, 10 mmol), and NMM (1.02 g, 10 mmol) were dissolved in 200 mL of DCM and stirred at room temperature for 40 minutes. N,O-dimethylhydroxylamine hydrochloride (0.98 g, 10 mmol) and another equivalent of NMM was added and stirred at room temperature overnight. Mass spectrum showed completion of the reaction. The reaction mixture was washed with water and NaHCO$_3$ aqueous solution. The solvent was removed. The residue was partitioned between EtOAc and water. The organic phase was further washed with 0.5 M KHSO$_4$ and brine, then dried over sodium sulfate. Concentration gave 5.1 g of crude product 2-1.

Compound 2-1 was dissolved in 40 mL of anhydrous THF. The solution was cooled to −78° C. under N$_2$. LAH (1 M in THF, 12 mL, 1.2 eq) was added slowly and stirred at −78° C. for 1 hour. The reaction was quenched with slow addition of 20 mL of 0.75 M KHSO$_4$ to bring the pH to 5-6. The reaction mixture was concentrated and partitioned between EtOAc and water. The organic phase was washed with 0.5M HCl, brine, and then dried over sodium sulfate. Concentration gave 4.3 g of crude product 2-2, which was promptly used in the next step.

H-Phe-OMe hydrochloride (2.2 g, 10 mmol, 1 eq) and NMM (1.01 g, 1 eq) were mixed in THF and stirred for 5 min. Compound 2-2 (10 mmol) was added with 4 Å molecular sieve powder (1 g) and stirred at room temperature for 3 hours. NaBH(OAc)₃ (3.2 g, 15 mmol, 1.5 eq) was added to compound 2-2 and stirred at room temperature overnight. The reaction mixture was passed through celite. The filtrate was concentrated and partitioned between EtOAc and water. The organic phase was washed with brine and dried over sodium sulfate. Concentration gave 5.8 g of crude product 2-3.

Compound 2-3 was stirred with 8 mL of Et₂NH at room temperature overnight. The solvent was removed by vacuum. The residue was purified by silica gel column to give 1.4 g (4.2 mmol, 42% overall yield) of product 2-4.

To compound 2-4 (4.2 mmol) in 30 mL of THF was added 10 mL of water, 0.7 g (2 eq) of NaHCO₃, and 1.0 g (1.1 eq) of di-tert-butyl-dicarbonate. The reaction mixture was stirred at room temperature overnight. The reaction mixture was concentrated and partitioned between EtOAc and water. The aqueous layer was extracted twice with EtOAc. The organic phases were combined and washed with brine, then dried over sodium sulfate. Concentration gave 2 g of crude product 2-5.

Compound 2-5 (4.2 mmol) was dissolved in 20 mL of THF and cooled to 0° C. Borane-THF solution (1 M, 21 mL, 5 eq) was added slowly. The reaction mixture was allowed to stir at room temperature for 6 hours. The reaction was quenched with water at 0-5° C. The reaction mixture was stirred with 25 mL of 1 M HCl at room temperature overnight. The reaction mixture was cooled with ice-water bath. Saturated sodium bicarbonate solution was added to bring the pH to 8-9. The mixture was concentrated and extracted with EtOAc. The organic phases were combined and washed with brine, then dried over sodium sulfate. After evaporation of solvent, silica gel column purification with EtOAc gave 520 mg of pure product 2-6 (31% for 2 steps).

Boc-D-Phe (79 mg, 0.30 mmol), EDC (58 mg, 0.30 mmol), and HOAt (0.30 mmol) in DMF were stirred at room temperature for 1 hour. Compound 2-6 (90 mg, 0.22 mmol) was added and stirred at room temperature overnight. DMF was removed by vacuum. The residue was partitioned between EtOAc and 5% LiCl aqueous solution. The aqueous layer was extracted with EtOAc. The organic layers were combined and washed with brine, then dried over sodium sulfate. The solvent was removed. Purification by silica gel column (hexane: EtOAc at 1:1) gave 128 mg of solid, which was stirred with 1.5 mL of TFA (50% in DCM) for 1 hour. Purification by HPLC gave 20 mg of pure product as 2-7.

Scheme 3: Synthetic Procedure for Preparation of 1, 3, 4-Substituted Piperazine Derivatives -continued

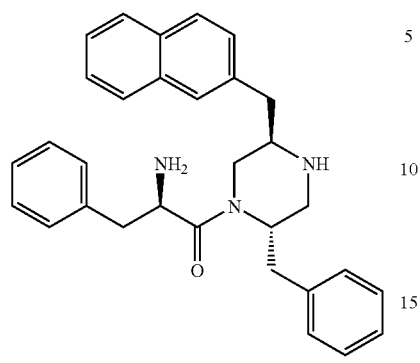

3-5

Preparation of 2-6 was as described in Scheme 2. Compound 2-6 (0.23 mmol) was dissolved in 5 mL of DCM and cooled to 0° C. Et₃N (0.6 mmol, 3 eq) was added slowly. Benzyl chloroformate (Cbz-Cl) was added drop-wise and stirred at 0° C. for 2 hours. The reaction mixture was washed with water and brine and dried over sodium sulfate. Silica gel column purification (hexane:EtOAc at 1:1) gave 110 mg of compound 3-1 (87%).

Compound 3-1 (110 mg) was stirred with 1 mL of TFA and 1 mL of DCM for 1 hour. The reaction mixture was concentrated and dissolved in ethyl ether. NMM was added to bring the pH to 8-9. After washing with brine, the organic phase was dried over sodium sulfate and purified by silica gel column to give 3-2.

Boc-protected amino acid (0.28 mmol), EDC (0.28 mmol), and HOAt (0.28 mmol) in DMF were stirred at room temperature for 45 minutes. Compound 3-2 (0.20 mmol) was added and stirred at room temperature overnight. DMF was removed by vacuum. Purification by silica gel column (hexane:EtOAc at 1:1) gave compound 3-3.

Compound 3-3 was dissolved in 5 mL of methanol and Pd/C (10% wt) was added. The air in the reaction flask was purged with H₂ 3 times. The reaction mixture was stirred under H₂ for 5 hours. The reaction mixture was filtered to give crude compound 3-4.

Compound 3-4 was stirred with 2 mL of TFA (50% in DCM) for 1 hour. After removal of solvent the residue was purified by HPLC to give compound 3-5.

Scheme 4: Synthetic Procedure for Preparation of 1, 2, 5-Substituted Piperazine Derivatives

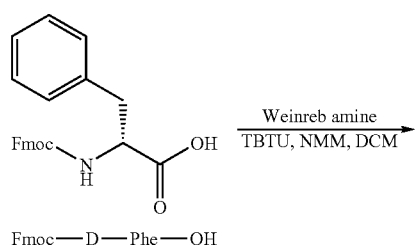

Fmoc—D—Phe—OH

-continued

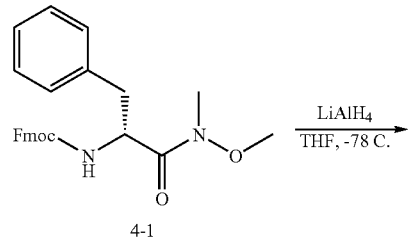

4-1

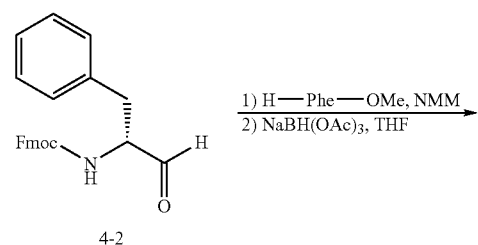

4-2

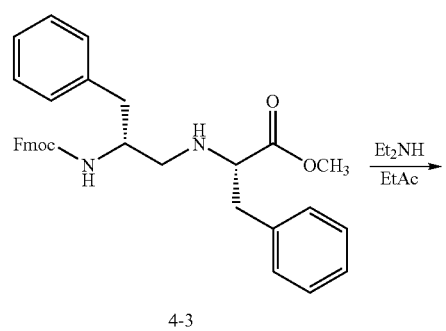

4-3

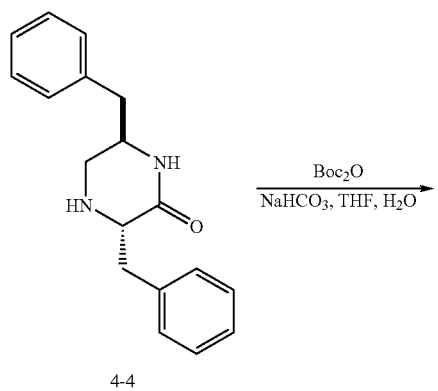

4-4

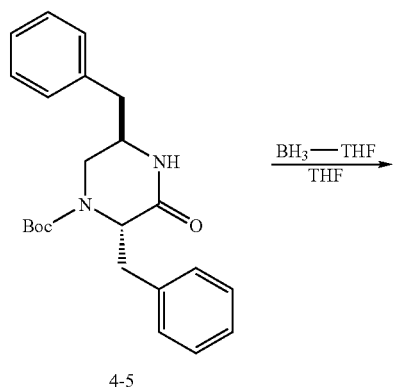

4-5

-continued

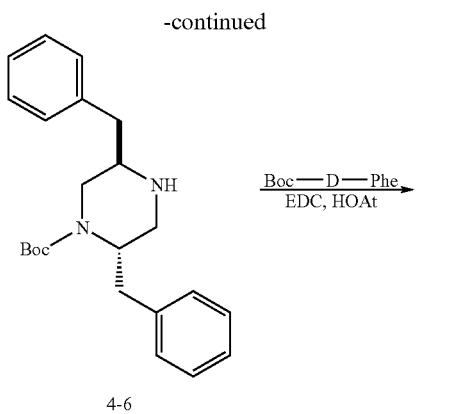

4-6

Boc—D—Phe
EDC, HOAt
→

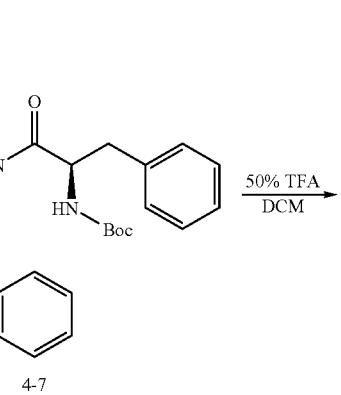

4-7

50% TFA
DCM
→

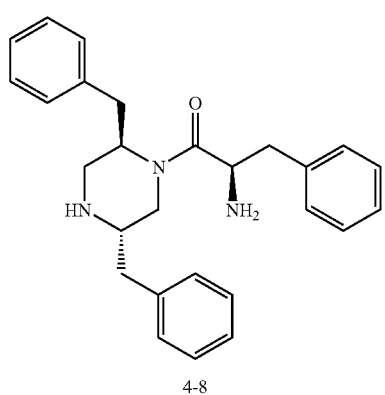

4-8

Fmoc-D-Phe (12 g, 31 mmol), TBTU (10.3 g, 32 mmol), and NMM (3.2 g, 32 mmol) were dissolved in 250 mL of DCM and stirred at room temperature for 45 min. N,O-dimethyl-hydroxylamine hydrochloride (3.1 g, 32 mmol) and one more equivalent of NMM was added and stirred at room temperature overnight. The reaction mixture was washed with water and NaHCO$_3$ aqueous solution. The solvent was removed. The residue was partitioned between EtOAc and water. The organic phase was further washed with 0.75 M KHSO$_4$ and brine, then dried over sodium sulfate. Concentration gave 12 g of crude product 4-1.

Compound 4-1 was dissolved in 120 mL of anhydrous THF. The solution was cooled to −78° C. under N$_2$. LAH (1 M in THF, 36 mL, 1.2 eq) was added slowly and stirred at −78° C. for 1 hour. The reaction was quenched with slow addition of 0.75 M KHSO$_4$ to bring the pH to 5-6. The reaction mixture was concentrated and partitioned between EtOAc and water. The organic phase was washed with 0.5 M HCl, brine, and dried over sodium sulfate. Concentration gave 11 g of crude product 4-2.

H-Phe-OMe hydrochloride (6.45 g, 30 mmol, 1 eq) was mixed with NMM (3.03 g, 1 eq) and stirred for 5 minutes. Compound 4-2 (30 mmol) was added with 4 Å molecular sieve powder (3.0 g) and stirred at room temperature for 3 hours. NaBH(OAc)$_3$ (8.4 g, 40 mmol, 1.33 eq) was added and stirred at room temperature overnight. The reaction mixture was filtered through celite. The filtrate was concentrated and partitioned between EtOAc and water. The organic phase was washed with brine and dried over sodium sulfate. Concentration gave 16 g of crude product 4-3.

Compound 4-3 was stirred with 15 mL of Et$_2$NH at room temperature overnight. The solvent was removed by vacuum. The residue was purified by silica gel column to give 3.8 g (13.6 mmol, 45% overall yield) of product 4-4.

To compound 4-4 (13.5 mmol) in 120 mL of THF was added 30 mL of water, 2.1 g (2 eq) of NaHCO$_3$, and 3.3 g (1.1 eq) of di-tert-butyl-dicarbonate. The reaction mixture was stirred at room temperature overnight. The reaction mixture was concentrated and partitioned between EtOAc and water. The aqueous layer was extracted twice with EtOAc. The organic phases were combined and washed with brine, and dried over sodium sulfate. Purification with silica gel column (hexane:EtOAc at 1:1) gave 3.2 g (63%) of product 4-5.

Compound 4-5 (8.4 mmol) was dissolved in 60 mL of THF and cooled to 0° C. Borane-THF solution (1 M, 5 eq) was added slowly. The reaction mixture was allowed to stir at room temperature for 6 hours. The reaction was quenched with water at 0-5° C. The reaction mixture was stirred with 50 mL of 1 M NaOH at room temperature overnight. The reaction mixture was cooled with ice-water bath. Saturated sodium bicarbonate solution was added to bring the pH to 8-9. The mixture was concentrated and extracted with EtOAc. The organic phases were combined and washed with brine, and dried over sodium sulfate. Silica gel column purification (hexane:EtOAc at 1:1) gave 800 mg of pure product 4-6 (27% for 2 steps).

Boc-D-Phe (74 mg, 0.28 mmol), EDC (54 mg, 0.28 mmol), and HOAt (0.28 mmol) in DMF were stirred at room temperature for 40 minutes. Compound 4-6 (75 mg, 0.20 mmol) was added and stirred at room temperature overnight. DMF was removed by vacuum. The residue was partitioned between EtOAc and 5% LiCl aqueous solution. The aqueous layer was extracted with EtOAc. The organic layers were combined and washed with brine, and dried over sodium sulfate. Purification by silica gel column (hexane:EtOAc at 1:1) gave 88 mg (72%) of solid compound 4-7.

Compound 4-7 (88 mg, 0.144 mmol) was stirred with 2.0 mL of TFA (50% in DCM) for 1 hour. Purification by HPLC gave 30 mg of pure product 4-8.

Scheme 5: Synthetic Procedure for Preparation of 1, 3, 4-Substituted Piperazine Derivatives

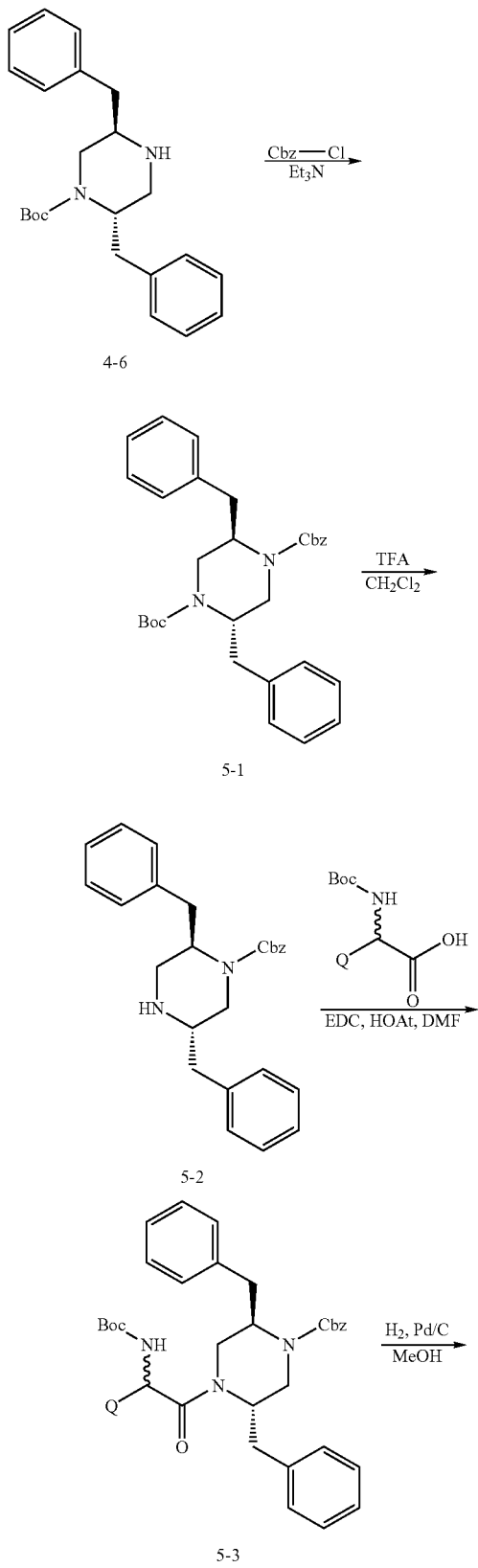

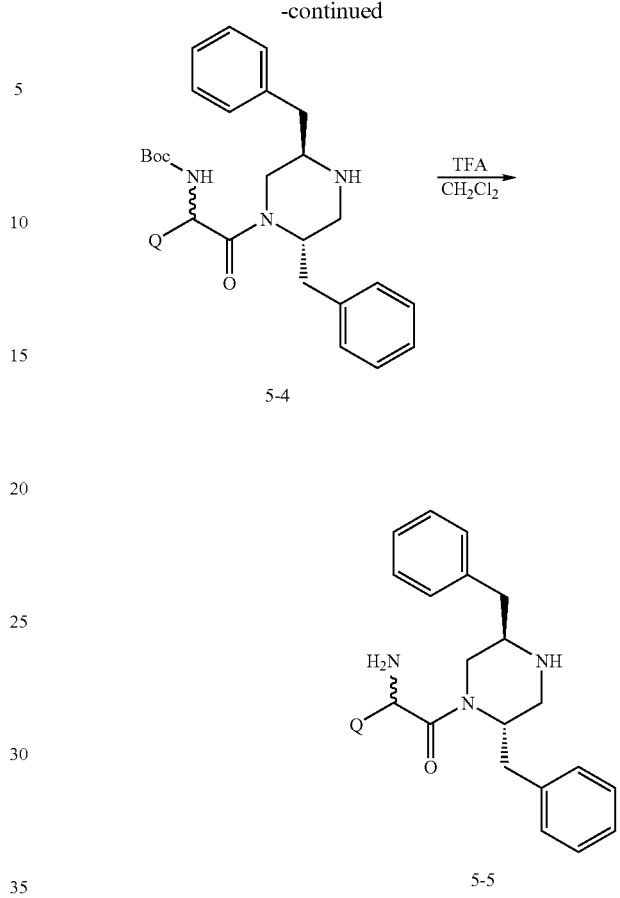

Preparation of 4-6 was as described in Scheme 4. Compound 4-6 (1.28 mmol) was dissolved in 20 mL of DCM and cooled to 0° C. Et$_3$N (3.85 mmol, 3 eq) was added slowly. Benzyl chloroformate was added drop-wise and stirred at 0° C. for 2 hours. The reaction mixture was washed with water and brine, the dried over sodium sulfate. Silica gel column purification (hexane:EtOAc at 1:1) gave 600 mg of compound 5-1 (87%).

Compound 5-1 (600 mg) was stirred with 4 mL of TFA and 4 mL of DCM for 1 hour. The reaction mixture was concentrated and dissolved in ethyl ether. NMM was added to bring the pH to 8-9. After washing with brine, the organic phase was dried over sodium sulfate and purified by silica gel column.

Boc-protected amino acid (0.28 mmol), EDC (0.28 mmol), and HOAt (0.28 mmol) in DMF were stirred at room temperature for 45 minutes. Compound 5-2 (0.20 mmol) was added and stirred at room temperature overnight. DMF was removed by vacuum. Purification by silica gel column (hexane:EtOAc at 1:1) gave compound 5-3.

Compound 5-3 (40 mg) was dissolved in 5 mL of MeOH. Pd/C (10% wt) was added. The air in the reaction flask was purged with H$_2$ 3 times. The reaction mixture was stirred under H$_2$ for 5 hours. The reaction mixture was filtered to give crude 5-4.

Compound 5-4 was stirred with 2 mL of TFA (50% in DCM) for 1 hour. Purification by HPLC gave final compound 5-5.

Scheme 6: Synthetic Scheme for Preparation of Substituted Piperazine Precursors

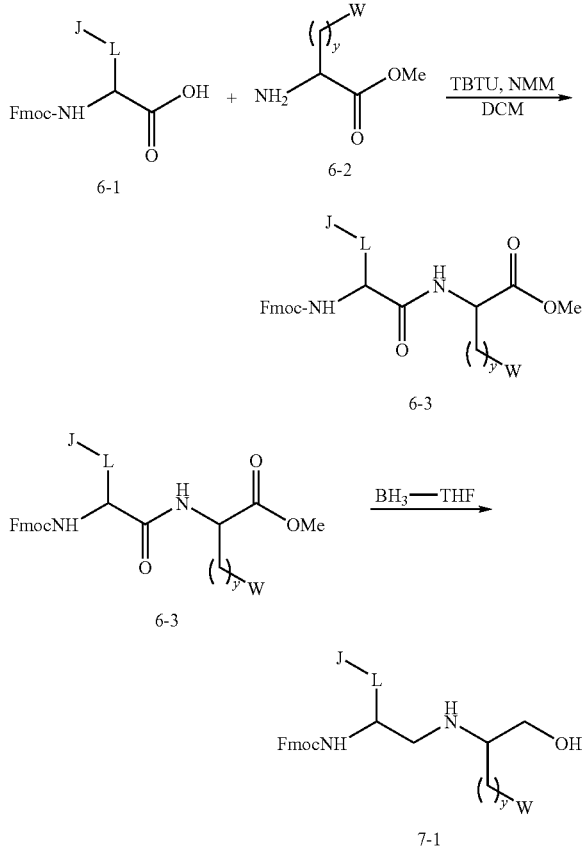

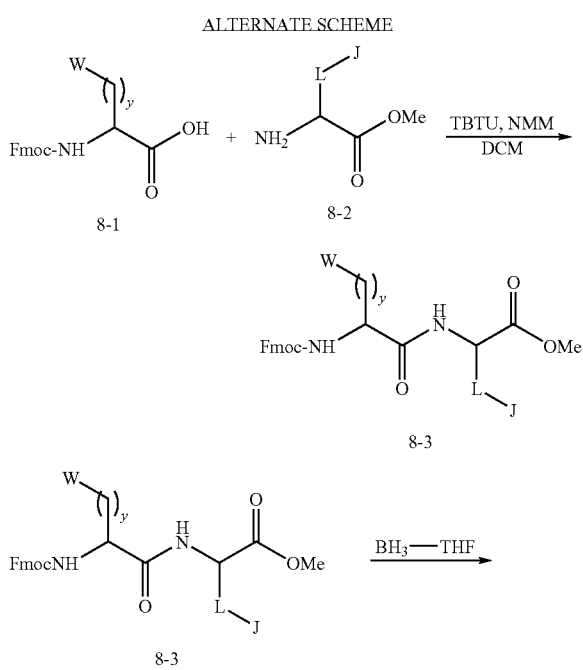

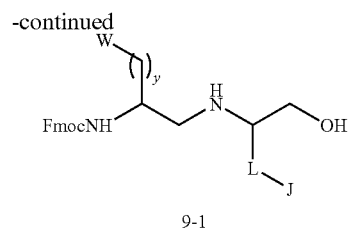

The starting material is Fmoc-amino acid 6-1, an amino acid with —L—J as the side chain, such as where L is a bond or linker, including linkers such as —CH$_2$—, and J is a substituted or unsubstituted monocyclic or bicyclic ring structure, including preferably an aromatic ring group such as phenyl, substituted phenyl, naphthyl or substituted naphthyl. Examples of FmocNH—CH(L—J)—COOH include Fmoc-D-Nal 1-OH, Fmoc-Nal 1-OH, Fmoc-D-Nal 2-OH, Fmoc-Nal 2-OH, Fmoc-D-Phe-OH or Fmoc-Phe-OH. Fmoc-amino acid 6-1 is added to a mixture of NMM (1 eq) and TBTU (1 eq) taken in dry DCM and stirred at room temperature for 30 minutes. An amino acid methyl ester (6-2) is added to this mixture and stirred at room temperature for 16 hours. The amino acid methyl ester contains as its side chain —(CH$_2$)$_y$—W, where y is 0 or 1 (or a greater number not to exceed 6) and W is a substituted or unsubstituted aryl group, or in an alternative embodiment, y is 0 and W is hydrogen, or yet in another alternative embodiment, y is 1 and W is a C$_1$ to C$_5$ linear or branched chain, such that —CH$_2$—W is a C$_1$ to C$_6$ linear or branched chain. The solvent is evaporated and the residue is extracted by EtOAc. The organic layer is washed by 1 N NaOH, water, 1 N HCl, water, brine and dried over sodium sulfate. After removal of the solvent the di-peptide methyl ester is purified on a column to give 6-3.

Compound 6-3 is dissolved in THF at 0° C. and to this solution borane-THF (1 M, 6 eq) is added dropwise. The reaction is carried out at 0° C. for 1 hour and room temperature for 4 hours. It is quenched by 1 N HCl at 0° C. and the product is extracted by EtOAc. The organic phase is washed by 1 N HCl, water and brine, and dried over sodium sulfate. After evaporation of solvent the resulting precursor compound (7-1) is used for the next step reaction.

Alternatively, the positions of —L—J and —CH$_2$—W are reversed. Thus the starting material is Fmoc-amino acid 8-1, an amino acid with —(CH$_2$)$_y$—W as the side chain, where y is 0 or 1 (or a greater number not to exceed 6) and W is a substituted or unsubstituted aryl group, or in an alternative embodiment, y is 0 and W is hydrogen, or yet in another alternative embodiment, y is 1 and W is a C$_1$ to C$_5$ linear or branched chain, such that —CH$_2$—W is a C$_1$ to C$_6$ linear or branched chain. For example, Gly provides an embodiment where y is 0 and W is hydrogen. Val provides an embodiment where the side chain is isopropyl, and so on. Fmoc-amino acid 8-1 is added to a mixture of NMM (1 eq) and TBTU (1 eq) taken in dry DCM and stirred at room temperature for 30 minutes. An amino acid methyl ester (8-2) is added to this mixture and stirred at room temperature for 16 hours. The amino acid methyl ester contains as its side chain —L—J, such as where L is a bond or linker, including linkers such as —CH$_2$—, and J is a substituted or unsubstituted monocyclic or bicyclic ring structure, including preferably an aromatic ring group such as phenyl, substituted phenyl, naphthyl or substituted naphthyl. The solvent is evaporated and the residue is extracted by EtOAc. The organic layer is washed by 1 N NaOH, water, 1 N HCl, water, brine and dried over sodium sulfate. After removal of the solvent the di-peptide methyl ester is purified on a column to give 8-3.

After evaporation of solvent the resulting precursor compound (9-1) is used for the next step reaction.

Scheme 7: Synthetic Scheme for Preparation of Substituted Piperazine From Precursors

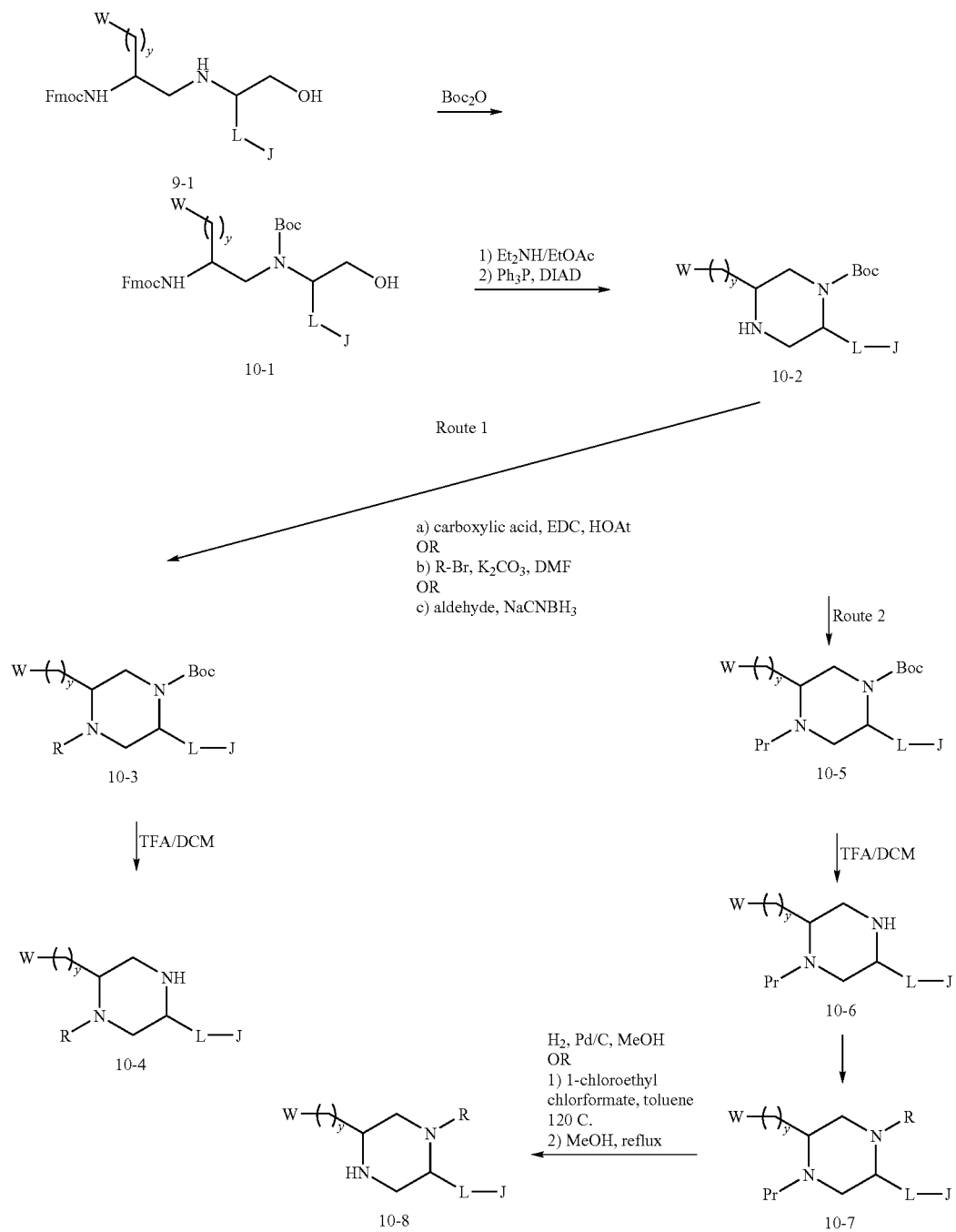

Compound 8-3 is dissolved in THF at 0° C. and to this solution borane-THF (1 M, 6 eq) is added dropwise. The reaction is carried out at 0° C. for 1 hour and room temperature for 4 hours. It is quenched by 1 N HCl at 0° C. and the product is extracted by EtOAc. The organic phase is washed by 1 N HCl, water and brine, and dried over sodium sulfate.

Compound 9-1 is dissolved in THF and reacted with di-t-butyl carbonate (1.2 eq) in the presence of sodium bicarbonate (1.2 eq). After completion of reaction the compound is purified on silica gel column to give compound 10-1.

Compound 10-2 is treated with 20% Et₂NH in EtOAc for 6 hours. The solvent is evaporated to dryness and the residue is dissolved in THF. The solution is cooled to 0° C. and to this solution is added DIAD in THF slowly. The reaction is carried out at 0° C. for 1 hour and room temperature overnight. After evaporation of solvent the residue is purified to give compound 10-2.

Route 1:

To a solution of carboxylic acid/Boc-protected amino acids and 1-hydroxy-7-azabenzotriazole (1 eq) in dry N,N-dimethylformamide is added 1-(3-dimethylaminopropyl)-3-ethylcarbodimide hydrochloride (1 eq). After the mixture is stirred at room temperature for one-half hour, 10-2 (1 eq.) is added. The reaction is continued for 16 hours. The reaction mixture is poured into water and extracted by EtOAc twice. The organic layer is washed by 1 N hydrochloric acid twice, 1 N sodium hydroxide twice, brine and dried over sodium sulfate. After evaporation, the product is purified on silica gel column to give 10-3.

Alternatively, an aliphatic bromide (1 eq) is stirred with the 10-2 and potassium carbonate in DMF overnight at room temperature. The reaction mixture is poured into water and extracted by EtOAc twice. The organic layer is washed by aqueous sodium bicarbonate, brine and dried over sodium sulfate. After evaporation, the product is purified on silica gel column to give 10-3.

Alternatively, a mixture of 10-2 and a desired aldehyde (1 eq) (for example, a Boc- or Fmoc-protected amino acid aldehyde) is stirred in the presence of activated 4 Å molecular sieves in dry THF (10% acetic acid) for 1 hour. Sodium cyanoborohydride (1 eq, 1 M solution in THF) is added to this mixture. After 2 hours, solvent is evaporated and the residue purified on silica gel column to give 10-3.

Compound 10-3 is treated by a solution of TFA/DCM (1/1=v/v) for one hour. After evaporation of solvent the residue is purified by HPLC to give final compound 10-4.

Route 2:

In route 2, "Pr" stands for protecting groups, such as Cbz or benzyl groups as described below.

Compound 10-2 is dissolved in dry THF. To this solution is added NMM (1 eq) and benzyl chloroformate in THF (1 eq) at 0° C. The reaction is stirred overnight. After evaporation of solvent the residue is purified on silica gel column to give compound 10-5.

Alternatively, a mixture of 10-3 and benzaldehyde (1 eq) is stirred in the presence of activated 4 Å molecular sieves in dry THF (10% acetic acid) for 1 hour. Sodium cyanoborohydride (1 eq, 1 M solution in THF) is added to this mixture. After 2 hours, solvent is evaporated and the residue purified on silica gel column to give 10-5.

Compound 10-5 is treated with TFA/DCM (1/1=v/v) for one hour. After removal of solvent the residue is extracted by EtOAc from 1 N NaOH. The organic phase is washed by water, brine and dried over sodium sulfate. The solvent is evaporated. The product 10-6 is used for the next step without further purification.

Compound 10-7 is synthesized by the same procedures described for compound 10-3.

Compound 10-7 is dissolved in methanol and subjected to 1 atm. hydrogen in the presence of a catalytic amount of palladium on carbon (10%) overnight at room temperature. The catalyst is removed by filtration and solvent evaporated to give crude product, which is purified by HPLC to give 10-8.

Alternatively, the benzyl group is removed by the method described in the synthesis of compound 1-5. The crude compound is purified to give 10-8.

In another embodiment, the starting material is 7-1. However, the reactions proceed as described above, as shown:

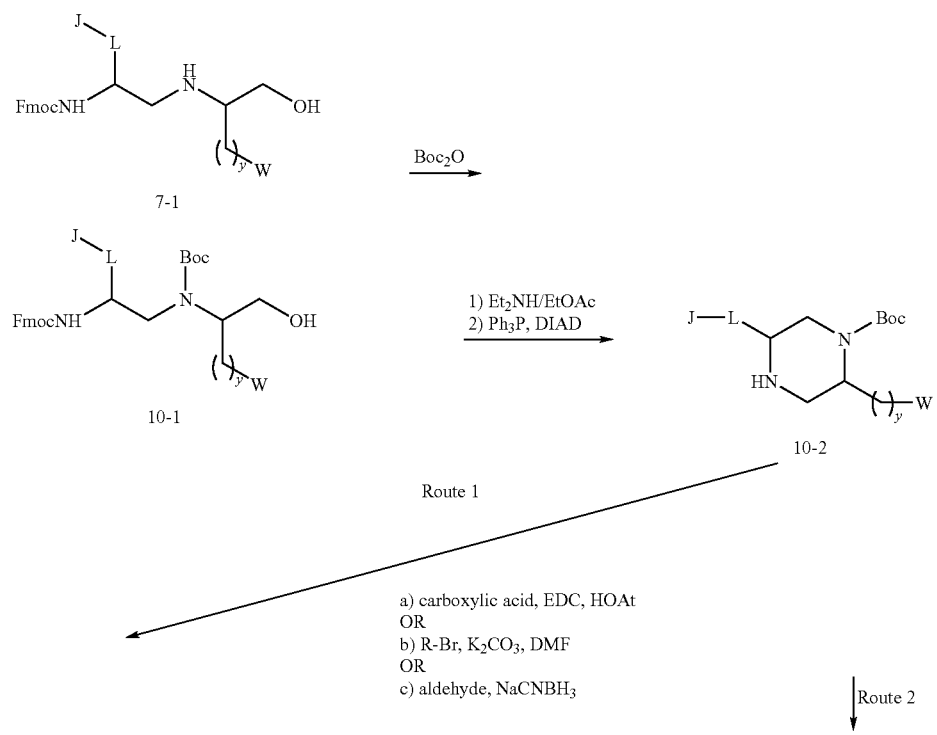

-continued

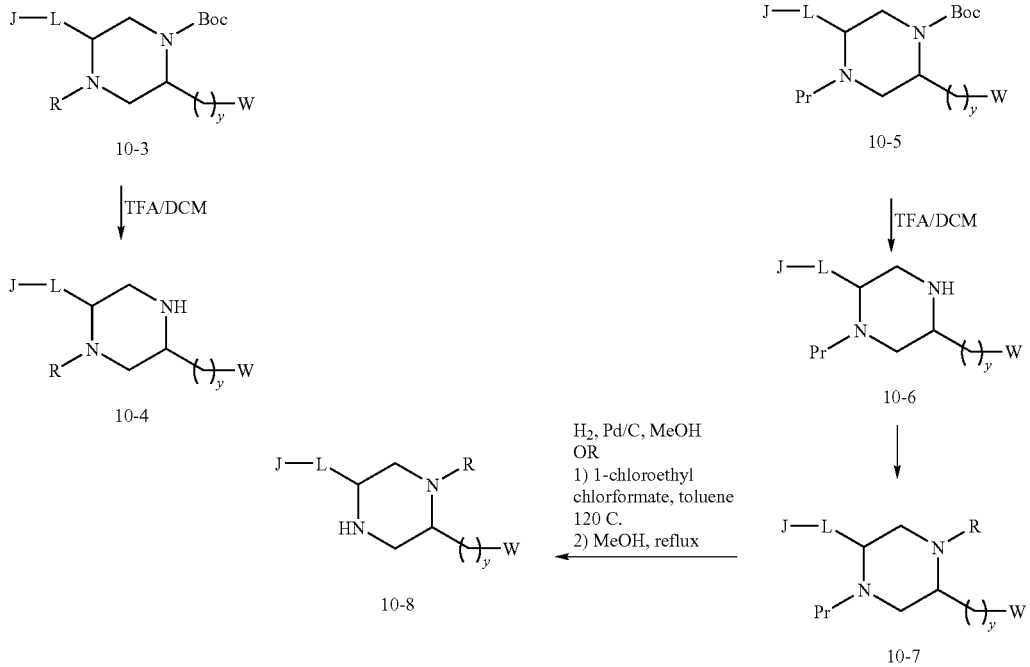

Assays and Tests Employed in the Invention.

Competitive inhibition assay. A competitive inhibition binding assay was conducted using membranes prepared from hMC1-R or B-16 mouse melanoma cells (containing MC1-R), hMC3-R, hMC4-R, and hMC5-R, and using 0.4 nM $^{125}$I-NDP-α-MSH (New England Nuclear, Boston, Mass., USA) in 50 mM HEPES buffer containing 1 mM $MgCl_2$, 2 mM $CaCl_2$, and 5 mM KCl, at pH 7.2. The assay tube also contained a chosen concentration of the test compound of this invention, typically a 1 µM concentration, for determining its efficacy in inhibiting the binding of $^{125}$I-NDP-α-MSH to its receptor. Non-specific binding was measured by complete inhibition of binding of $^{125}$I-NDP-α-MSH in the assay with the presence of 1 µM α-MSH.

Incubation was for 90 minutes at room temperature, after which the assay mixture was filtered and the membranes washed three times with ice cold buffer. The filter was dried and counted in a gamma counter for remaining radioactivity bound to the membranes. 100% specific binding was defined as the difference in radioactivity (cpm) bound to cell membranes in the absence and presence of 1 µM α-MSH. The cpm obtained in the presence of test compounds are normalized with respect to 100% specific binding to determine the percent inhibition of $^{125}$I-NDP-a-MSH binding. Each assay was conducted in triplicate and the actual mean values are described, with results less than 0% reported as 0%. "ND" indicates that no assay was conducted with respect to the specific melanocortin receptor source.

$EC_{50}$ determination in functional activity assay. The Ki (nM) of certain compounds of the invention is determined. Functional evaluation of compounds at melanocortin receptors are performed by measuring the accumulation of intracellular cAMP in HEK-293 cells expressing MC3-R, MC4-R or MC5-R, and in B-16 mouse melanoma cells (containing MC1-R). Cells, suspended in Earle's Balanced Salt Solution containing 10 mM HEPES, pH 7.5, 5 mM $MgCl_2$, 1 mM glutamine, 0.1% albumin and 0.6 mM 3-isobutyl-1-methyl-xanthine, a phosphodiesterase inhibitor, are plated in 96 well plates at a density of $0.5 \times 10^5$ cells per well. Cells are incubated with the test compounds in the presence or absence of α-MSH for 1 hour at 37° C. cAMP levels are measured by EIA (Amersham) in the cell lysates. Data analysis and $EC_{50}$ values are determined using nonlinear regression analysis with Prism Graph-Pad software.

Functional status. The agonist/antagonist status with respect to MC1-4, MC4-R, and MC5-R of selected compounds of the invention are determined. Antagonistic activity is determined by measuring the inhibition of α-MSH-induced cAMP levels following exposure to the compounds as in the preceding descriptions.

Penile erection induction. The ability of compounds to induce penile erection (PE) in male rats is evaluated with selected compounds. Male Sprague-Dawley rats weighing 200-250 g are kept on a 12 hour on/off light cycle with food and water ad libitum. All behavioral studies are performed between 10 a.m. and 5 p.m. Groups of 4-8 rats are treated with compounds at a variety of doses via intravenous (IV) or intracerebroventricular (ICV) routes. Immediately after treatment, rats are placed into individual polystyrene cages (27 cm long, 16 cm wide, and 25 cm high) for behavioral observation. Rats are observed for 30 minutes IV or 90 minutes ICV, and the number of yawns, grooming bouts and PEs are recorded in 10-minute bins.

ICV food intake and body weight change. Change in food intake and body weight is evaluated with selected compounds. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) are fed powdered chow and water ad libitum. For 1 week before treatment, 24-hour food intake and body weight change is recorded to assess a baseline for the group during vehicle treatment. The rats are dosed ICV with vehicle or selected compounds (1-3 nmol). The changes in body weight and food intake for the 24 hour period after dosing are determined. The changes in body weight and food intake for the 48 hour period, and in some cases for 72 hours as well, after dosing are also measured to determined reversal of changes in body weight and food intake effect back to baseline.

IV food intake and body weight change. Change in food intake and body weight is evaluated with selected compounds. Male Sprague-Dawley rats weighing ~300 g at the beginning of the experiment are kept on a 12 hour on/off light cycle. Lights out is adjusted to 12:00 p.m. to allow for dosing just prior to the start of their dark period. Rats (8-12/group) are fed powdered chow and water ad libitum. For 1 week before treatment, 24-hour food intake and body weight change is recorded to assess a baseline for the group during vehicle treatment. The rats are dosed IV with vehicle or selected compounds (0.5-3 mg/kg). The changes in body weight and food intake for the 24 hour period after dosing are determined. The changes in body weight and food intake for the 48 hour period, and in same cases for 72 hours as well, after dosing are also measured to determined reversal of changes in body weight and food intake effect back to baseline.

Determination of mass and nuclear magnetic resonance analysis. The mass values were determined using a Waters MicroMass ZQ device utilizing a positive mode. Mass determinations were compared with calculated values and expressed in the form of mass weight plus one (M+1).

Proton NMR data is obtained using a Bruker 300 MHz spectrometer. The spectra are obtained after dissolving compounds in a deuteriated solvent such as chloroform, dimethyl sulfoxide, or methanol as appropriate.

Representative Compounds of the Invention

EXAMPLE 1

(R)-2-Amino-1-((2R,5S)-5-benzyl-2-naphthalen-2-ylmethyl-piperazin-1-yl)-3 phenyl-propan-1-one The following compound was synthesized by the method of Scheme 2. It was tested as described above with the results shown. The molecular weight (M+1) was 463.6.

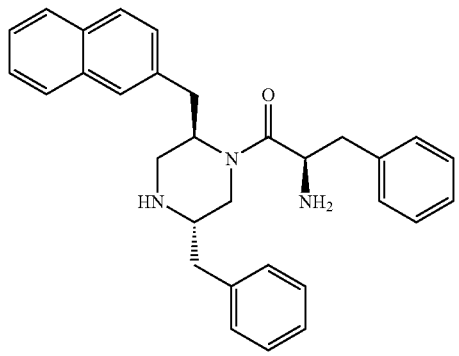

| Inhibition at 1 μM | | | | |
|---|---|---|---|---|
| MC1-R (human) | MC1-R (murine) | MC3-R | MC4-R | MC5-R |
| 0 | ND | 14 | 33 | 8 |

EXAMPLE 2

1-((2R,5S)-5-Benzyl-2-naphthalen-2-ylmethyl-piperazin-1-yl)-3-(2,4-dichloro-phenyl)-propan-1-one The following compound was synthesized by the method of Scheme 2. It was tested as described above with the results shown. The molecular weight (M+1) was 516.6.

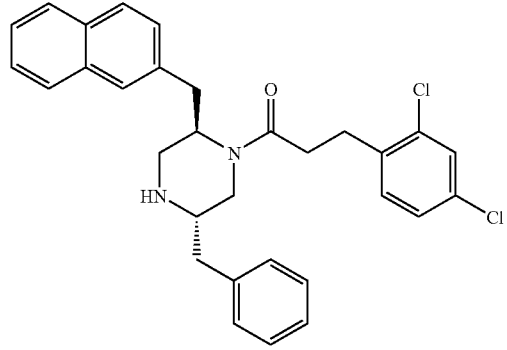

| Inhibition at 1 μM | | | | |
|---|---|---|---|---|
| MC1-R (human) | MC1-R (murine) | MC3-R | MC4-R | MC5-R |
| 9 | ND | 9 | 18 | 6 |

In the synthesis of the compound of example 2, Scheme 2 was modified as follows:

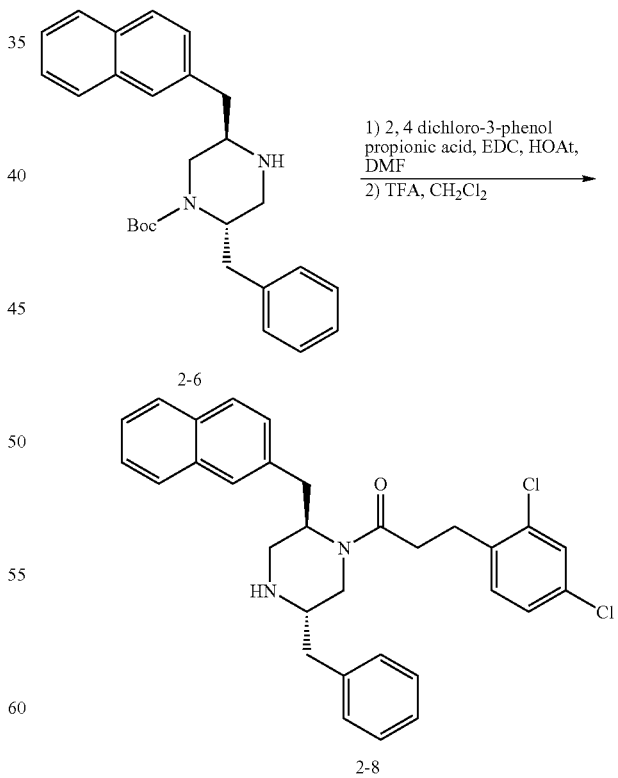

EDC (54 mg, 0.28 mmol) and HOAt (0.28 mmol) were added to 2,4-dichloro-3-phenol propionic acid (61 mg, 0.28 mmol) in DMF. The reaction mixture was stirred at room temperature for 1 hour. Compound 2-6 (84 mg, 0.20 mmol) was added and stirred at room temperature overnight.

DMF was removed by vacuum. The residue was partitioned between EtOAc and 5% LiCl aqueous solution. The aqueous layer was extracted with EtOAc. The organic layers were combined, washed with brine, and dried over sodium sulfate. Purification by silica gel column (hexane:EtOAc at 1:1) gave 110 mg of solid, which was stirred with 1.5 mL of TFA (50% in DCM) for 1 hour. Purification by HPLC gave 20 mg of pure product 24.

EXAMPLE 3

(R)-2-Amino-1-((2R,5S)-5-benzyl-2-naphthalen-2-ylmethyl-piperazin-1-yl)-3-naphthalen-2-yl-propan-1-one The following compound was synthesized by the method of Scheme 2. It was tested as described above with the results shown. The molecular weight (M+1) was 513.7.

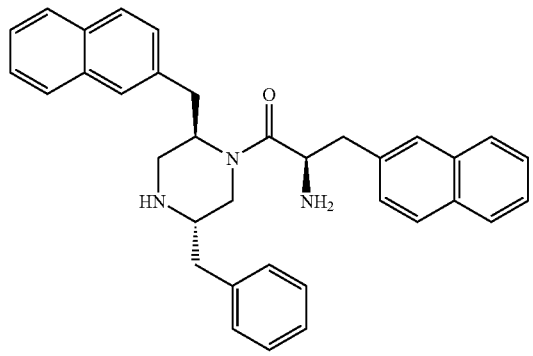

| | Inhibition at 1 μM | | | |
|---|---|---|---|---|
| MC1-R (human) | MC1-R (murine) | MC3-R | MC4-R | MC5-R |
| 10 | ND | 19 | 39 | 21 |

In the synthesis of the compound of example 3, Scheme 2 was modified as follows:

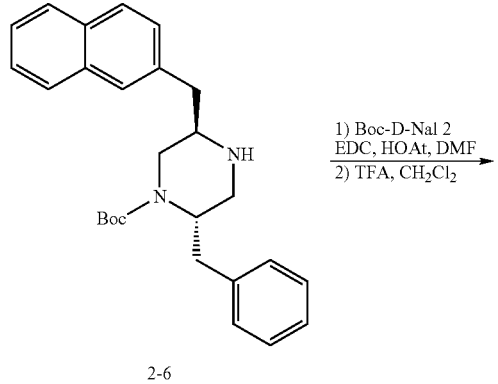

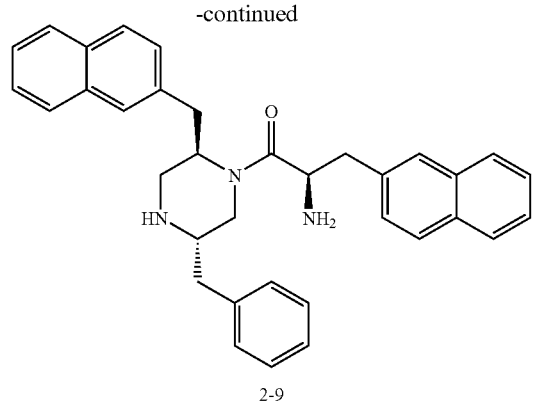

2-9

To Boc-D-Nal 2-OH (88 mg, 0.28 mmol) in DMF was added EDC (54 mg, 0.28 mmol) and HOAt (0.28 mmol). The reaction mixture was stirred at room temperature for 1 hour. Compound 2-6 (84 mg, 0.20 mmol) was added and stirred at room temperature overnight. DMF was removed by vacuum. The residue was partitioned between EtOAc and 5% LiCl aqueous solution. The aqueous layer was extracted with EtOAc. The organic layers were combined and washed with brine, the dried over sodium sulfate. Purification by silica gel column (hexane:EtOAc at 1:1) gave 130 mg of solid, which was stirred with 1.5 mL of TFA (50% in DCM) for 1 hour. Purification by HPLC gave 50 mg of pure product as compound 2-9.

EXAMPLE 4

(S)-2-Amino-1-((2R,5S)-5-benzyl-2-naphthalen-2-ylmethyl-piperazin-1-yl)-3-phenyl-propan-1-one The following compound was synthesized by the method of Scheme 2. It was tested as described above with the results shown. The molecular weight (M+1) was 464.2.

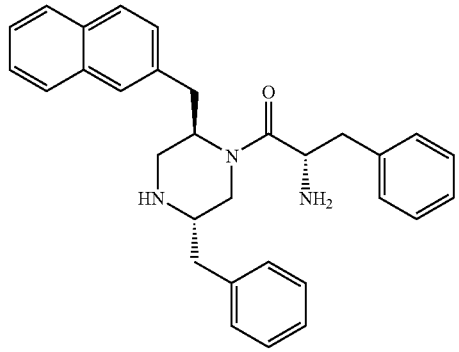

| | Inhibition at 1 μM | | | |
|---|---|---|---|---|
| MC1-R (human) | MC1-R (murine) | MC3-R | MC4-R | MC5-R |
| 6 | ND | 13 | 25 | 11 |

In the synthesis of the compound of example 4, Scheme 2 was modified as follows:

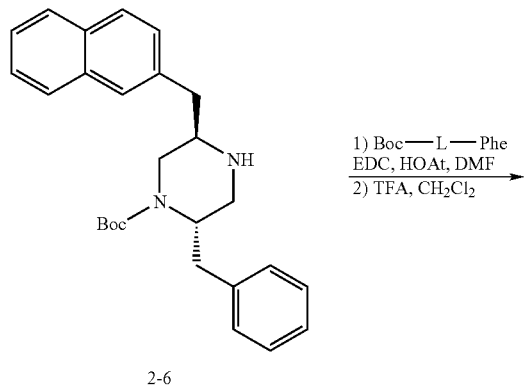

2-6

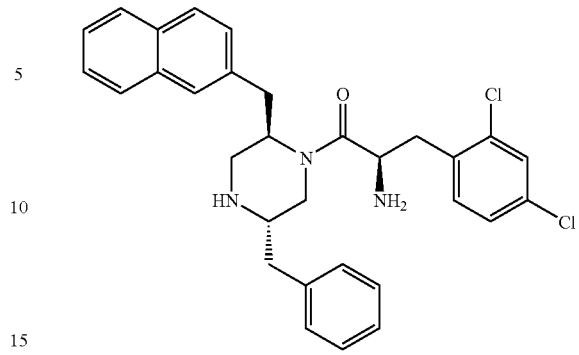

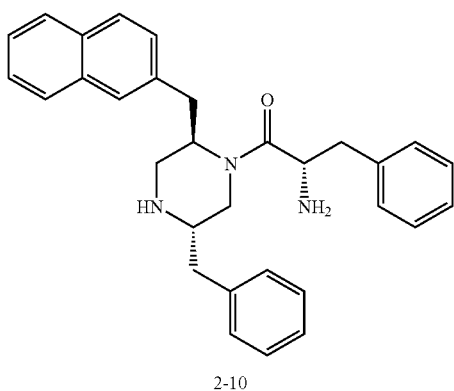

2-10

EDC (54 mg, 0.28 mmol) and HOAt (0.28 mmol) were added to Boc-L-Phe-OH (74 mg, 0.28 mmol) in DMF. The reaction mixture was stirred at room temperature for 1 hour. Compound 2-6 (84 mg, 0.20 mmol) was added and the mixture was stirred at room temperature overnight.

DMF was removed by vacuum. The residue was partitioned between EtOAc and 5% LiCl aqueous solution. The aqueous layer was extracted with EtOAc. The organic layers were combined and washed with brine, the dried over sodium sulfate. Purification by silica gel column (hexane:EtOAc at 1:1) gave 130 mg of solid, which was stirred with 1.5 mL of TFA (50% in DCM) for 1 hour. Purification by HPLC gave 50 mg of pure product as 2-10.

EXAMPLE 5

(R)-2-Amino-1-((2R,5S)-5-benzyl-2-naphthalen-2-ylmethyl-piperazin-1-yl)-3-(2,4-dichloro-phenyl)-propan-1-one The following compound was synthesized by the method of Scheme 1. It was tested as described above with the results shown. The molecular weight (M+1) was 531.6.

| | Inhibition at 1 μM | | | |
|---|---|---|---|---|
| MC1-R (human) | MC1-R (murine) | MC3-R | MC4-R | MC5-R |
| 0 | ND | 12 | 34 | 22 |

In the synthesis of the compound of example 5, Scheme 2 was modified as follows:

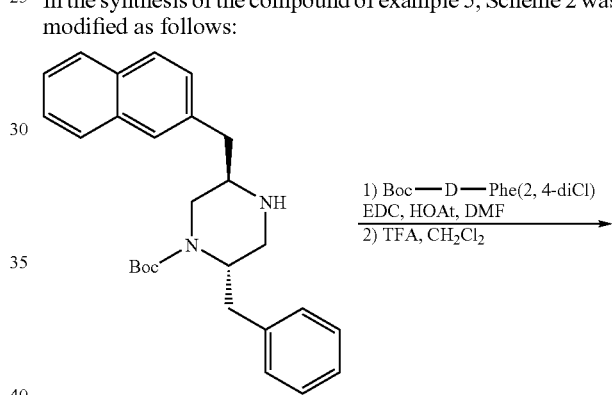

2-6

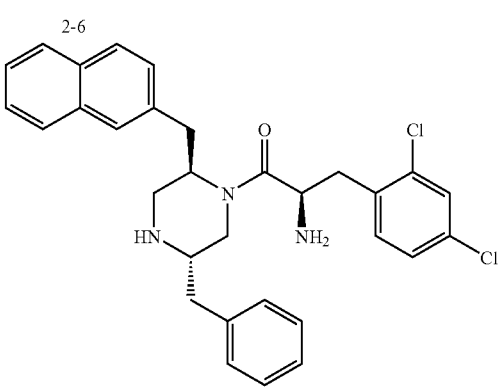

2-11

EDC (54 mg, 0.28 mmol) and HOAt (0.28 mmol) were added to Boc-D-Phe(2,4-diCl)—OH (93 mg, 0.28 mmol) in DMF and stirred at room temperature for 1 hour. Compound 2-6 (84 mg, 0.20 mmol) was added and stirred at room temperature overnight. DMF was removed by vacuum. The residue was partitioned between EtOAc and 5% LiCl aqueous solution. The aqueous layer was extracted with EtOAc. The organic layers were combined and washed with brine, the dried over sodium sulfate. Purification by silica gel column (hexane:EtOAc at 1:1) gave 115 mg of solid, which was stirred with 1.5 mL of TFA (50% in DCM) for 1 hour. Purification by HPLC gave 40 mg of pure product as 2-11.

EXAMPLE 6

(R)-2-Amino-1-((2R,5S)-2,5-dibenzyl-piperazin-1-yl)-3-phenyl-propan-1-one

The following compound was synthesized by the method of Scheme 4. It was tested as described above with the results shown. The molecular weight (M+1) was 414.1.

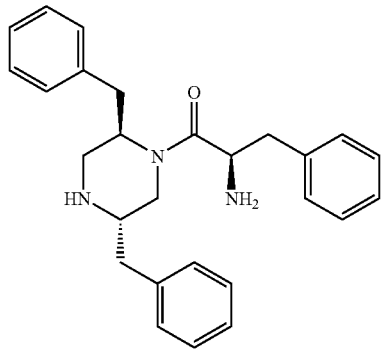

| | Inhibition at 1 μM | | | |
|---|---|---|---|---|
| MC1-R (human) | MC1-R (murine) | MC3-R | MC4-R | MC5-R |
| 0 | 0 | 12 | 4 | 13 |

EXAMPLE 7

(R)-2-Amino-1-((2S,5R)-2-benzyl-5-naphthalen-2-ylmethyl-piperazin-1-yl)-3-phenyl-propan-1-oneylamino-3-phenyl-propan-1-one The following compound was synthesized by the method of Scheme 3. It was tested as described above with the results shown. The molecular weight (M+1) was 464.1.

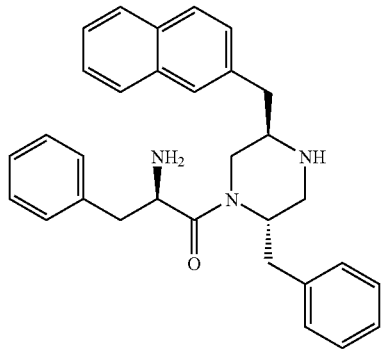

| | Inhibition at 1 μM | | | |
|---|---|---|---|---|
| MC1-R (human) | MC1-R (murine) | MC3-R | MC4-R | MC5-R |
| 17 | 0 | 9 | 16 | 13 |

In the synthetic method of Scheme 3, the Boc-protected amino acid was Boc-D-Phe-OH, as shown in the actual scheme.

EXAMPLE 8

(R)-2-Amino-1-((2R,5S)-2,5-dibenzyl-piperazin-1-yl)-3-naphthalen-2-yl-propan-1-one The following compound was synthesized by the method of Scheme 4. It was tested as described above with the results shown. The molecular weight (M+1) was 464.0.

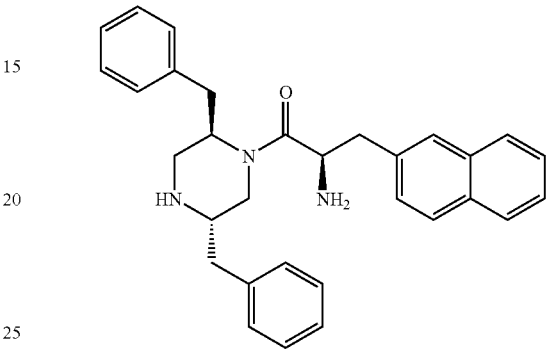

| | Inhibition at 1 μM | | | |
|---|---|---|---|---|
| MC1-R (human) | MC1-R (murine) | MC3-R | MC4-R | MC5-R |
| ND | 0 | 0 | 0 | 10 |

In the synthesis of the compound of example 8, Scheme 4 was modified as follows:

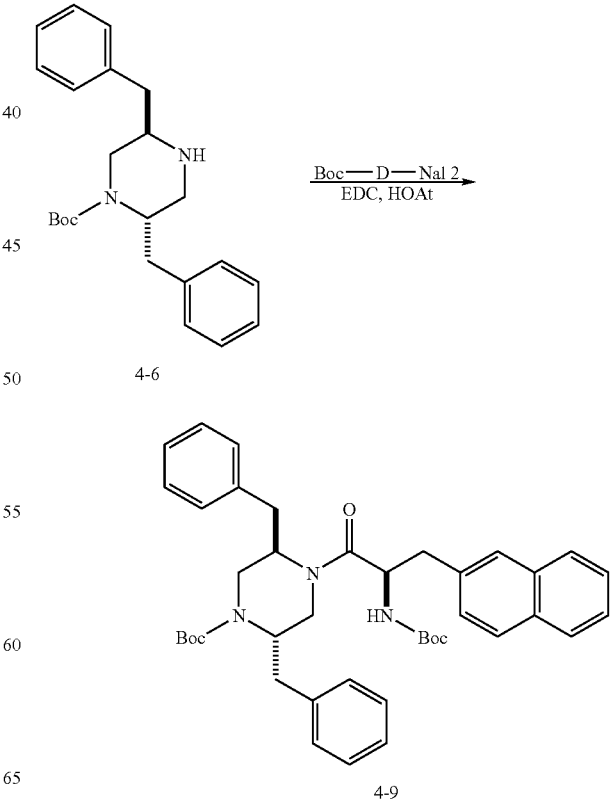

Boc-D-Nal 2-OH (88 mg, 0.28 mmol), EDC (54 mg, 0.28 mmol), and HOAt (0.28 mmol) in DMF were stirred at room temperature for 40 minutes. Compound 4-6 (75 mg, 0.20 mmol) was added and stirred at room temperature overnight. DMF was removed by vacuum. Purification by silica gel column (hexane:EtOAc at 1:1) gave 100 mg (76%) of solid compound 4-9.

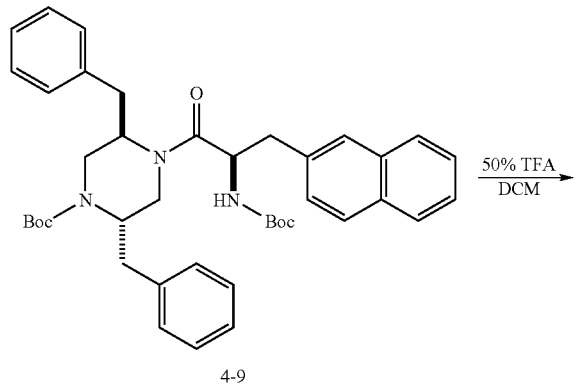

4-9

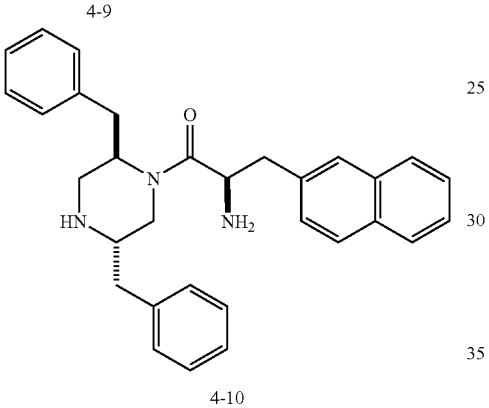

4-10

Compound 4-9 (100 mg) was stirred with 2 mL of TFA (50% in DCM) for 1 hour. Purification by HPLC gave 19 mg of pure product as compound 4-10.

EXAMPLE 9

(S)-2-Amino-1-((2R,5S)-2,5-dibenzyl-piperazin-1-yl)-3-phenyl-propan-1-one

The following compound was synthesized by the method of Scheme 4. It was tested as described above with the results shown. The molecular weight (M+1) was 414.2.

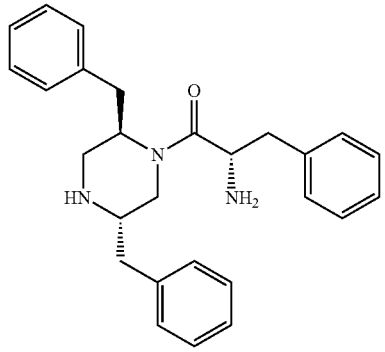

| Inhibition at 1 μM | | | | |
|---|---|---|---|---|
| MC1-R (human) | MC1-R (murine) | MC3-R | MC4-R | MC5-R |
| ND | 0 | 0 | 0 | 0 |

In the synthesis of the compound of example 9, Scheme 4 was modified as follows:

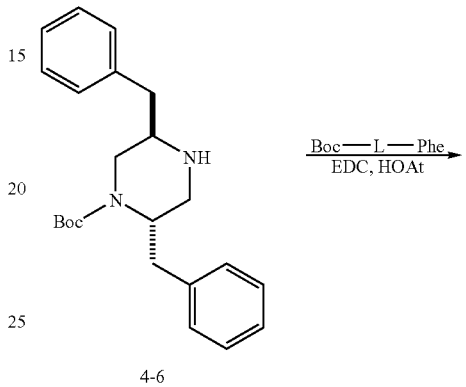

4-6

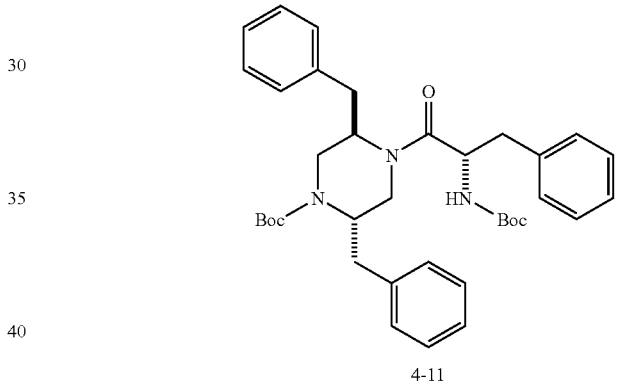

4-11

Boc-L-Phe-OH (74 mg, 0.28 mmol), EDC (54 mg, 0.28 mmol), and HOAt (0.28 mmol) in DMF were stirred at room temperature for 40 minutes. Compound 4-6 (75 mg, 0.20 mmol) was added and stirred at room temperature overnight. DMF was removed by vacuum. The residue was purified by silica gel column (hexane:EtOAcat 1:1) to give 110 mg (90%) of product 4-11.

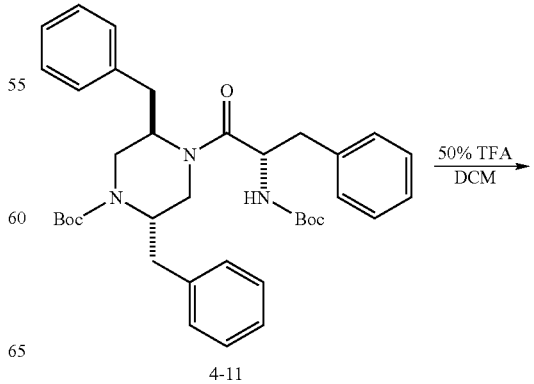

4-11

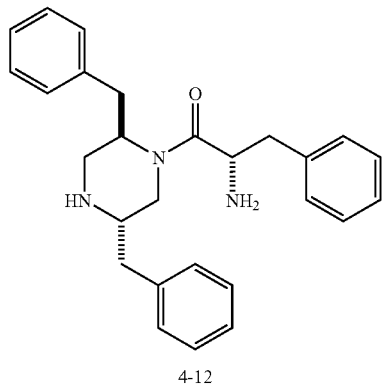

4-12

Compound 4-11 (110 mg) was stirred with 2.0 mL of TFA (50% in DCM) for 1 hour. Purification by HPLC gave 70 mg of pure product as 4-12.

EXAMPLE 10

(R)-2-Amino-1-((2R,5S)-2,5-dibenzyl-piperazin-1-yl)-3-(2,4-dichloro-phenyl)-propan-1-one The following compound was synthesized by the method of Scheme 4. It was tested as described above with the results shown. The molecular weight (M+1) was 483.7.

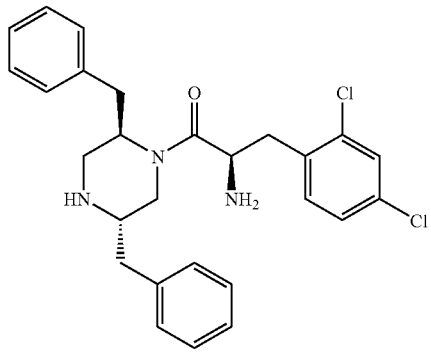

| | Inhibition at 1 μM | | | |
|---|---|---|---|---|
| MC1-R (human) | MC1-R (murine) | MC3-R | MC4-R | MC5-R |
| ND | 0 | 0 | 13 | 0 |

In the synthesis of the compound of example 10, Scheme 4 was modified as follows:

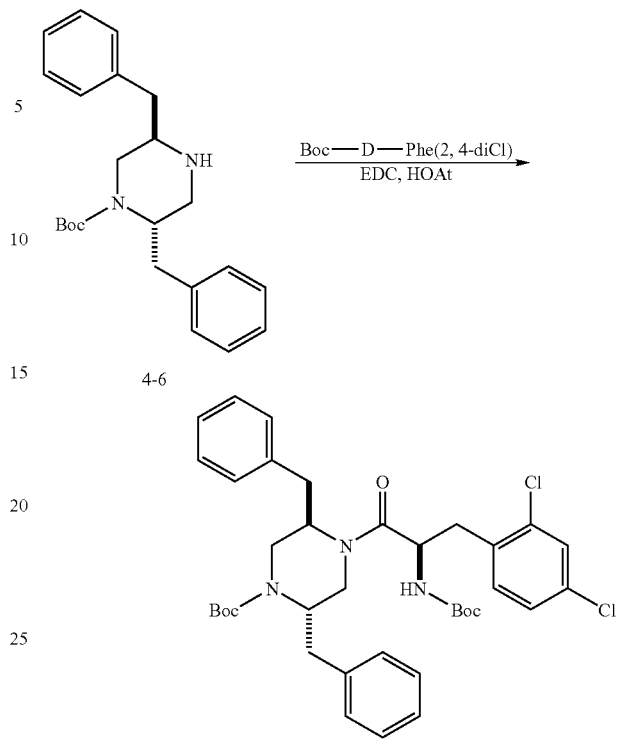

4-6

4-13

Boc-D-Phe(2,4-diCl)—OH (84 mg, 0.25 mmol), EDC (48 mg, 0.25 mmol), and HOAt (0.25 mmol) in DMF were stirred at room temperature for 1 hour. Compound 4-6 (75 mg, 0.20 mmol) was added and stirred at room temperature overnight. DMF was removed by vacuum. The residue was purified by silica gel column (hexane:EtOAc at 1:1) to give 110 mg (81%) of product 4-13.

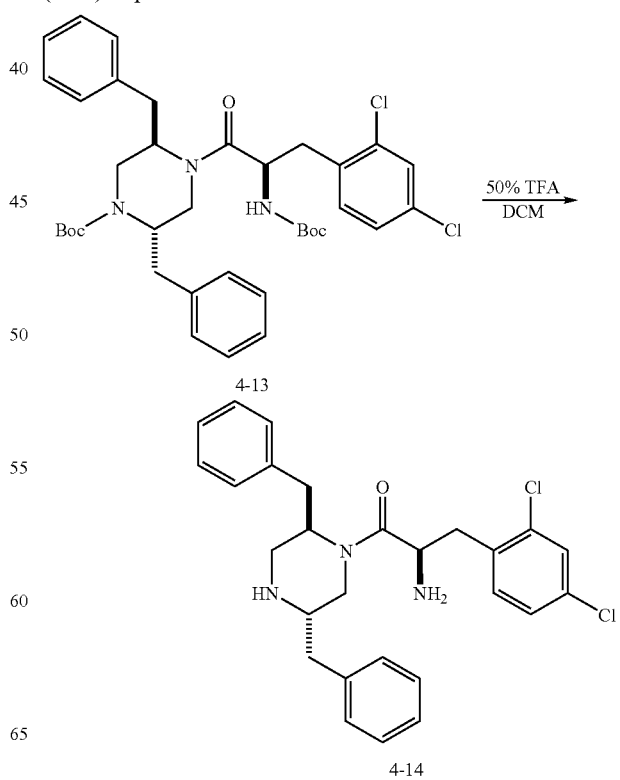

4-13

4-14

Compound 4-13 (110 mg) was stirred with 2 mL of TFA (50% in DCM) for 1 hour. Purification by HPLC gave 47 mg of pure product as 4-14.

EXAMPLE 11

(R)-2-Amino-3-(2-chloro-phenyl)-1-((R)-3-naphthalen-2-ylmethyl-piperazin-1-yl)-propan-1-one The following compound was synthesized by the method of Scheme 1. It was tested as described above with the results shown. The molecular weight (M+1) was 408.0.

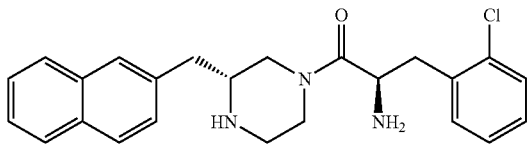

| MC1-R (human) | MC1-R (murine) | MC3-R | MC4-R | MC5-R |
|---|---|---|---|---|
| ND | 4 | 19 | 9 | 0 |

In the synthesis of Example 11, the starting material used in Scheme 1 was Fmoc-D-Nal 2-OH. In the synthesis of compound 1-6, Fmoc-D-Phe(2-Cl)—OH was employed as FmocNH—CH(CH$_2$—Q)—COOH. No R$_8$—COOH group was employed, so the synthetic method of Scheme 1 proceeded to treatment of the resin and purification:

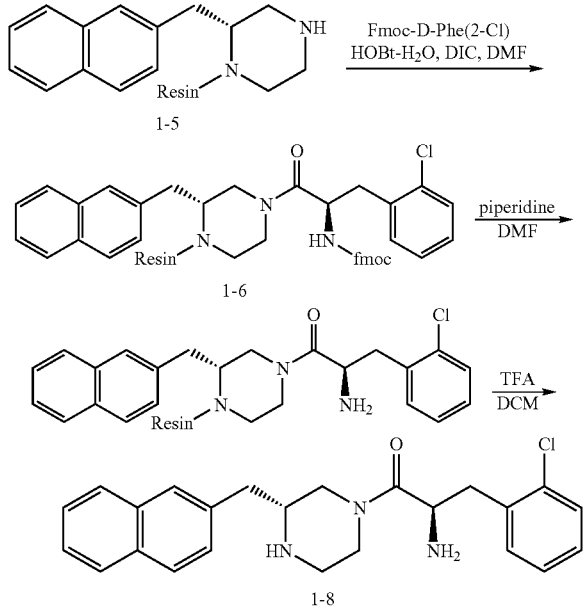

EXAMPLE 12

(S)-2-Amino-N—[(R)-1-(2-chloro-benzyl)-2-((R)-3-naphthalen-2-ylmethyl-piperazin-1-yl)-2-oxo-ethyl]-3-(1H-imidazol-4-yl)-propionamide The following compound was synthesized by the method of Scheme 1. It was tested as described above with the results shown. The molecular weight (M+1) was 544.9.

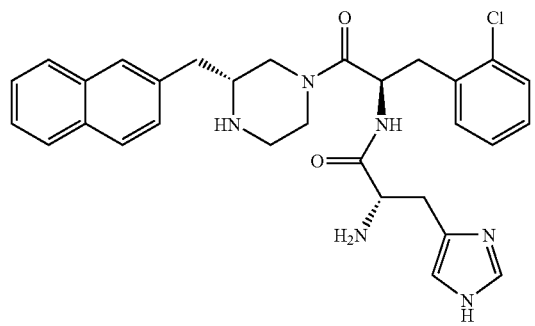

| MC1-R (human) | MC1-R (murine) | MC3-R | MC4-R | MC5-R |
|---|---|---|---|---|
| ND | 52 | 18 | 0 | 12 |

In the synthesis of Example 12, the starting material used in Scheme 1 was Fmoc-D-Nal 2-OH. In the synthesis of compound 1-6, Fmoc-D-Phe(2-Cl)—OH was employed as FmocNH—CH(CH$_2$—Q)—COOH. The R$_8$—COOH group was Boc-L-His(Boc)$_2$-OH:

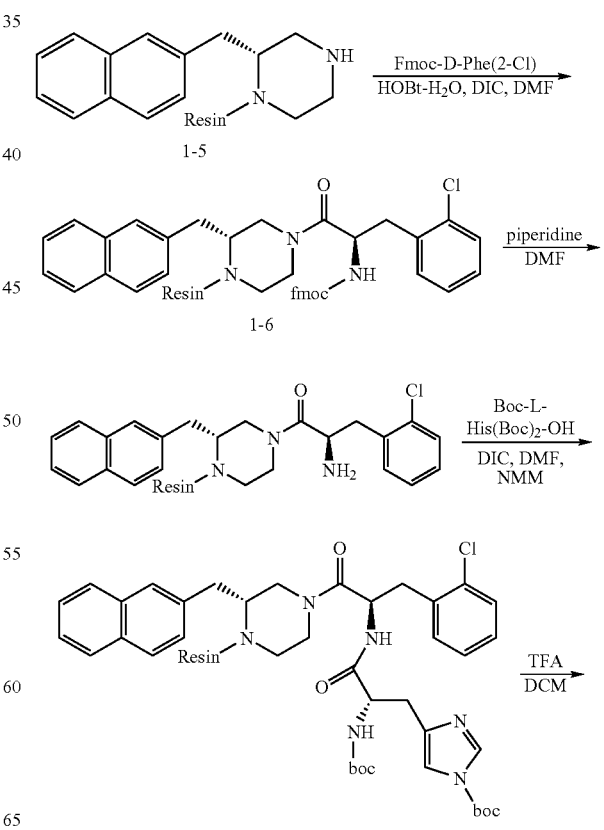

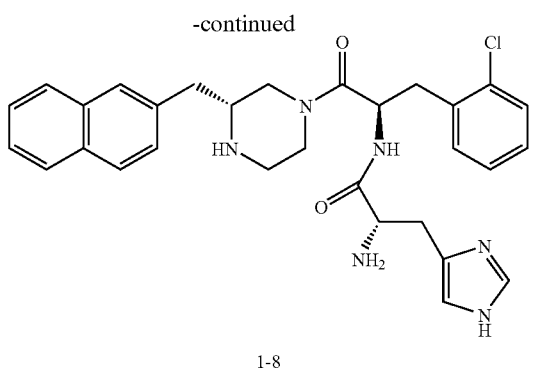

1-8

EXAMPLE 13

(R)-1,2,3,4-Tetrahydro-isoquinoline-3-carboxylic acid [(R)-1-(2-chloro-benzyl)-2-((R)-3-naphthalen-2-ylmethyl-piperazin-1-yl)-2-oxo-ethyl]-amide The following compound was synthesized by the method of Scheme 1. It was tested as described above with the results shown. The molecular weight (M+1) was 566.9.

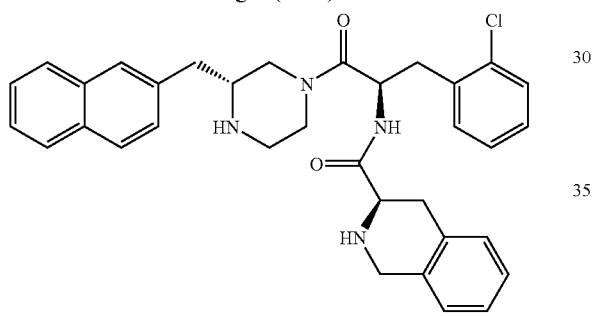

| | Inhibition at 1 μM | | | |
|---|---|---|---|---|
| MC1-R (human) | MC1-R (murine) | MC3-R | MC4-R | MC5-R |
| ND | 24 | 17 | 19 | 20 |

In the synthesis of Example 13, the starting material used in Scheme 1 was Fmoc-D-Nal 2-OH. In the synthesis of compound 1-6, Fmoc-D-Phe(2-Cl)—OH was employed as FmocNH—CH(CH$_2$—Q)—COOH. The R$_8$—COOH group was Boc-D-Tic-OH:

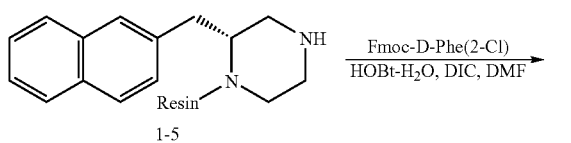

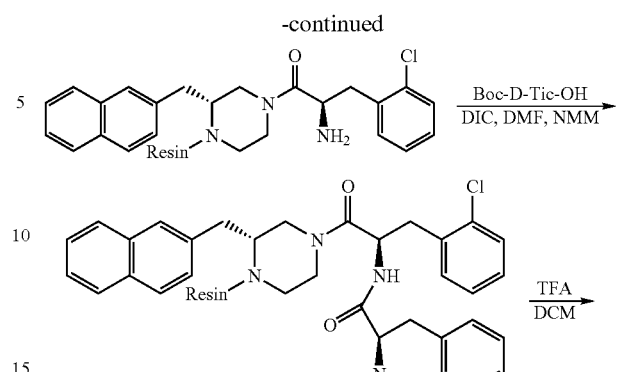

1-7

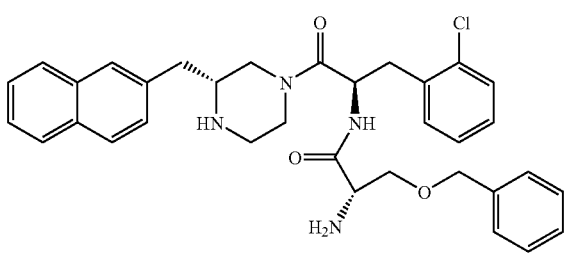

1-8

EXAMPLE 14

(S)-2-Amino-3-benzyloxy-N—[(R)-1-(2-chloro-benzyl)-2-((R)-3-naphthalen-2-ylmethyl-piperazin-1-yl)-2-oxo-ethyl]-propionamide The following compound was synthesized by the method of Scheme 1. It was tested as described above with the results shown. The molecular weight (M+1) was 585.0.

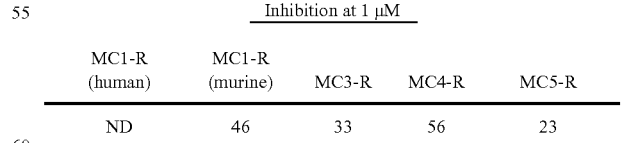

| | Inhibition at 1 μM | | | |
|---|---|---|---|---|
| MC1-R (human) | MC1-R (murine) | MC3-R | MC4-R | MC5-R |
| ND | 46 | 33 | 56 | 23 |

In the synthesis of Example 14, the starting material used in Scheme 1 was Fmoc-D-Nal 2-OH. In the synthesis of compound 1-6, Fmoc-D-Phe(2-Cl)—OH was employed as FmocNH—CH(CH$_2$—Q)—COOH. The R$_8$—COOH group was Boc-L-Ser(OBzl)-OH:

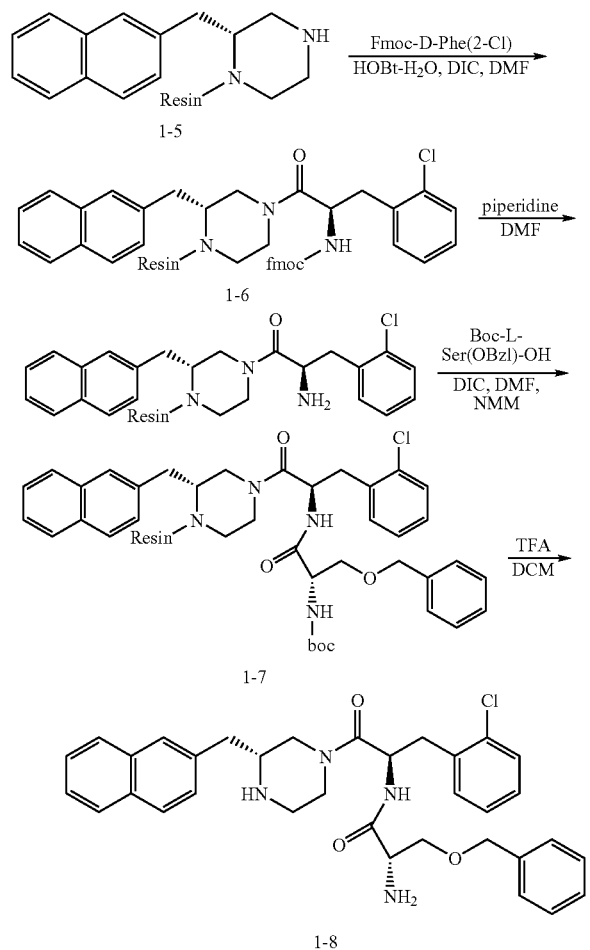

EXAMPLE 15

(R)-2-Amino-1-((2S,5R)-2,5-dibenzyl-piperazin-1-yl)-3-naphthalen-2-yl-propan-1-one The following compound was synthesized by the method of Scheme 3. It was tested as described above with the results shown. The molecular weight (M+1) was 464.3.

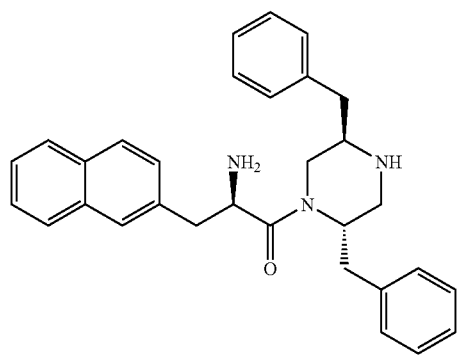

| | Inhibition at 1 μM | | | |
|---|---|---|---|---|
| MC1-R (human) | MC1-R (murine) | MC3-R | MC4-R | MC5-R |
| ND | 0 | 0 | 18 | 3 |

In the synthetic method of Scheme 3, Boc-D-Nal 2-OH was employed as the Boc-protected amino acid.

EXAMPLE 16

(R)-2-Amino-1-((2S,5R)-2,5-dibenzyl-piperazin-1-yl)-3-(2,4-dichloro-phenyl)-propan-1-one The following compound was synthesized by the method of Scheme 3. It was tested as described above with the results shown. The molecular weight (M+1) was 482.2.

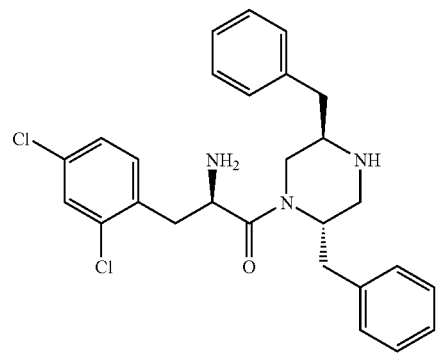

| | Inhibition at 1 μM | | | |
|---|---|---|---|---|
| MC1-R (human) | MC1-R (murine) | MC3-R | MC4-R | MC5-R |
| ND | 0 | 0 | 14 | 0 |

In the synthetic method of Scheme 3, Boc-D-Phe(2,4-diCl)—OH was employed as the Boc-protected amino acid.

EXAMPLE 17

(R)-2-Amino-1-((2S,5R)-2,5-dibenzyl-piperazin-1-yl)-3-phenyl-propan-1-One

The following compound was synthesized by the method of Scheme 3. It was tested as described above with the results shown. The molecular weight (M+1) was 414.2.

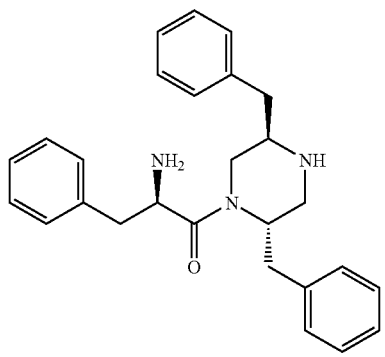

| Inhibition at 1 μM | | | | |
|---|---|---|---|---|
| MC1-R (human) | MC1-R (murine) | MC3-R | MC4-R | MC5-R |
| ND | 0 | 0 | 6 | 3 |

EXAMPLE 18

(S)-2-Amino-1-((2S,5R)-2,5-dibenzyl-piperazin-1-yl)-3-phenyl-propan-1-one

The following compound was synthesized by the method of Scheme 3. It was tested as described above with the results shown. The molecular weight (M+1) was 414.2.

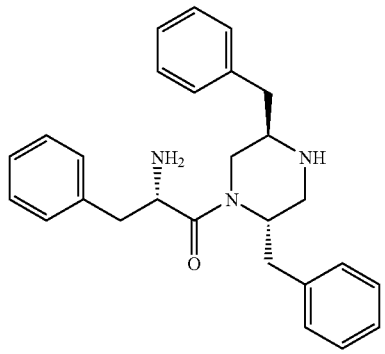

| Inhibition at 1 μM | | | | |
|---|---|---|---|---|
| MC1-R (human) | MC1-R (murine) | MC3-R | MC4-R | MC5-R |
| ND | 0 | 0 | 8 | 12 |

In the synthetic method of Scheme 3, Boc-L-Phe-OH was employed as the Boc-protected amino acid.

EXAMPLE 19

(R)-2-Amino-3-(4-chloro-phenyl)-1-((R)-3-naphthalen-2-ylmethyl-piperazin-1-yl)-propan-1-one The following compound was synthesized by the method of Scheme 1. It was tested as described above with the results shown. The molecular weight (M+1) was 408.0.

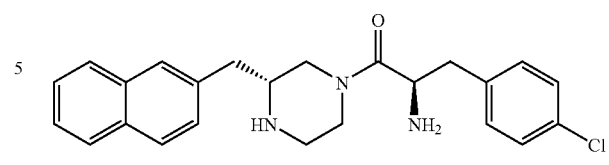

| Inhibition at 1 μM | | | | |
|---|---|---|---|---|
| MC1-R (human) | MC1-R (murine) | MC3-R | MC4-R | MC5-R |
| ND | 5 | 0 | 21 | 0 |

In the synthesis of Example 19, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. No R$_8$—COOH group was employed, so the synthetic method of Scheme 1 proceeded to treatment of the resin and purification:

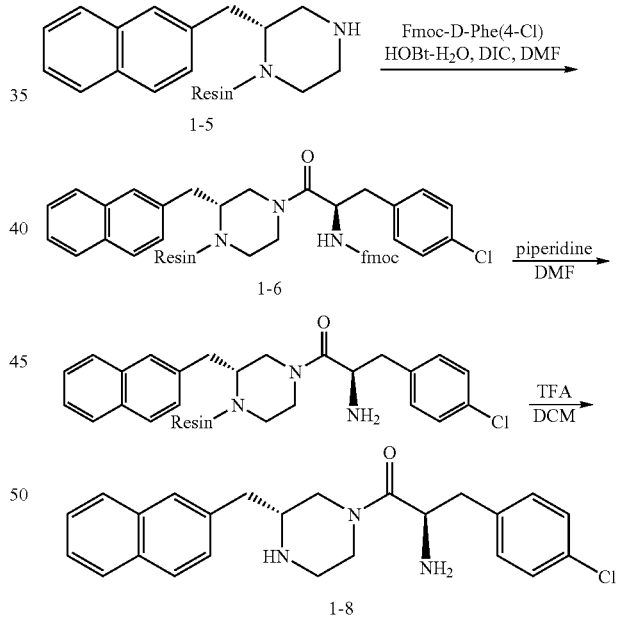

EXAMPLE 20

(S)-2-Amino-N—[(R)-1-(4-chloro-benzyl)-2-((R)-3-naphthalen-2-ylmethyl-piperazin-1-yl)-2-oxo-ethyl]-3-(1H-imidazol-4-yl)-propionamide The following compound was synthesized by the method of Scheme 1. It was tested as described above with the results shown. The molecular weight (M+1) was 545.1.

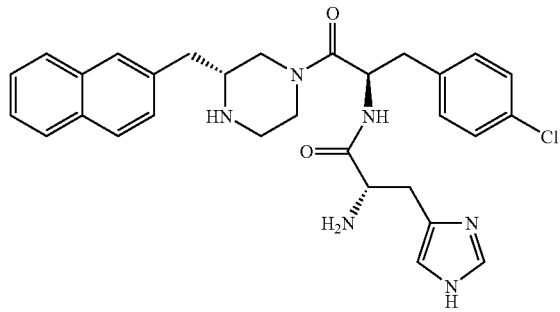

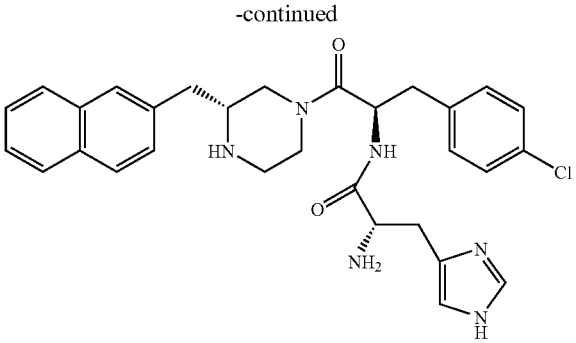

1-8

| | Inhibition at 1 μM | | | |
|---|---|---|---|---|
| MC1-R (human) | MC1-R (murine) | MC3-R | MC4-R | MC5-R |
| ND | 71 | 18 | 25 | 0 |

In the synthesis of Example 20, the starting material used in Scheme 1 was Fmoc-D-Nal 2-OH. In the synthesis of compound 1-6, Fmoc-D-Phe(4-Cl)—OH was employed as FmocNH—CH(CH₂—Q)—COOH. The R₈—COOH group was Boc-L-His(Boc)₂-OH:

EXAMPLE 21

(R)-1,2,3,4-Tetrahydro-isoquinoline-3-carboxylic acid [(R)-1-(4-chloro-benzyl)-2-((R)-3-naphthalen-2-ylmethyl-piperazin-1-yl)-2-oxo-ethyl]-amide The following compound was synthesized by the method of Scheme 1. It was tested as described above with the results shown. The molecular weight (M+1) was 567.1.

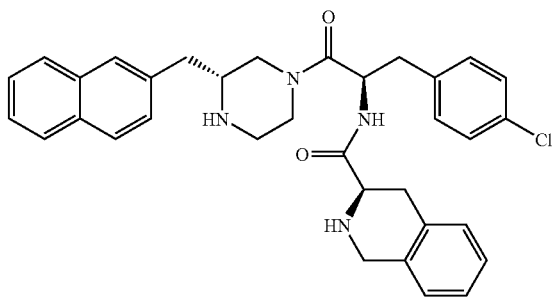

| | Inhibition at 1 μM | | | |
|---|---|---|---|---|
| MC1-R (human) | MC1-R (murine) | MC3-R | MC4-R | MC5-R |
| ND | 6 | 26 | 30 | 14 |

In the synthesis of Example 21, the starting material used in Scheme 1 was Fmoc-D-Nal 2-OH. In the synthesis of compound 1-6, Fmoc-D-Phe(4-Cl)—OH was employed as FmocNH—CH(CH₂—Q)—COOH. The R₈—COOH group was Boc-D-Tic-OH:

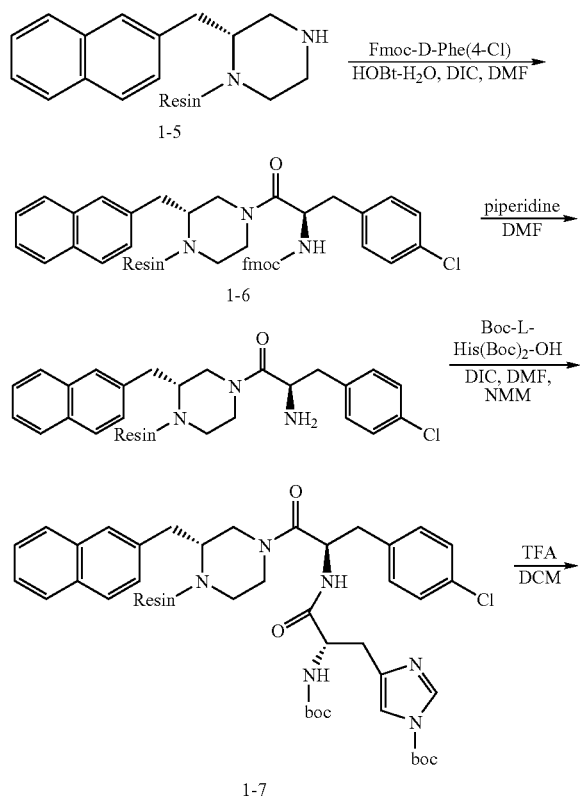

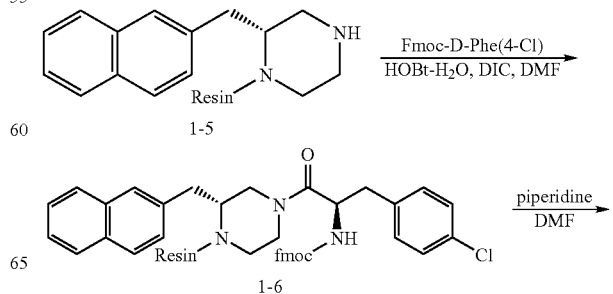

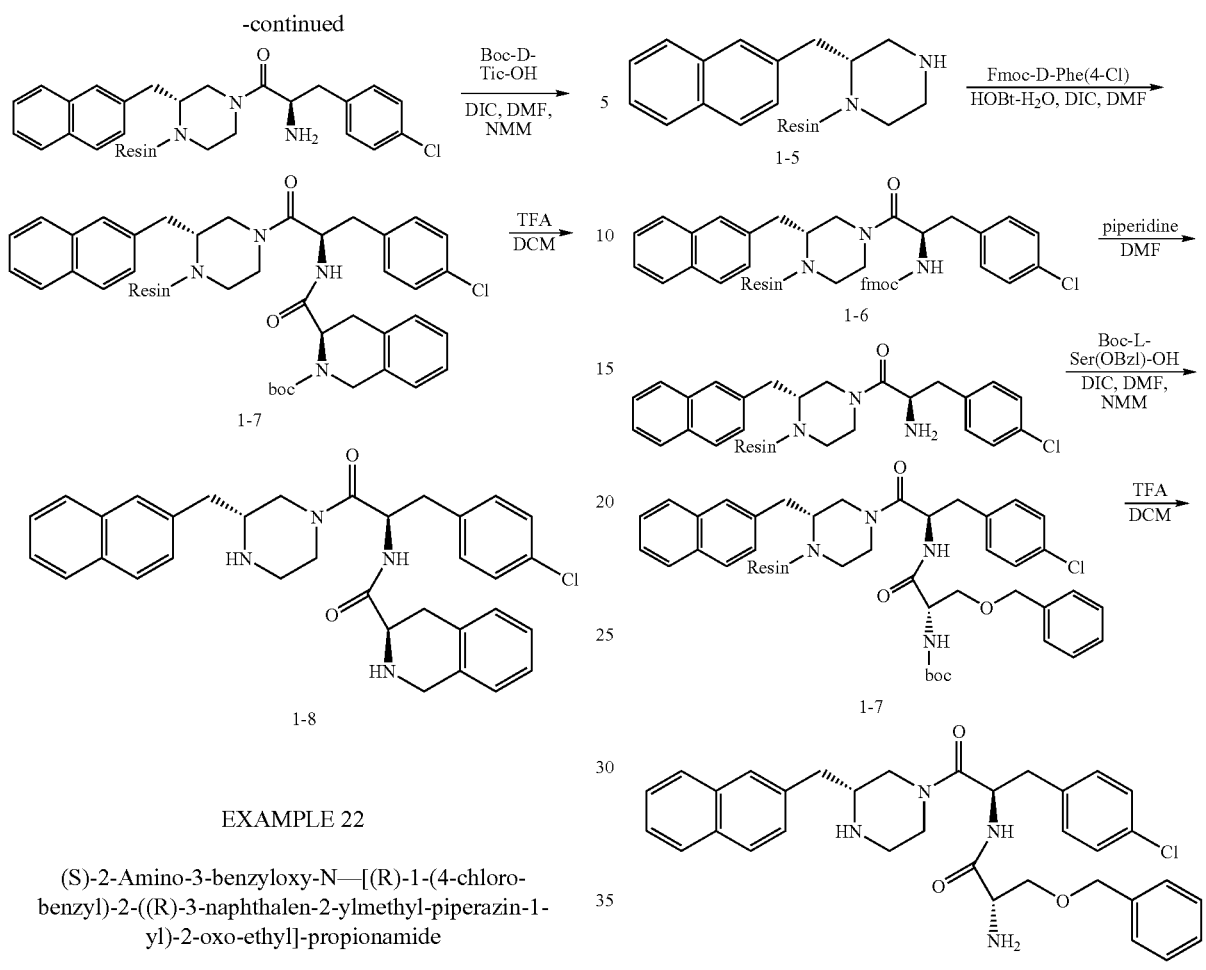

EXAMPLE 22

(S)-2-Amino-3-benzyloxy-N—[(R)-1-(4-chloro-benzyl)-2-((R)-3-naphthalen-2-ylmethyl-piperazin-1-yl)-2-oxo-ethyl]-propionamide The following compound was synthesized by the method of Scheme 1. It was tested as described above with the results shown. The molecular weight (M+1) was 585.1.

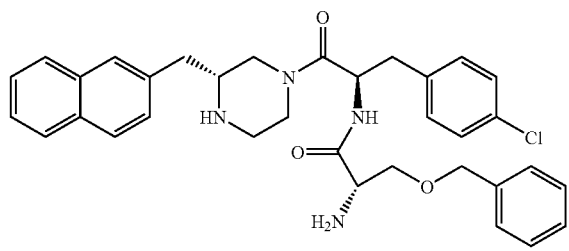

| | Inhibition at 1 μM | | | |
|---|---|---|---|---|
| MC1-R (human) | MC1-R (murine) | MC3-R | MC4-R | MC5-R |
| ND | 2 | 54 | 36 | 27 |

In the synthesis of Example 22, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COOH group was Boc-L-Ser(OBzl)-OH:

EXAMPLE 23

N—[(R)-1-(4-Chloro-benzyl)-2-((R)-3-naphthalen-2-ylmethyl-piperazin-1-yl)-2-oxo-ethyl]-acetamide The following compound was synthesized by the method of Scheme 1. It was tested as described above with the results shown. The molecular weight (M+1) was 450.2.

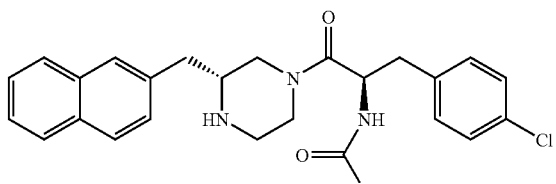

| | Inhibition at 1 μM | | | |
|---|---|---|---|---|
| MC1-R (human) | MC1-R (murine) | MC3-R | MC4-R | MC5-R |
| ND | 6 | 0 | 13 | 4 |

In the synthesis of Example 23, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COCl group was acetyl chloride:

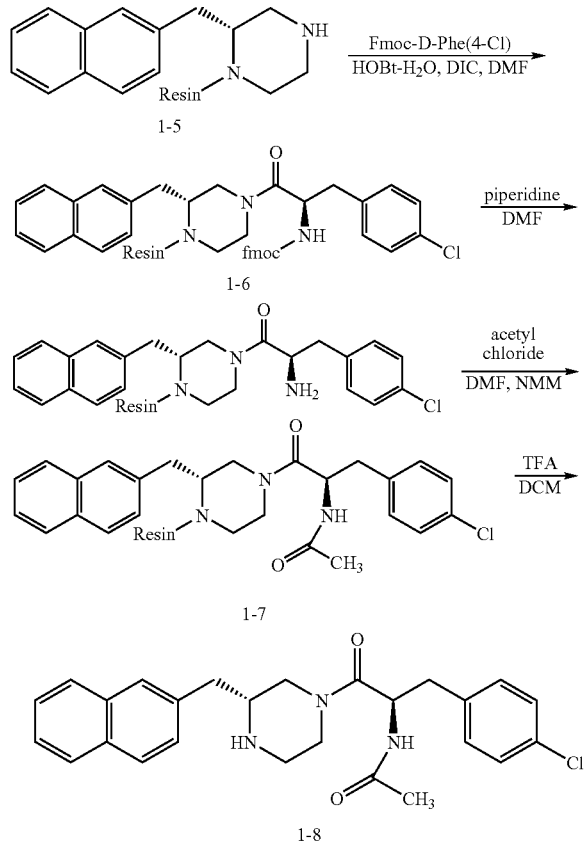

EXAMPLE 24

N—[(R)-1-(4-Chloro-benzyl)-2-((R)-3-naphthalen-2-ylmethyl-piperazin-1-yl)-2-oxo-ethyl]-4-phenyl-butyramide The following compound was synthesized by the method of Scheme 1. It was tested as described above with the results shown. The molecular weight (M+1) was 554.2.

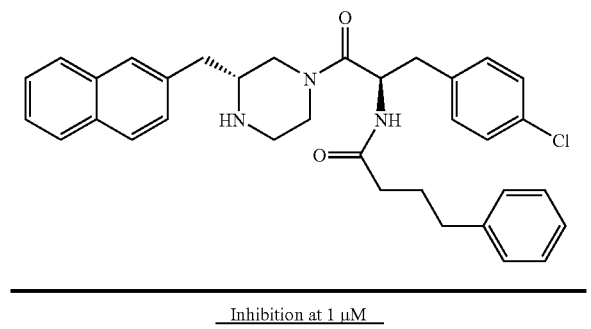

| Inhibition at 1 µM | | | | |
|---|---|---|---|---|
| MC1-R (human) | MC1-R (murine) | MC3-R | MC4-R | MC5-R |
| ND | 5 | 3 | 20 | 13 |

In the synthesis of Example 24, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COOH group was 4-phenylbutyric acid:

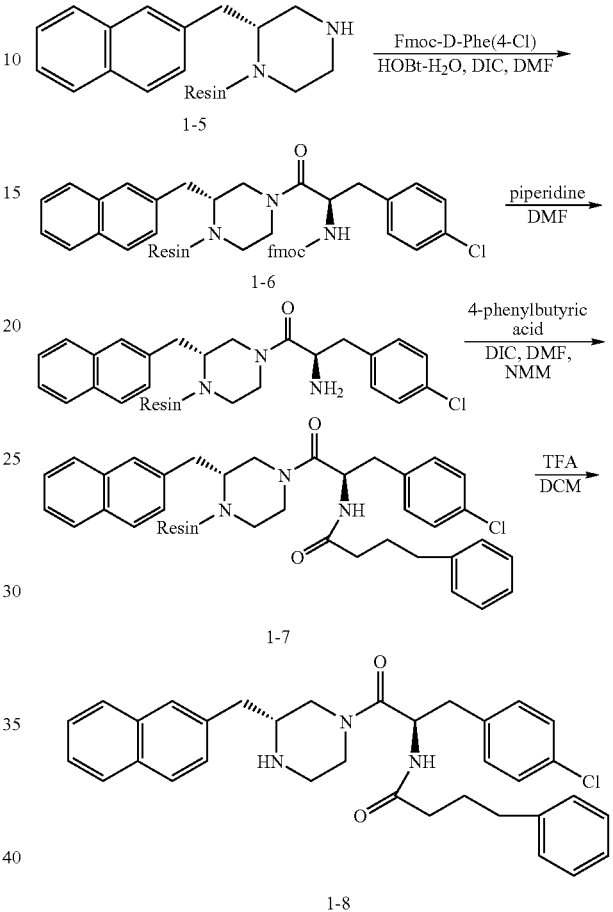

EXAMPLE 25

N—[(R)-1-(4-Chloro-benzyl)-2-((R)-3-naphthalen-2-ylmethyl-piperazin-1-yl)-2-oxo-ethyl]-2-phenyl-acetamide The following compound was synthesized by the method of Scheme 1. It was tested as described above with the results shown. The molecular weight (M+1) was 526.2.

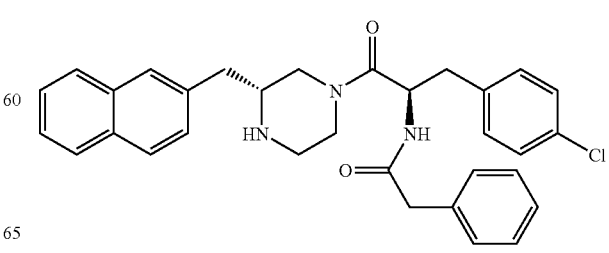

| Inhibition at 1 μM | | | | |
|---|---|---|---|---|
| MC1-R (human) | MC1-R (murine) | MC3-R | MC4-R | MC5-R |
| ND | 5 | 6 | 19 | 18 |

In the synthesis of Example 25, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COOH group was phenylacetic acid:

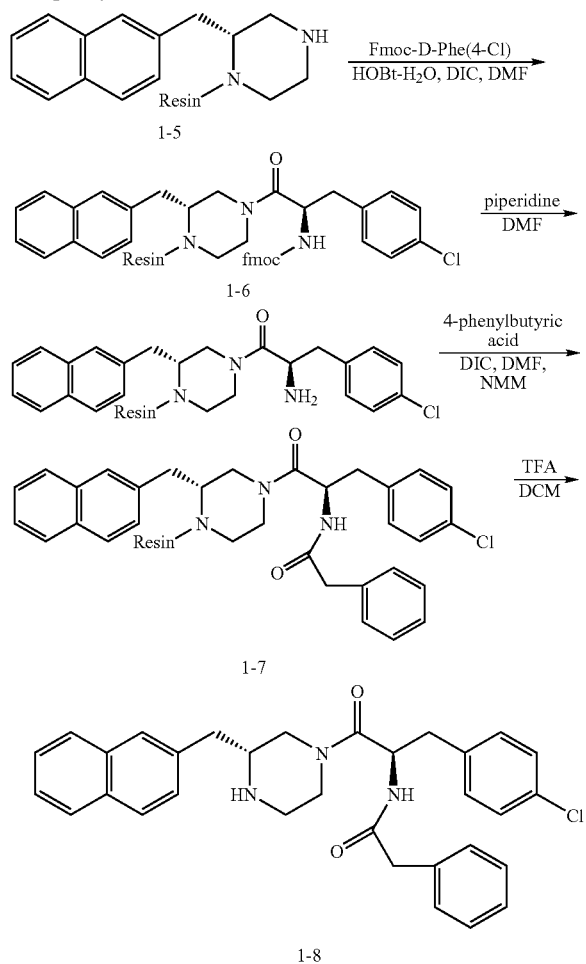

EXAMPLE 26

N—[(R)-1-(4-Chloro-benzyl)-2-((R)-3-naphthalen-2-ylmethyl-piperazin-1-yl)-2-oxo-ethyl]-4-methyl-benzenesulfonamide The following compound was synthesized by the method of Scheme 1. It was tested as described above with the results shown. The molecular weight (M+1) was 562.2.

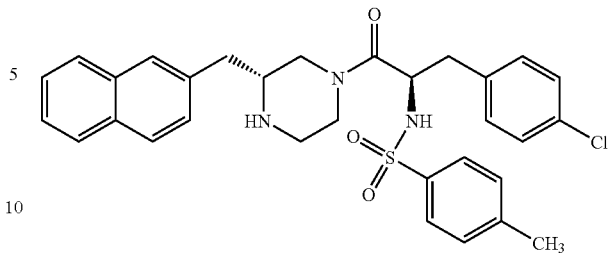

| Inhibition at 1 μM | | | | |
|---|---|---|---|---|
| MC1-R (human) | MC1-R (murine) | MC3-R | MC4-R | MC5-R |
| ND | 10 | 14 | 22 | 20 |

In the synthesis of Example 26, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COCl group was p-toluenesulfonyl chloride:

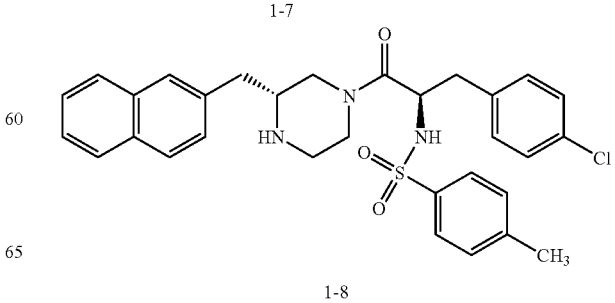

EXAMPLE 27

N—[(R)-1-(4-Chloro-benzyl)-2-((R)-3-naphthalen-2-ylmethyl-piperazin-1-yl)-2-oxo-ethyl]-2-methyl-benzamide The following compound was synthesized by the method of Scheme 1. It was tested as described above with the results shown. The molecular weight (M+1) was 570.2.

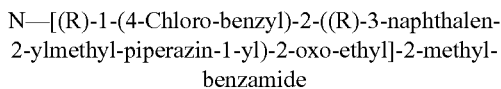

| | Inhibition at 1 μM | | | |
|---|---|---|---|---|
| MC1-R (human) | MC1-R (murine) | MC3-R | MC4-R | MC5-R |
| ND | 10 | 0 | 4 | 0 |

In the synthesis of Example 27, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COOH group was acetylsalicylic acid:

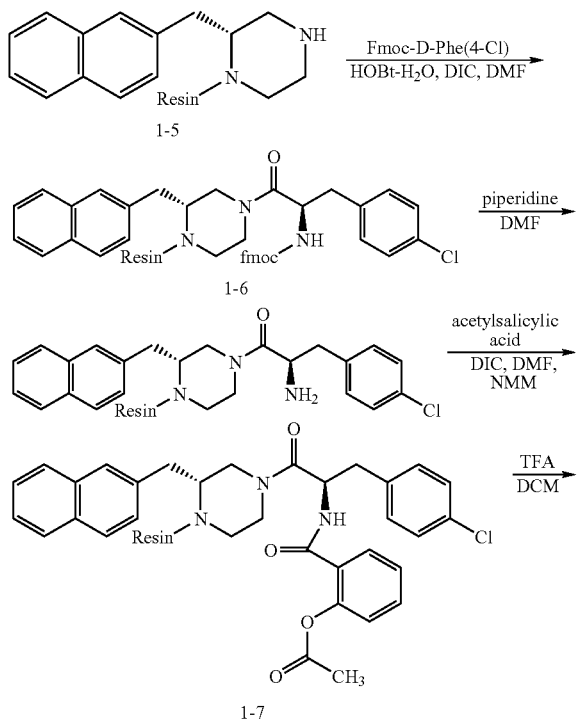

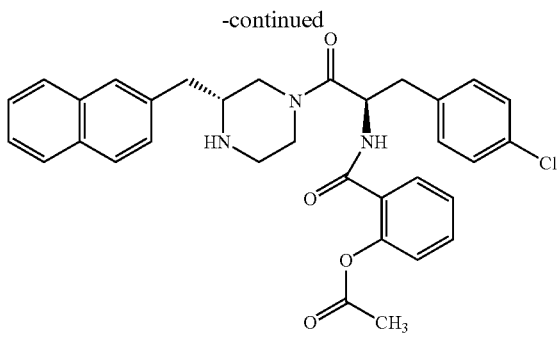

1-8

EXAMPLE 28

2-Propyl-pentanoic acid [(R)-1-(4-chloro-benzyl)-2-((R)-3-naphthalen-2-ylmethyl-piperazin-1-yl)-2-oxo-ethyl]-amide The following compound was synthesized by the method of Scheme 1. It was tested as described above with the results shown. The molecular weight (M+1) was 534.3.

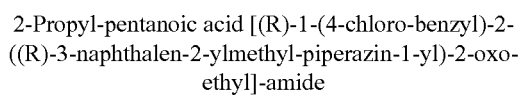

| | Inhibition at 1 μM | | | |
|---|---|---|---|---|
| MC1-R (human) | MC1-R (murine) | MC3-R | MC4-R | MC5-R |
| ND | 0 | 0 | 38 | −4 |

In the synthesis of Example 28, the starting material used in Scheme 1 was Fmoc-D-Nal 2-OH. In the synthesis of compound 1-6, Fmoc-D-Phe(4-Cl)—OH was employed as FmocNH—CH(CH$_2$—Q)—COOH. The R$_8$—COOH group was 2-propylpentanoic acid:

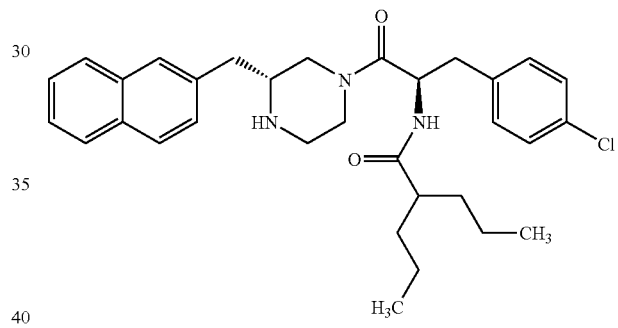

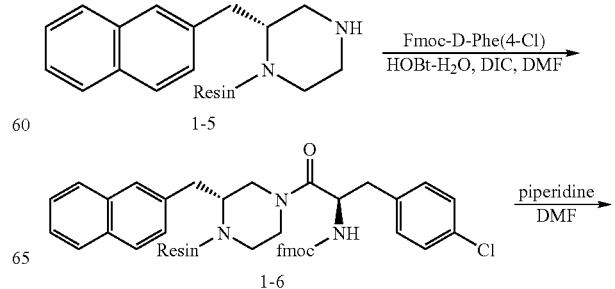

-continued

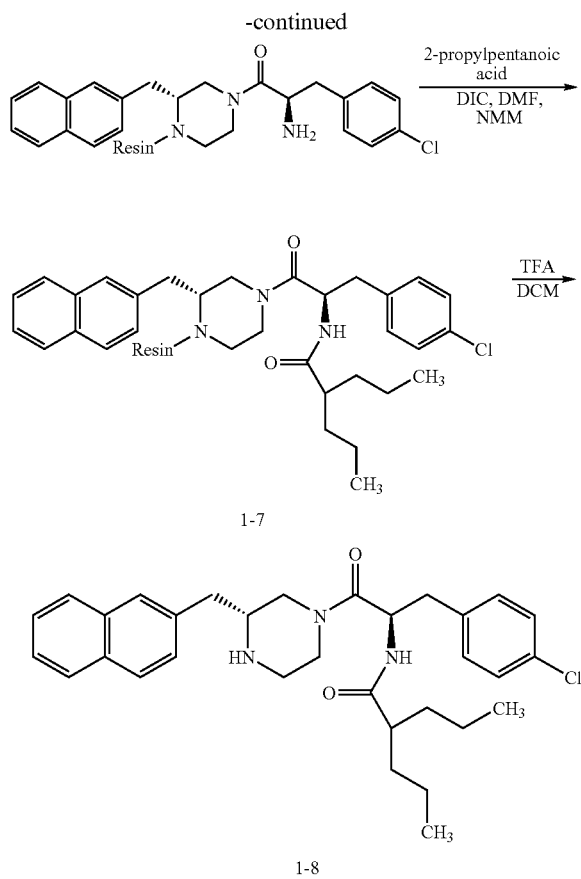

1-7

1-8

EXAMPLE 29

The compounds of Table 1 are synthesized by the methods of Schemes 6 and 7. Fmoc-Phe-OH is 6-1, and Nal 2-OMe is 6-2, and precursor 7-1 is synthesized as described. The compounds are synthesized as set forth in Scheme 7, using 7-1 as the starting material, with Route 1 employed in the synthetic scheme and using a Boc-protected amino acid as the R group. The compounds are tested as described above.

The compounds all have the following general structure:

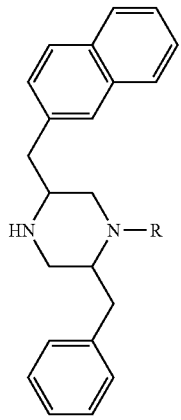

with R as shown in Table 1.

TABLE 1

| No. | R |
|---|---|
| 1-1 | ![structure] phenyl-CH2-CH(NH2)-C(O)- |
| 1-2 | ![structure] 4-methoxyphenyl-CH2-CH(NH-C(O)-CH(CH3)2)-C(O)- |
| 1-3 | ![structure] 4-chlorophenyl-CH2-CH(N(CH3)2)-C(O)- |

EXAMPLE 30

The compounds of Table 2 are synthesized by the methods of Schemes 6 and 7. Fmoc-Val-OH is 8-1, and Trp-OMe is 8-2, and precursor 9-1 is synthesized as described. The compounds are synthesized as set forth in Scheme 7, using 9-1 as the starting material, with Route 1 employed in the synthetic scheme and using a Boc-protected amino acid as the R group. The compounds are tested as described above.

The compounds all have the following general structure:

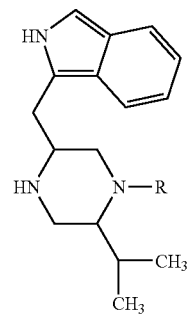

with R as shown in Table 2.

TABLE 2

| No. | R |
|---|---|
| 2-1 | ![structure] phenyl-CH2-CH(NH2)-C(O)- |
| 2-2 | ![structure] 4-methylphenyl-CH2-CH(NH2)-C(O)- |

TABLE 2-continued

| No. | R |
|---|---|
| 2-3 | 4-methoxybenzyl with C(=O)CH3 and NH2 substituents |
| 2-4 | 4-chlorobenzyl with C(=O)CH3 and N(CH3)2 substituents |
| 2-5 | 4-chlorobenzyl with C(=O)CH3 and NHCH3 substituents |
| 2-6 | 4-chlorobenzyl with C(=O)CH3 and N(CH2CH3)2 substituents |
| 2-7 | 4-chlorobenzyl with C(=O)CH3 and NH-isopropyl substituents |

EXAMPLE 31

The compounds of Table 3 are synthesized by the methods of Schemes 6 and 7. Fmoc-Gly-OH is 8-1, and Nal 2-OMe is 8-2, and precursor 9-1 is synthesized as described. The compounds are synthesized as set forth in Scheme 7, using 9-1 as the starting material, with Route 1 employed in the synthetic scheme and using a Boc-protected amino acid as the R group. The compounds are tested as described above.

The compounds all have the following general structure:

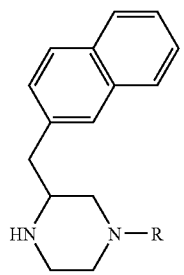

with R as shown in Table 3.

TABLE 3

| No. | R |
|---|---|
| 3-1 | benzyl with C(=O)CH3 and NH2 substituents |

TABLE 3-continued

| No. | R |
|---|---|
| 3-2 | 4-methylbenzyl with C(=O)CH3 and NH2 substituents |
| 3-3 | 4-methoxybenzyl with C(=O)CH3 and NH2 substituents |
| 3-4 | 4-chlorobenzyl with C(=O)CH3 and N(CH3)2 substituents |
| 3-5 | 4-chlorobenzyl with C(=O)CH3 and NHCH3 substituents |
| 3-6 | 4-chlorobenzyl with C(=O)CH3 and N(CH2CH3)2 substituents |
| 3-7 | 4-chlorobenzyl with C(=O)CH3 and NH-isopropyl substituents |

EXAMPLE 32

The compounds of Table 4 are synthesized by the methods of Schemes 6 and 7. Fmoc-Gly-OH is 8-1, and 2,4-chloro-Phe-OMe is 8-2, and precursor 9-1 is synthesized as described. The compounds are synthesized as set forth in Scheme 7, using 9-1 as the starting material, with Route 1 employed in the synthetic scheme and using a Boc-protected amino acid as the R group. The compounds are tested as described above.

The compounds all have the following general structure:

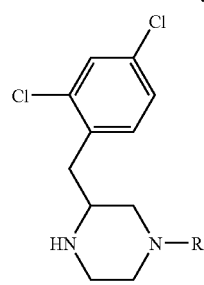

with R as shown in Table 4.

TABLE 4

| No. | R |
|-----|---|
| 4-1 | 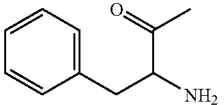 |
| 4-2 | 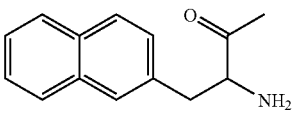 |
| 4-3 | 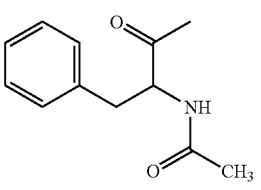 |
| 4-4 | 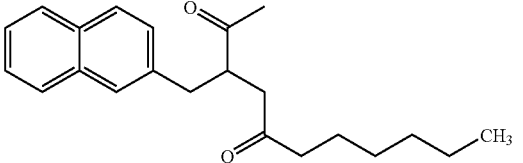 |
| 4-5 | 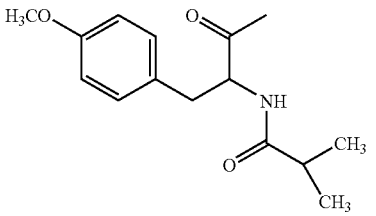 |
| 4-6 | 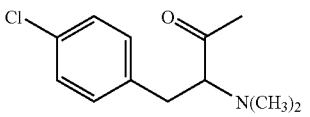 |
| 4-7 | 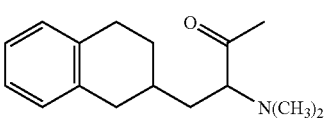 |
| 4-8 | 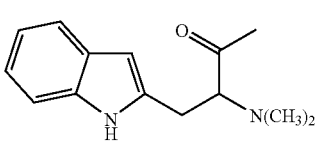 |

EXAMPLE 33

The compounds of Table 5 are synthesized by the methods of Schemes 6 and 7. Fmoc-4-methyl-phenylalanine is 6-1, and Gly-methyl ester is 6-2, and precursor 7-1 is synthesized as described. The compounds are synthesized as set forth in Scheme 7, using 7-1 as the starting material, with Route 1 employed in the synthetic scheme and using a Boc-protected amino acid as the R group. The compounds are tested as described above.

The compounds of Table 5 have the following general structure

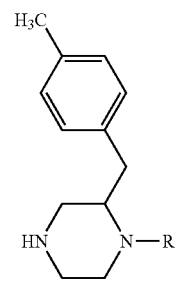

with R as shown in Table 5.

TABLE 5

| No. | R |
|-----|---|
| 5-1 | 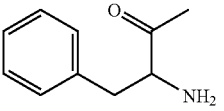 |
| 5-2 | 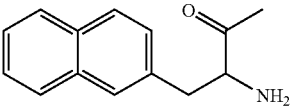 |
| 5-3 | 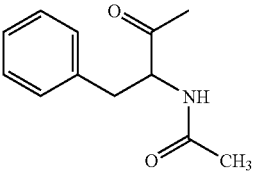 |
| 5-4 | 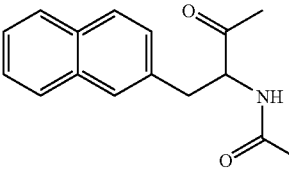 |
| 5-5 | 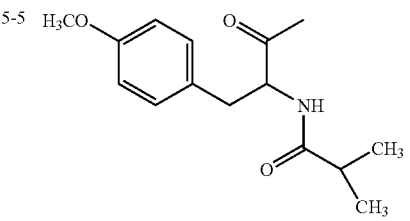 |
| 5-6 | 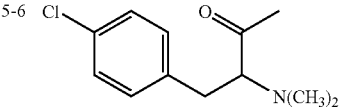 |
| 5-7 | 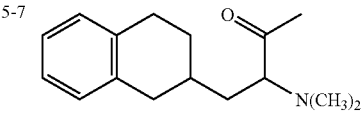 |

TABLE 5-continued

| No. | R |
|---|---|
| 5-8 | 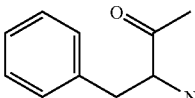 |

EXAMPLE 33

The compounds of Table 6 are synthesized by the methods of Schemes 6 and 7. Fmoc-Leu-COOH is 8-1, and 2,4-dichloro-phenylalanine methyl ester is 8-2, and precursor 9-1 is synthesized as described. The compounds are synthesized as set forth in Scheme 7, using 9-1 as the starting material, with Route 1 employed in the synthetic scheme and using a Boc-protected amino acid as the R group. The compounds are tested as described above.

The compounds of Table 6 have the following general structure:

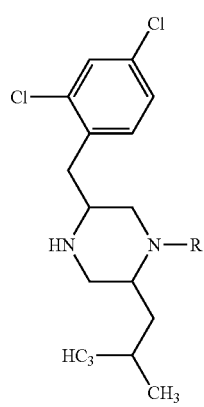

with R as shown in Table 6.

TABLE 6

| No. | R |
|---|---|
| 6-1 | 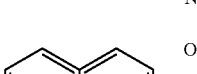 |
| 6-2 | |
| 6-3 | |

TABLE 6-continued

| No. | R |
|---|---|
| 6-4 | 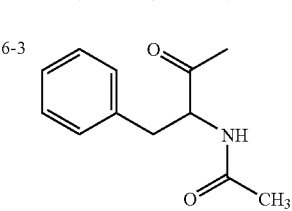 |
| 6-5 | |
| 6-6 | |
| 6-7 | |
| 6-8 | |

EXAMPLE 34

The compounds of Table 7 are synthesized by the methods of Schemes 6 and 7. Fmoc-4-methyl-Phe-COOH is 6-1, and phenylalanine methyl ester is 6-2, and precursor 7-1 is synthesized as described. The compounds are synthesized as set forth in Scheme 7, using 7-1 as the starting material, with Route 1 employed in the synthetic scheme and using a Boc-protected amino acid as the R group. The compounds are tested as described above.

The compounds of Table 7 have the following general structure:

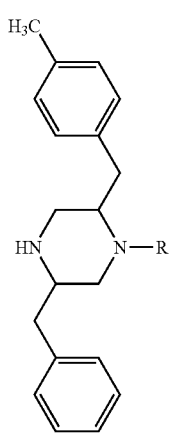

with R as shown in Table 7.

TABLE 7

| No. | R |
|---|---|
| 7-1 | |
| 7-2 | |
| 7-3 | |
| 7-4 | |
| 7-5 | |
| 7-6 | |
| 7-7 | |

TABLE 7-continued

| No. | R |
|---|---|
| 7-8 | |

The preceding examples can be repeated with similar success by substituting the generically or specifically described reactants and/or synthetic conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above, and of the corresponding application(s), are hereby incorporated by reference.

What is claimed is:

1. A compound of formula I:

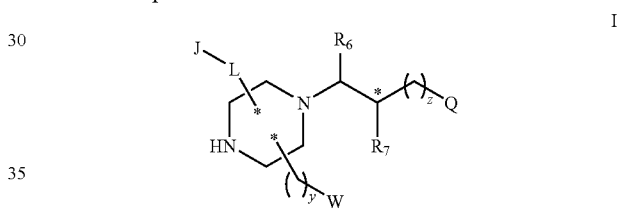

or an enantomeric, stereoisomeric or diastereomeric form of the foregoing, and pharmaceutically acceptable salts thereof;

wherein

J is a substituted or unsubstituted monocyclic or bicyclic ring structure selected from the group consisting of

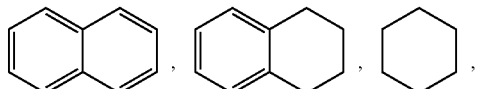

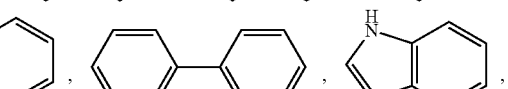

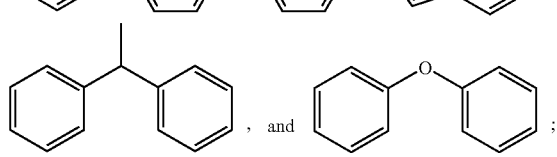

L is a bond, $-(CH_2)_q-$, $-(CH_2)_q-O-$, $-(CH_2)_q-O-(C=O)-$, $-(CH_2)_q(C=O)-$ or $-(CH_2)_q-(C=O)-O-$;

W is H or a substituted or unsubstituted aryl group;

Q is phenyl, substituted phenyl, naphthyl or substituted naphthyl;

$R_6$ is H, =O, =S or $CH_3$;

$R_7$ is H, $NH_2$, $NH-R_8$, or

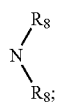

$R_8$ is a $C_1$ to $C_6$ linear or branched chain, an amine capping group, a natural or unnatural amino acid containing an aliphatic or aromatic side chain, or a natural or unnatural amino acid containing an aliphatic or aromatic side chain with a pendant amine capping group, and where there are two $R_8$ groups, each $R_8$ is independently a $C_1$ to $C_6$ linear or branched chain or an amine capping group, or one $R_8$ is a $C_1$ to $C_6$ linear or branched chain or an amine capping group and the remaining $R_8$ is a natural or unnatural amino acid containing an aliphatic or aromatic side chain or a natural or unnatural amino acid containing an aliphatic or aromatic side chain with a pendant amine capping group, wherein the amine capping group is allyl, cyclopropane methyl, hexanoyl, heptanoyl, acetyl, propionoyl, butanoyl, phenyl acetyl, phenyl propinoyl, phenyl butanoyl, cyclohexylacetyl, naphthylacetyl, cinnamoyl, phenyl, benzyl, benzoyl, ring-substituted benzoyl, 4'-toluenesulfonyl, 4'-carboxy heptane, 12-Ado, 7r-amino heptanoyl, 6-Ahx, Amc, 8-Aoc, or polyethylene glycol with a formula molecular weight of between about 100 and about 10,000;

q is from 1 to 6;
y is from 0 to 6;
z is from 0 to 6; and
wherein the carbon atoms marked with an asterisk can have any stereochemical configuration.

2. The compound of claim 1 wherein $R_6$ is H or =O.
3. The compound of claim 1
wherein
J is phenyl, substituted phenyl, naphthyl or substituted naphthyl;
L is —$CH_2$— or —$(CH_2)_2$—;
Q is phenyl, substituted phenyl, naphthyl or substituted naphthyl;
W is H or phenyl;
$R_6$ is H or =O;
$R_7$ is $NH_2$, NH—$R_8$, or

y is 0 if W is H, and otherwise y is 1; and
z is 1 or 2.

4. The compound of claim 1 wherein $R_7$ is $NH_2$, $N(CH_3)_2$, $NHCH_3$,

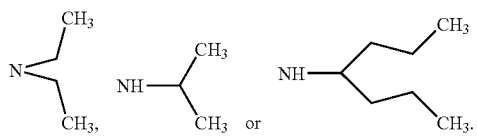

5. The compound of claim 1 wherein the natural or unnatural amino acid containing an aliphatic or aromatic side chain is an L- or D-isomer of Phe, Phe(2-Cl), Phe(4-Cl), Phe(2,4-diCl), Phe(2,4-diF), Phe(3,4-diCl), Phe(4-$NO_2$), Phe(4-Me), Phe(4-Phenyl), HPhe, pF-Phe, Phe(4-Br), Phe(4-$CF_3$), Phe (3,4-diF), Phe(4-I), Phe(2-Cl, 4-Me), Phe(2-Me, 4-Cl), Phe (2-F, 4-Cl), Phe(2,4-diMe), Phe(2-Cl, 4-$CF_3$), Phe(3,4-di-OMe), Phg, Trp, Nal 1, Nal 2, Bip, Dip, Bpa, Ser(Bzl), Ser (2-Naphthyl), Ser(Phenyl), Ser(4-Cl-Phenyl), Ser(2-Cl-Phenyl), Lys(Z), Lys(Z-2'Br), Lys(Bz), Thr(Bzl), Tic, Tiq, Cys(Bzl), Tyr(2,6-DiCl-Bzl), Tyr(Bzl), Abu, 2-Abz, 3-Abz, 4-Abz, Ache, Acpe, Aib, Abn, Arg(Tos), Asp(anilino), Asp(3-Cl-anilino), Asp(3,5-diCl-anilino), 11-Aun, AVA, Beta-hHyp (Bzl), Cha, Chg, Cmpi, Disc, Dpr(beta-Ala), GAA, GBzA, B-Spa, GVA(Cl), His, hSer, Ser(Bzl), Tic, hHyp, Hyp(Bzl), Inp, 2-Naphthylacetyl, (Nlys)Gly, OcHx, Pip, 4-phenylPro, 5-phenylPro, Pyr, Sar, Tle, Tiq, Atc, Igl, Hyp(O-2-Naphthyl), Hyp(O-Phenyl), 2-Aic, Idc, 1-Aic, Beta-homoSer(Bzl), Ser (O-2-Naphthyl), Ser(O-Phenyl), Ser(O-4-Cl-Phenyl), Ser(O-2-Cl-Phenyl), Thr(Bzl), Tic, Beta-homoThr(Bzl), Thr(O-2-Naphthyl), Thr(O-Phenyl), Thr(O-4-Cl-Phenyl), Thr(O-2-Cl-Phenyl), Nle, Leu, Ile, Val or Beta-Ala.

6. The compound of claim 1 wherein J is substituted at one or more positions with one or more hydroxyl, halogen, alkyl or aryl groups.

7. The compound of claim 1 wherein Q is:

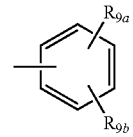

wherein $R_{9a}$ and $R_{9b}$ are optional ring substituents, and when one or both are present, are the same or different and independently hydroxyl, halogen, alkyl, or aryl groups attached directly or through an ether linkage.

8. The compound of claim 1 of formula II:

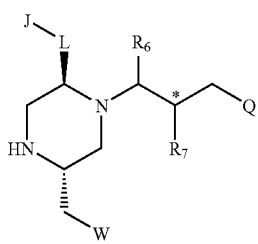

II and pharmaceutically acceptable salts thereof.

9. The compound of claim 8 of formula III:

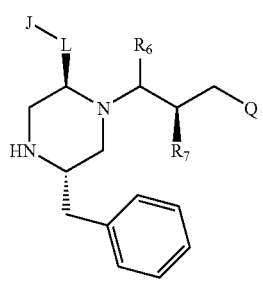

III and pharmaceutically acceptable salts thereof.

10. The compound of claim 9 of formula IV:

IV and pharmaceutically acceptable salts thereof,
wherein
J is phenyl, substituted phenyl, naphthyl or substituted naphthyl; and
$R_{9a}$ and $R_{9b}$ are optional ring substituents, and when one or both are present, are the same or different and independently hydroxyl, halogen, alkyl, or aryl groups attached directly or through an ether linkage.

11. The compound of claim 8 of formula V:

V and pharmaceutically acceptable salts thereof.

12. The compound of claim 1 of formula VI:

VI and pharmaceutically acceptable salts thereof.

13. The compound of claim 1 of formula VII:

VII and pharmaceutically acceptable salts thereof.

14. The compound of claim 13 of formula VIII:

VIII and pharmaceutically acceptable salts thereof,
wherein $R_{9a}$ and $R_{9b}$ are optional ring substituents, and when one or both are present, are the same or different and independently hydroxyl, halogen, alkyl, or aryl groups attached directly or through an ether linkage.

15. A compound of formula IX:

IX or an enantomeric, stereoisomeric or diastereomeric form of the foregoing, and pharmaceutically acceptable salts thereof;
wherein
J is a substituted or unsubstituted monocyclic or bicyclic ring structure selected from the group consisting of

, , ,

, , ,

, and ;

L is a bond, $-(CH_2)_q-$, $-(CH_2)_q-O-$, $-(CH_2)_q-O-(C=O)-$, $-(CH_2)_q-NH-$, $-(CH_2)_q-NH-(C=O)-$, $-(CH_2)_q-(C=O)-$, $-(CH_2)_q-(C=O)-NH-$ and $-(CH_2)_q-(C=O)-O-$;
A is a $C_1$ to $C_6$ linear or branched chain;
Q is phenyl, substituted phenyl, naphthyl or substituted naphthyl;
$R_6$ is H, =O, =S or $CH_3$;
$R_7$ is H, $NH_2$, $NH-R_8$, or $R_8$ is a $C_1$ to $C_6$ linear or branched chain, an amine capping group, a natural or unnatural amino acid containing an aliphatic or aromatic side chain, or a natural or unnatural amino acid containing an aliphatic or aromatic side chain with a pendant amine capping group, and where there are two $R_8$ groups, each $R_8$ is independently a $C_1$ to $C_6$ linear or branched chain or an amine capping group, or one $R_8$ is a $C_1$ to $C_6$ linear or branched chain or an amine capping group and the remaining $R_8$ is a natural or unnatural amino acid containing an aliphatic or aromatic side chain or a natural or unnatural amino acid containing an aliphatic or aromatic side chain with a pendant amine capping group, wherein the amine capping group is allyl, cyclopropane methyl, hexanoyl, heptanoyl, acetyl, propionoyl, butanoyl, phenyl acetyl, phenyl propinoyl, phenyl butanoyl, cyclohexylacetyl, naphthylacetyl, cinnamoyl, phenyl, benzyl, benzoyl, ring-substituted benzoyl, 4'-toluenesulfonyl, 4'-carboxy heptane, 12-Ado, 7'-amino heptanoyl, 6-Ahx, Amc, 8-Aoc, or polyethylene glycol with a formula molecular weight of between about 100 and about 10,000;

q is from 1 to 6;

y is from 0 to 6;

z is from 0 to 6; and wherein the carbon atoms marked with an asterisk can have any stereochemical configuration.

16. A pharmaceutical composition for treatment of a melanocortin receptor-associated disorder, comprising a compound of claim 1 and a pharmaceutically acceptable carrier, wherein the melanocortin receptor-associated disorder is cachexia, obesity, erectile dysfunction or female sexual dysfunction.

17. A method for treating a melanocortin receptor-associated disorder, comprising administering a therapeutically effective amount of a pharmaceutical composition of claim 16, wherein the melanocortin receptor-associated disorder is cachexia, obesity, erectile dysfunction or female sexual dysfunction.

18. A pharmaceutical composition comprising a compound of claim 1 and a pharmaceutically acceptable carrier.

19. A method for treating a melanocortin receptor-associated disorder, comprising administering a therapeutically effective amount of a pharmaceutical composition of claim 18, wherein the melanocortin receptor-associated disorder is cachexia, obesity, erectile dysfunction or female sexual dysfunction.

* * * * *

UNITED STATES PATENT AND TRADEMARK OFFICE
CERTIFICATE OF CORRECTION

| | |
|---|---|
| PATENT NO. | : 7,709,484 B1 |
| APPLICATION NO. | : 11/110060 |
| DATED | : May 4, 2010 |
| INVENTOR(S) | : Shubh D. Sharma et al. |

It is certified that error appears in the above-identified patent and that said Letters Patent is hereby corrected as shown below:

Claim 1, column 85, line 27, delete "7r-amino" and insert --7'-amino--.

Claim 5, column 86, line 11, delete "Abn" and insert --Amb--.

Claim 5, column 86, line 14, delete "B-Spa" and insert --B-Gpa--.

Signed and Sealed this

Fifteenth Day of June, 2010

David J. Kappos
*Director of the United States Patent and Trademark Office*